United States Patent
Ish-Yamini Tomer et al.

(10) Patent No.: US 10,266,802 B2
(45) Date of Patent: *Apr. 23, 2019

(54) METHOD FOR CONTROLLING BIOLOGICAL PROCESSES IN MICROORGANISMS

(71) Applicant: ORTERON (T.O) LTD., Kfar Saba (IL)

(72) Inventors: Orit Ish-Yamini Tomer, Netanya (IL); Tamar Levin, Kfar Saba (IL)

(73) Assignee: ORTERON (T.O) LTD., Kfar Saba (IL)

( * ) Notice: Subject to any disclaimer, the term of this patent is extended or adjusted under 35 U.S.C. 154(b) by 620 days.

This patent is subject to a terminal disclaimer.

(21) Appl. No.: 14/875,864

(22) Filed: Oct. 6, 2015

(65) Prior Publication Data

US 2016/0023183 A1    Jan. 28, 2016

Related U.S. Application Data

(63) Continuation-in-part of application No. 14/525,802, filed on Oct. 28, 2014, which is a continuation-in-part
(Continued)

(30) Foreign Application Priority Data

May 1, 2013    (IL) .......................................... 226105
May 2, 2013    (DE) .................... 20 2013 101 914 U
Jul. 1, 2013    (DE) .................... 20 2013 102 880 U

(51) Int. Cl.
*C12M 1/42*    (2006.01)
*B01J 19/08*    (2006.01)
(Continued)

(52) U.S. Cl.
CPC ........... *C12M 35/08* (2013.01); *A61B 18/042* (2013.01); *A61D 7/00* (2013.01); *A61N 1/44* (2013.01);
(Continued)

(58) Field of Classification Search
CPC ... C12M 35/08; C12N 13/00; H01J 37/32009; H01J 37/32018; H01J 37/32027;
(Continued)

(56) References Cited

U.S. PATENT DOCUMENTS 4,739,169 A * 4/1988 Kurosawa ............... H01J 37/08 250/423 R
4,978,346 A * 12/1990 Bentley .................. A61B 18/28 606/27

(Continued)

FOREIGN PATENT DOCUMENTS

KR    2014/0002357 A    1/2014
WO    2005/084569 A1    9/2005
(Continued)

OTHER PUBLICATIONS

International Search Report of PCT/IL2014/050053, dated Jul. 24, 2014.
(Continued)

*Primary Examiner* — Andrew M Gilbert
(74) *Attorney, Agent, or Firm* — The Roy Gross Law Firm, LLC; Roy Gross

(57) ABSTRACT

The present invention discloses a method for providing at least one biological effect in at least one microorganism. The aforementioned method comprises steps of: (a) providing a system for administering modified plasma; (b) providing a substrate hosting said at least one microorganism; and (c) administering the generated modified plasma beam in a predetermined pulsed manner to said substrate hosting said
(Continued)

US 10,266,802 B2
Page 2 at least one microorganism to provide said at least one biological effect to said at least one microorganism. The present invention further provides a system thereof.

15 Claims, 20 Drawing Sheets

Related U.S. Application Data of application No. PCT/IL2014/050053, filed on Jan. 16, 2014, which is a continuation-in-part of application No. 13/874,547, filed on May 1, 2013, now Pat. No. 8,896,211.

(60) Provisional application No. 61/753,022, filed on Jan. 16, 2013.

(51) Int. Cl.

| | | |
|---|---|---|
| C12N 13/00 | (2006.01) | |
| A61N 1/44 | (2006.01) | |
| A61D 7/00 | (2006.01) | |
| A61B 18/04 | (2006.01) | |
| B09C 1/00 | (2006.01) | |
| B09C 1/08 | (2006.01) | |
| H01J 37/32 | (2006.01) | |
| C02F 1/30 | (2006.01) | |
| A61B 18/00 | (2006.01) | |
| A61H 33/14 | (2006.01) | |
| H05H 1/24 | (2006.01) | |
| H05H 1/46 | (2006.01) | |
| H05H 1/48 | (2006.01) | |
| C02F 1/46 | (2006.01) | |

(52) U.S. Cl.
CPC ............... *B01J 19/088* (2013.01); *B09C 1/00* (2013.01); *B09C 1/08* (2013.01); *C12N 13/00* (2013.01); *H01J 37/32091* (2013.01); *A61B 2018/00345* (2013.01); *A61B 2018/00434* (2013.01); *A61B 2018/00452* (2013.01); *A61B 2018/00583* (2013.01); *A61H 2033/141* (2013.01); *B01J 2219/0877* (2013.01); *C02F 1/30* (2013.01); *C02F 1/4608* (2013.01); *C02F 2303/04* (2013.01); *H01J 37/32669* (2013.01); *H05H 2001/2412* (2013.01); *H05H 2001/2481* (2013.01); *H05H 2001/4697* (2013.01); *H05H 2001/483* (2013.01); *H05H 2240/20* (2013.01); *H05H 2277/10* (2013.01); *Y10T 29/42* (2015.01); *Y10T 29/49002* (2015.01)

(58) Field of Classification Search
CPC ........... H01J 37/32036; H01J 37/32055; H01J 37/32073; H01J 37/32082; H01J 37/32137; H01J 37/32146; H01J 37/32155; H01J 37/32321; H01J 37/32348; H01J 37/32623; H01J 37/32642; H01J 37/32651; H01J 37/3266; H01J 37/32669; A61L 2/14; A61L 33/0094; A61L 2400/18; A61F 2013/51069; A61B 18/042; A61B 2018/00583

See application file for complete search history.

(56) References Cited

U.S. PATENT DOCUMENTS

| | | | | |
|---|---|---|---|---|
| 5,081,398 A * | 1/1992 | Asmussen | ......... | H01J 37/32192 118/723 R |
| 5,189,446 A * | 2/1993 | Barnes | ............... | H01J 37/32192 313/231.31 |
| 5,562,952 A * | 10/1996 | Nakahigashi | ......... | C23C 16/405 118/50 |
| 5,895,558 A * | 4/1999 | Spence | ................... | H01J 37/32 204/164 |
| 6,099,523 A * | 8/2000 | Kim | ...................... | A61B 18/042 606/40 |
| 6,387,088 B1 * | 5/2002 | Shattuck | .............. | A61B 18/042 128/898 |
| 6,911,779 B2 * | 6/2005 | Madocks | ................ | C23C 16/50 118/723 FI |
| 7,220,261 B2 * | 5/2007 | Truckai | ............ | A61B 17/22004 606/41 |
| 7,323,821 B2 * | 1/2008 | Schwarzl | ............... | B82Y 10/00 250/396 ML |
| 7,493,969 B2 * | 2/2009 | Burnett | ................... | B63B 27/20 175/88 |
| 8,896,211 B2 * | 11/2014 | Ish-Yamini Tomer | ... | H05H 1/24 315/111.21 |
| 2001/0034519 A1 * | 10/2001 | Goble | .................. | A61B 18/042 606/41 |
| 2002/0161362 A1 | 10/2002 | Penny et al. | | |
| 2002/0175068 A1 | 11/2002 | Hammerstrom et al. | | |
| 2003/0103877 A1 * | 6/2003 | Long | ................ | H01J 37/32009 422/186.04 |
| 2003/0125727 A1 * | 7/2003 | Truckai | ............ | A61B 17/22004 606/41 |
| 2006/0189976 A1 * | 8/2006 | Karni | ................... | A61B 18/042 606/41 |
| 2008/0017616 A1 * | 1/2008 | Lee | .......................... | H05H 1/46 219/121.48 |
| 2009/0012589 A1 * | 1/2009 | Watson | .................... | H05H 1/46 607/99 |
| 2010/0130911 A1 | 5/2010 | Morfill et al. | | |
| 2010/0145253 A1 * | 6/2010 | Gutsol | ................ | A61B 18/042 604/20 |
| 2010/0296977 A1 * | 11/2010 | Hancock | .................... | A61L 2/14 422/186 |
| 2013/0026919 A1 * | 1/2013 | Rosener | .................... | H05H 1/48 315/111.41 |
| 2013/0072859 A1 * | 3/2013 | Watson | ................. | A61M 16/12 604/23 |
| 2013/0345620 A1 * | 12/2013 | Zemel | .................. | A61B 18/042 604/24 |
| 2014/0074090 A1 * | 3/2014 | Lam | ...................... | A61B 18/042 606/49 |

FOREIGN PATENT DOCUMENTS

| | | |
|---|---|---|
| WO | 2008/131407 A1 | 10/2008 |
| WO | 2012/003348 A2 | 1/2012 |
| WO | 2014/111935 A1 | 7/2014 |

OTHER PUBLICATIONS

Written Opinion of PCT/IL2014/050053, dated Jul. 16, 2015.

"Effects of Non-Thermal Plasma on Mammalian Cells", S. Kalghatgi et al., PLoS ONE, vol. 6, Issue 1, pp. 1-11, (Jan. 2011), www.plosone.org.

"The Effect of Plasma Treatment of Seeds of Some Grain and Legumes, on their Sowing Quality and Productivity", I . Filatova et al., Romanian Journal of Physics, vol. 56, Supplement, pp. 139-143, Bucharest (2011).

"Influence of Plasma Treatment on Wheat and Oat Germination and Early Growth", S. Bozena et al, IEEE Transactions on Plasma Science—IEEE Trans Plasma Sci, vol. 38, No. 10, pp. 2963-2968 (2010).

"Analysis of the Biological Effects of a Non-Thermal Plasma on Saccharomyces Cerevisiae", Park et al., Journal of the Korean Physical Society, vol. 60, pp. 160-120 (2012).

"Metabolic Engineering of Saccharomyces Cerevisiae for the Production of n-butanol", Steen et al., Microbial Cell Factories, vol. 7, pp. 1-8, (2008).

"Utilizing an Endogenous Pathway for 1-butanol Production in Saccharomyces Cerevisiae", Si et al., Metabolic Engineering, vol. 22, pp. 60-68 (2014).

(56) References Cited

OTHER PUBLICATIONS

"Butanol Production in S. Cerevisiae via a Synthetic ABE Pathway is Enhanced by Specific Metabolic Engineering and Butanol Resistance", Swidah et al., Biotechnology for Biofuels, vol. 8, p. 97 (2015).

"Enhanced Butanol Production by Eukaryotic Saccharomyces Cerevisiae Engineered to Contain an Improved Pathway", Sakuragi et al., Bioscience Biotechnology and Biochemistry, vol. 79, pp. 314-320 (2015).

"Surface Modification by Nonthermal Plasma Induced by Using Magnetic-field-assisted Gliding Arc Discharge", Feng et al., Applied Physics Letters, vol. 101, Issue 4 (2012).

"Sterilization and plasma processing of room temperature surfaces with a one atmosphere uniform glow discharge plasma (OAUGDP)", Gadri et al., Surface and Coatings Technology, vol. 131, Issues 1-3, pp. 528-541 (Sep. 1, 2000).

"Room-temperature atmospheric pressure plasma plume for biomedical applications", Laroussi et al. Applied Physics Letters, vol. 87 (2005).

Abstract of "An overview of research using the one atmosphere uniform glow discharge plasma (OAUGDP) for sterilization of surfaces and materials", Montie et al., Plasma Science, IEEE Transactions, vol. 28, Issue 1, pp. 41-50 (2000).

"Burn Wound Healing: A Role for Plasma Medicine?", Middlekoop E. et al., 4th International Conference on Plasma Medicine, Oral Contributions, Invited Talk, p. 4, Orleans, France (Jun. 17, 2012).

"Stimulation of wound healing by helium atmospheric pressure plasma treatment", Nastuta A. V. et al., Journal of Physics D: Applied Physics, vol. 44, No. 10, IOP Publishing Ltd. (Feb. 21, 2011).

"Mussel-Inspired Surface Chemistry for Multifunctional Coatings", Lee H. et al., Science, vol. 318, No. 5849, pp. 426-430 (Oct. 19, 2007).

"Treatment of Streptococcus mutans biofilms with a nonthermal atmospheric plasma", Sladek R.E.J. et al., Letters in Applied Microbiology, vol. 45, Issue 3, pp. 318-323 (Oct. 2007).

"Plasma needle: a non-destructive atmospheric plasma source for fine surface treatment of (bio)materials", Stoffels E. et al., Plasma Sources Science and Technology, Institute of Physics Publishing, vol. 11, pp. 383-388, (Aug. 30, 2002).

"Plasma interaction with Microbes", Laroussi M. et al., New Journal of Physics, An Institute of Physics and Deutsche Physikalische Gesellschaft Journal, vol. 5, Issue 41.1-41.10 (Apr. 30, 2003).

"Inactivation of E. coli 0157:1-17 Using a Pulsed Nonthermal Plasma System", Montenegro J. et al., Journal of Food Science, vol. 67, Issue 2, pp. 646-648, Wiley Online Library (Mar. 2002).

"Plasma needle for in vivo medical treatment: recent developments and perspectives", Stoffels E et al., Plasma Sources Science and Technology, Institute of Physics Publishing, vol. 15, pp. S169-S180, (Oct. 6, 2006).

"Filamentary and Homogeneous Modes of Dielectric Barrier Discharge (DBD) in Air: Investigation through Plasma Characterization and Simulation of Surface Irradiation", Rajasekaran P. et al., Plasma Process and Polymers, vol. 1, Issue 8, pp. 665-675 (Aug. 2010).

Abstract of "Discharge plasmas generated by piezoelectric transformers and their applications", Itoh H. et al., Plasma Sources Science and Technology, IOP Publishing Ltd, vol. 15, No. 2 (Apr. 24, 2006).

"Mechanism of killing of microorganisms by a one atmosphere uniform glow discharge plasma", Kelly-Wintenberg K. et al., Plasma Science, ICOPS '99—IEEE Conference Record—Abstracts, Monterey, CA, USA (Jun. 24, 1999).

"Spectroscopy of a ferroelectric plasma cathode", Dunaevsky A. et al., Journal of Applied Physics, vol. 90, No. 8, American Institute of Physics (Oct. 15, 2001).

"Influence of Ferroelectric Materials and Catalysts on the Performance of Non-Thermal Plasma (NTP) for the Removal of Air Pollutants", Holzer F. et al., Plasma Chemistry and Plasma Processing, vol. 25, Issue 6, pp. 595-611 (Dec. 2005).

"Atmospheric Non-Thermal Plasma Sources", Nehra V. et al., International Journal of Engineering (IJE), CSC Journals Kuala Lumpur, Malaysia, vol. 2, Issue 1, pp. 53-68, (Feb. 2008).

"IEEE Standard on Magnetostrictive Materials: Piezomagnetic Nomenclature", The Institute of Electrical and Electronics Engineers, Inc., ISBN 1-55937-089-0 (1991).

Abstract of "Efficiency of Removing Sulfur Dioxide in the Air by Non-Thermal Plasma Along with the Application of the Magnetic Field", Jingjing L. et al., Plasma Science and Technology, vol. 7, Issue 5, pp. 3073-3077, Oriprobe Information Services Inc. (2005).

"Plasma for Bio-Decontamination, Medicine and Food Security", Zdenko et al., NATO Science for Peace and Security Series A: Chemistry and Biology, ISBN: 978-94-007-2851-6, Springer Science+ Business Media Media B.V., p. 335, (2012).

\* cited by examiner

METHOD FOR CONTROLLING BIOLOGICAL PROCESSES IN MICROORGANISMS

FIELD OF THE INVENTION

The invention relates to the field of non-thermal plasma technology and application. The invention also relates to means and methods for providing biological effects on micro-organisms.

BACKGROUND OF THE INVENTION

Thermal plasmas and lasers have been widely used in medicine to cut tissues through heating. The effects of such thermal plasmas on tissues are non-selective and difficult to control because they occur primarily through transfer of intense heat. In contrast, non-thermal plasma does not produce heat, thus its effects are more selective. Although electrical discharges that generate non-thermal plasma have been known for a long time, their clinical potential has been largely ignored and until recently, applications have been confined to sterilization of inert surfaces or modulation of cell attachment. The exploitation of cold plasma for clinical applications requires the mechanistic understanding of the interaction of non-thermal plasma with living tissues.

US patent application 2010/0130911 describes a plasma source device which provides a reduced pressure in the ionization chamber. This device is adapted for the sterilization of wounds. Patent application WO2005/084569 discloses a disposable gas plasma tissue resurfacing instrument for skin treatment comprising an electromagnetically resonant focusing element. The aforementioned patent applications pertain to treating the tissues on the surface of wounds.

KR patent application 20140002357 discloses a food surface sterilization method using non-thermal plasma. The sterilization method of the present invention selects non-thermal plasma which is suitable for the food group and optimizes the treatment condition, so as to increases the sterilization effect to the microorganism on the surface of food materials or food, and to decompose the residual agricultural chemical components on the surface of the food materials or food. US patent application 2002175068 teaches decontamination of fluids or objects contaminated with chemical or biological agents using a distributed plasma reactor. In this publication, a corona discharge can be generated using very short high voltage pulses (pulsed discharge) produced by a Tesla coil. Another pulsed discharge embodiment incorporates a primary coil surrounding a chamber having a void filled with a plurality of secondary coils. In one embodiment the apparatus comprises a blanket-like structure that is useful for decontaminating a surfaces or decontaminating a fluid passing between spaced-apart bare electrodes. In another embodiment the bare electrodes define an internal treatment volume through which a contaminated fluid flows.

It has been shown that non-thermal plasma created by dielectric barrier discharge (DBD) has dose-dependent effects on mammalian cells in culture that range from increasing cell proliferation to inducing apoptosis. It has been further shown that these effects are primarily due to the formation of intracellular reactive oxygen species (ROS), which are known to cause DNA damage (S. Kalghatgi, C. Kelly, E. Cerchar, A. Fridman, G. Friedman, J. Azizkhan-Clifford, Effects of Non-Thermal Plasma on Mammalian Cells *PLoS ONE*, 21 Jan. 2011. 6(1)). US patent application 2010/0145253 relates to application of plasma to living tissue in vitro. Thus means and methods for inducing biological and/or biochemical effects on a whole subject, in vivo, using non thermal gas plasma treatment are still required.

The influence of plasma treatment on seed germination has been studied (I. Filatova et al. The effect of plasma treatment of seeds of some grain and legumes, on their sowing quality and productivity, *Rom. Journ. Phys.* Vol. 56, 139-143, 2011; S. Bozena et al, Influence of plasma treatment on wheat and oat germination, *IEEE Transactions on plasma science*, vol. 38, 2010). These studies describe an apparatus comprising a vacuum chamber, a rotary pump and a microwave resonator. The exposure time to the plasma treatment was for a period of several minutes to more than 40 min. Furthermore, the effects reported by these studies mainly relate to the seed coat surface and seed coat sterilization.

The publication of Park et al. (2012) *Analysis of the biological effects of a non-thermal plasma on Saccharomyces cerevisiae, Journal of the Korean Physical Society* Vol. 60 pp. 916-920 teaches the cellular and the molecular responses of eukaryotic yeast to a non-thermal plasma at atmospheric pressure. It was shown that when yeast cells are exposed to a DBD plasma, the number of surviving cells is reduced by more than 50%. It was further demonstrated in this publication that the protein profile of the yeast treated with the plasma exposure was affected by the plasma treatment, relative to control yeast.

Several publications teach the enhanced production of butanol by engineered *Saccharomyces cerevisiae*. Steen et al (2008) *Metabolic engineering of Saccharomyces cerevisiae for the production of n-butanol, Microbial Cell Factories* Vol. 7, pp. 36 discloses *Saccharomyces cerevisiae* engineered with an n-butanol biosynthetic pathway showing an improved production of n-butanol by ten-fold relative to a control. Si et al (2014) *Utilizing an endogenous pathway for 1-butanol production in Saccharomyces cerevisiae, Metabolic Engineering* Vol. 22 pp. 60-68 reports the improved accumulation of butanol of engineered endogenous 1-butanol pathway *Saccharomyces cerevisiae*. Swidah et al. (2015) *Butanol production in S. cerevisiae via a synthetic ABE pathway is enhanced by specific metabolic engineering and butanol resistance, Biotechnology for Biofuels,* Vol. 8 pp. 97 reports that appreciable levels of n-butanol can be achieved in *S. cerevisiae* by transplanting an n-butanol synthesis pathway from *Clostridial* sp. into the genome of *S. cerevisiae* strain. Sakuragi et al. (2015) *Enhanced butanol production by eukaryotic Saccharomyces cerevisiae engineered to contain an improved pathway Bioscience Biotechnology and Biochemistry* Vol. 79, pp. 314-320 teaches the introduction of the butanol production pathway of *Clostridium acetobutylicum* into yeast *Saccharomyces cerevisiae*. It was reported that the elimination of glycerol production pathway in the yeast contributed to the enhancement of 1-butanol production. In addition, by the use of trans-enoyl-CoA reductase in the engineered pathway, 1-butanol production was markedly enhanced.

There is therefore a long felt and unmet need to provide systems and methods for inducing biological and or biochemical effects on a subject, using efficacious non thermal gas plasma treatments and protocols.

SUMMARY OF THE INVENTION

The present invention relates to the field of non-thermal plasma technology and application. In particular, the invention relates to means and methods for inducing therapeutic or regenerative or biochemical effects or beneficial effects on living tissues, micro-organisms, and fluid, emulsions, and gas media.

It is thus one object of the present invention to disclose a method for providing at least one biological effect in at least one microorganism, wherein said method comprises steps of: (a) providing a system for administering modified plasma. The system comprises: (i) a non-thermal plasma (NTP) emitting source for emitting a NTP beam; (ii) a plasma coupling mechanism (PCM), said PCM comprises a plasma beam dish having at least one opening for the passage of said NTP beam; said plasma beam dish having a first surface and a second opposite surface; said first surface of said plasma beam dish is mounted with at least one coupling element selected from a group consisting of: 1. at least one ferroelectric element for providing a ferroelectric induced field for coupling with said NTP beam; 2. at least one ferromagnetic element for providing a ferromagnetic induced field for coupling with said NTP beam; 3. at least one piezoelectric element for providing a piezoelectric induced field for coupling with said NTP beam; and 4. at least one piezomagnetic element for providing a piezomagnetic induced field for coupling with said NTP beam; further said system additionally comprises at least one reflecting element configured to focus said NTP beam thereby generating modified plasma beam; (b) providing a substrate hosting said at least one microorganism; and, (c) administering said generated modified plasma beam in a predetermined pulsed manner to said at least one microorganism hosted in said substrate to provide said at least one biological effect in said at least one microorganism.

It is another object of the present invention to disclose the method as defined above, wherein said substrate is selected from the group consisting of: food, liquid, beverage, suspension, biological culture, medium, growth medium, emulsion, biological tissue, biological organism, human, animal, plant, fluid, soil, minerals, media, gas, gas and liquid mixtures, gas mixtures, cells, tissue culture, organs and any combination thereof.

It is another object of the present invention to disclose the method as defined in any of the above, wherein said microorganism is selected from the group consisting of: yeast, bacteria, archaea, algae, corynebacteria, aerobic bacteria anaerobic bacteria, fungi, protozoa, virus, spores, phyrhv, hypha, *Candida*, prion, and any combination thereof.

It is another object of the present invention to disclose the method as defined in any of the above, wherein said bacteria is selected from the group consisting of *Listeria monocytogenes, Escherichia coli, Salmonella*, bacteria of the Enterobacteriaceae family, bacteria of the Listeriaceae family, gram positive bacteria, gram negative bacteria, anaerobic bacteria, aerobic bacteria, *Staphylococcus aureus, Pseudomonas aeruginosa, Staphylococcus epidermidis, Staphylococcus haemolyticus, enterococcus faecalis, Clostridiaceae family, Clostridium, Corynebacterium*, actinobacteria and any combination thereof.

It is another object of the present invention to disclose the method as defined in any of the above, additionally comprises steps of providing said at least one biological effect up to 6 hours from said administration of said modified plasma beam.

It is another object of the present invention to disclose the method as defined in any of the above, additionally comprises steps of comparing the level of said at least one biological effect to the level of said effect in a control microorganism.

It is another object of the present invention to disclose the method as defined in any of the above, wherein said at least one biological effect is selected from the group consisting of: activation effect, inactivation effect, metabolic effect, anabolic effect, amphibolic effect, regeneration effect, renewable effect, effect on a biochemical pathway, effect on the production of at least one biochemical compound, catabolic effect, anabolic effect, sterilization, antibacterial effect, deactivation effect, survival effect, sterilization effect, infertility effect, loss of viability effect, killing effect, destruction effect, induction effect, destruction of pathogens effect, bacterial destruction effect, viruses destruction effect, genetic effect, water or gas disinfection effect, effect on water or gas contamination parameters, effect on chemical composition, bacteria concentration, phenol concentration, effect on chemical composition of raw oil, effect on raw oil components and concentration, effect on biofuel or biodiesel compounds production and/or destruction, and any combination thereof.

It is another object of the present invention to disclose the method as defined in any of the above, wherein said method provides an effect on enhancing production of at least one biochemical compound in said at least one microorganism.

It is another object of the present invention to disclose the method as defined in any of the above, additionally comprises steps of harvesting said at least one biochemical compound.

It is another object of the present invention to disclose the method as defined in any of the above, additionally comprises steps of selecting said biochemical compound from the group consisting of biofuel and/or products thereof, biodiesel and/or products thereof, organic compounds, metabolic compounds, metabolites, antibiotics, prodrugs, fermentation products, acid compounds, gas compounds, alcohol compounds, precursors of amino acids, and any combination thereof.

It is another object of the present invention to disclose the method as defined in any of the above, additionally comprises steps of selecting said biochemical compound from the group consisting of ethanol, 1-propanol, 2-propanol, 2,3-butanedione, vicinal diketone, acetoin, acetone, 2,3-butanediole, methanol, Isobutanol, butanol, 1-butanol, n-butanol, propandiol, diesel, any isomer or racemic compound thereof, any intermediate pathway compound or precursor thereof, and any mixture thereof.

It is another object of the present invention to disclose the method as defined in any of the above, additionally comprises steps of inducing the production of said at least one biochemical compound to a concentration of between about 5 mg/l to about 200 mg/l or more.

It is another object of the present invention to disclose the method as defined in any of the above, wherein said method provides an effect selected from the group consisting of antimicrobial, sterilization, killing, deactivation, infertilization, inactivation, disinfection, and any combination thereof of said at least one microorganism.

It is another object of the present invention to disclose the method as defined in any of the above, additionally comprises steps of providing said at least one biological effect in said at least one microorganism without significantly altering the pH or Hydrogen peroxide concentration or a combination thereof of said substrate hosting said at least one microorganism.

It is another object of the present invention to disclose a system for administering modified plasma to a substrate hosting at least one microorganism. The system comprises: (a) a non-thermal plasma (NTP) emitting source for emitting a NTP beam; and (b) a plasma coupling mechanism (PCM), wherein said PCM comprises a plasma beam dish having at least one opening for passage of said NTP beam; said plasma beam dish having a first surface and a second opposite surface; said first surface of said plasma beam dish comprises at least one coupling element selected from a group consisting of:

1. at least one ferroelectric element for providing a ferroelectric induced field for coupling with said NTP beam;
2. at least one ferromagnetic element for providing a ferromagnetic induced field for coupling with said NTP beam;
3. at least one piezoelectric element for providing a piezoelectric induced field for coupling with said NTP beam; and
4. at least one piezomagnetic element for providing a piezomagnetic induced field for coupling with said NTP beam;

wherein said system additionally comprises at least one reflecting element configured to focus said plasma beam, thereby providing said modified plasma in a predetermined pulsed manner, further wherein said system provides at least one biological effect to said at least one microorganism.

It is another object of the present invention to disclose the system as defined above, wherein said NTP emitting source is selected from the group consisting of a dielectric barrier discharger, an atmospheric pressure glow discharger, a corona plasma discharger, a high voltage DC corona discharger, a high voltage negative DC corona discharger, a high voltage positive DC corona discharger, a floating electrode dielectric barrier discharger, gliding arc discharge (GD) induced plasma and a plasma jet.

It is another object of the present invention to disclose the system as defined in any of the above, wherein said at least one coupling element at least partially comprises Polyvinylidene fluoride, polyvinylidene difluoride (PVDF), PZT, lead zirconium titanate, ferroelectric oxides, Pb[Zr(x)Ti(1−x)]O3, PbZrO3, PbTiO$_3$, Barium Titanate (BaTiO3), (Ba, Sr)TiO3, Ba(1−x) Sr(x)TiO3, a ferroelectric material characterized by at least one of piezoelectricity, pyroelectricity and memory properties, a permanent magnet, an electromagnet, a superconducting magnet, Cobalt, Magnetite (Fe3O4), α-ferrite (α Fe), iron, ferromagnetic alloys, piezomagnetic ferrite materials, magnetoelectric ceramic materials and any combination thereof.

It is another object of the present invention to disclose the system as defined in any of the above, wherein said at least one reflecting element at least partially comprises a material or element selected from the group consisting of: a reflector coating, metals, iron, metal alloys, stainless steel, aluminum, silver, gold and mixtures thereof, dielectric coating, ultraviolet coating, UV reflecting materials, 100-280 nm reflecting materials, glass, amorphous materials, solid materials, insoluble materials, crystalline materials polymers and any combination thereof.

It is another object of the present invention to disclose the system as defined in any of the above, wherein said at least one coupling element is arranged in at least one set of pairs or triplicates or in at least one set of more than three coupling elements.

It is another object of the present invention to disclose the system as defined in any of the above, wherein said modified plasma is characterized by at least one parameter selected from the group consisting of: a dose range of between about 0.1 J/cm2 to about 4 J/cm2, a frequency range of between about 100 Hz and about 20 MHz, a relative dielectric constant in the range of between about 500 and about 2500, a piezoelectric charge constant in the range of between about 100 (10-12 C/N or 10-12 m/V) to about 1000 (10-12 C/N or 10-12 m/V), a piezoelectric voltage constant in the range of between about 5 (10-3 Vm/N or 10-3 m2/C) to about 50 (10-3 Vm/N or 10-3 m2/C), frequency constants in the range of between about 1000 (Hz·m or m/s) to about 5000 (Hz·m or m/s) and any combination thereof.

It is another object of the present invention to disclose the system as defined in any of the above, wherein said modified plasma is adapted to provide at least one biological or biochemical effect selected from the group consisting of: at least one brain related parameter, protein fingerprint or profile, enzymatic activity, protein crystallization, metabolic activity, at least one medical or therapeutic effect, at least one plant parameter, at least one water parameters, at least one air pollution parameter, at least one fluid or gas parameter, at least one oil or raw oil parameter, treatment of gaseous emissions, ozone treatment, increased functional recovery after a disruptive effect, at least one immune system parameter, at least one skin related parameter, at least one food sterilizing parameter, wound healing, recovery from bacterial infection, recovery from viral infection, tissue regeneration, pain relief, antioxidant activity, at least one rheological property, in vivo effect, in vitro effect and any combination thereof.

It is another object of the present invention to disclose the system as defined in any of the above, wherein said at least one biological effect in said at least one microorganism is provided without significantly altering the pH or Hydrogen peroxide concentration or a combination thereof of said substrate hosting said at least one microorganism.

DETAILED DESCRIPTION OF THE FIGURES

In order to better understand the invention and its implementation in practice, a plurality of embodiments will now be described, by way of non-limiting example only, with reference to the accompanying drawings, wherein FIG. 1A-C is presenting in an out-of-scale-manner a schematic illustration of preferred embodiments of the system for the administration of a plasma modified field (PMF) to a subject;

Figures 4A, 4B:
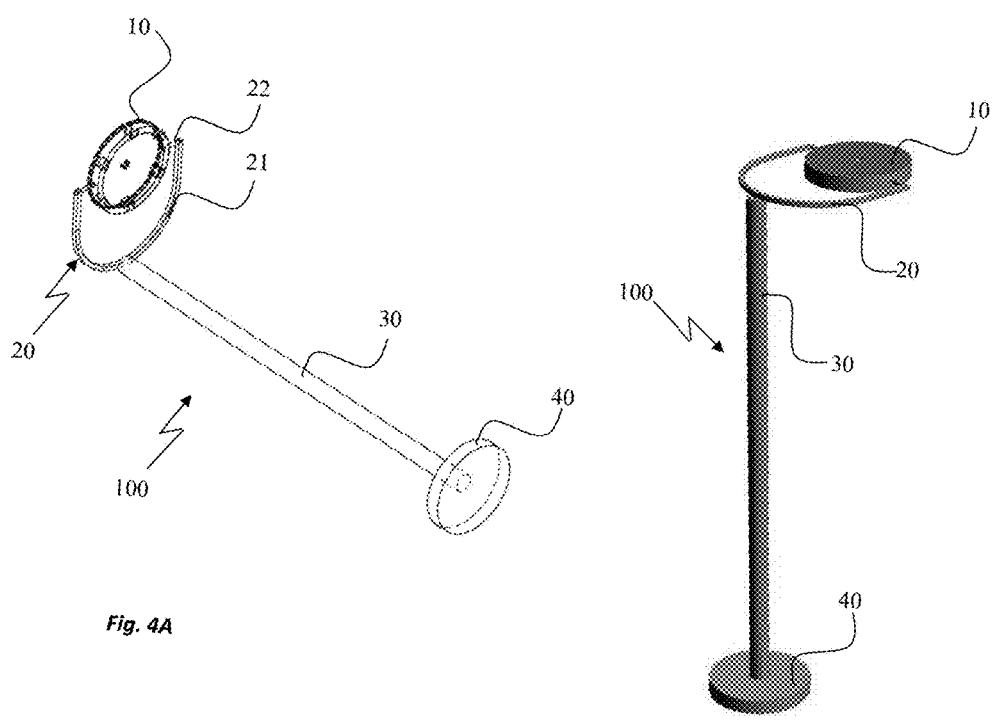
Figure 5A:
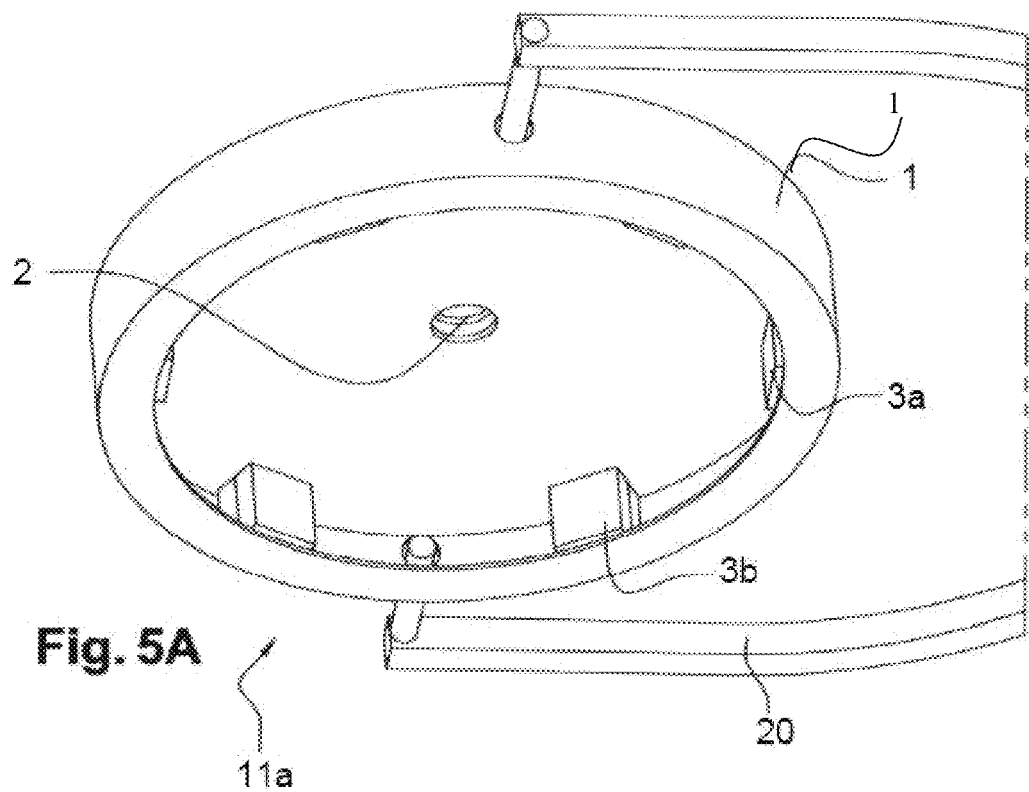
Figure 5B:
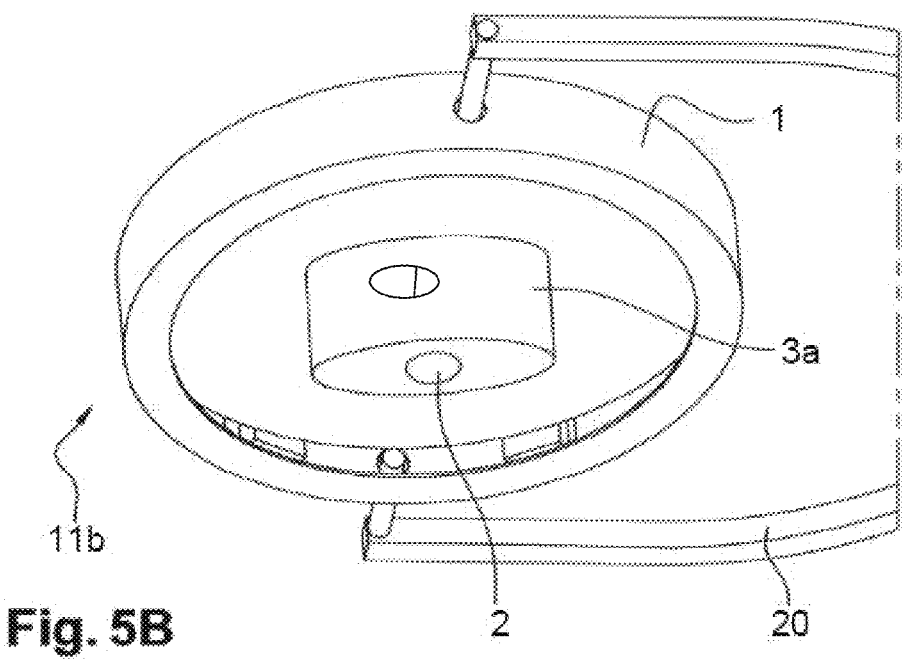
Figure 6:
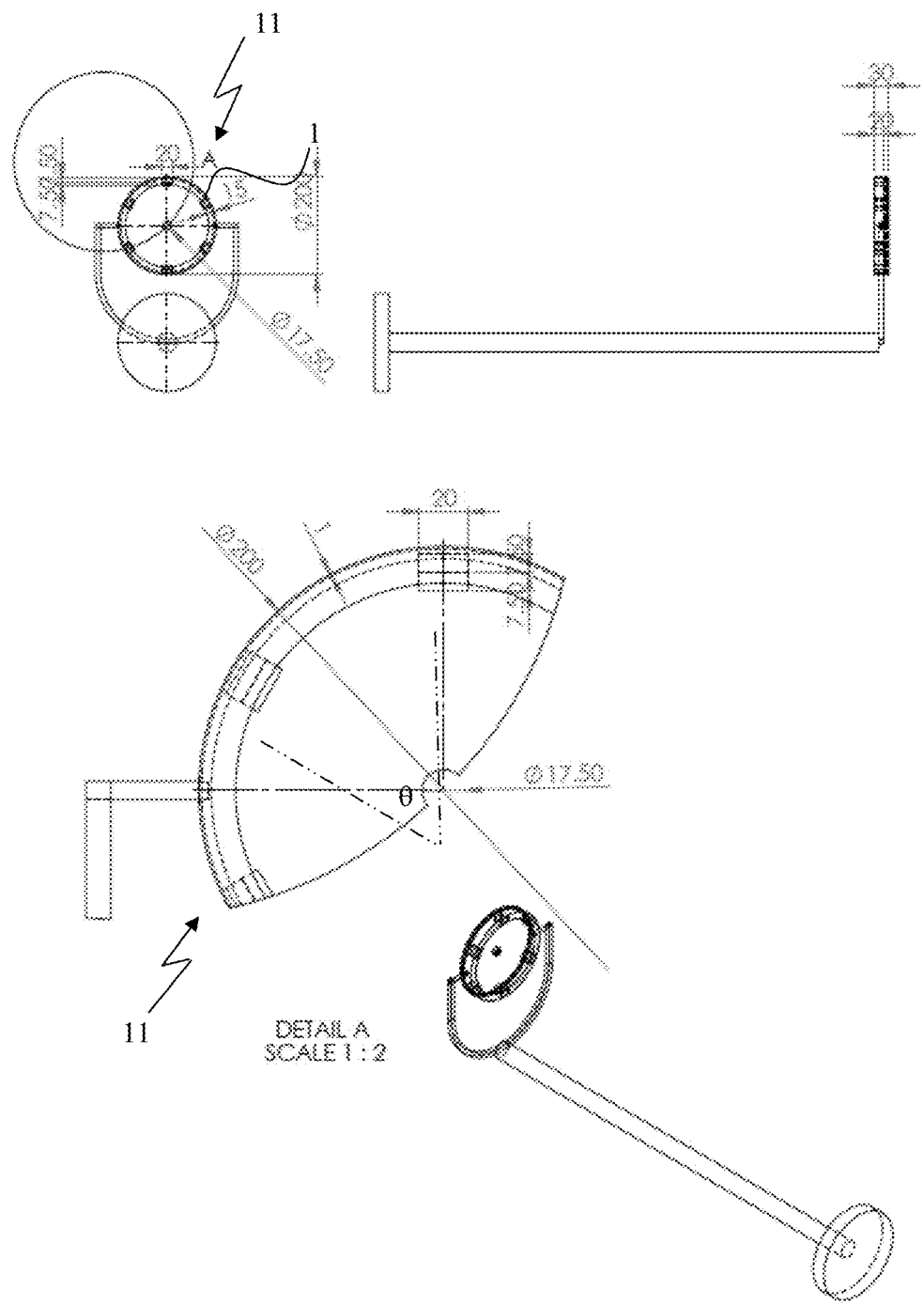
Figure 7A:
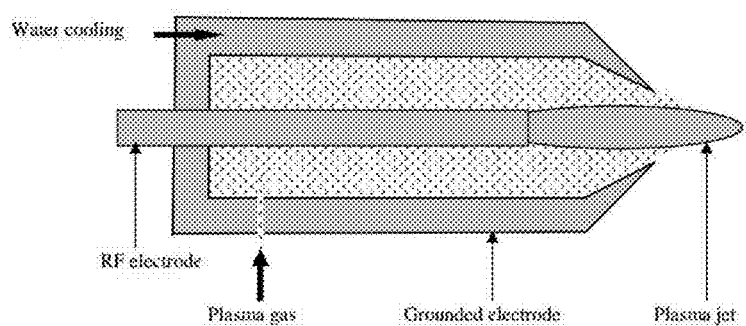
Figure 7B:
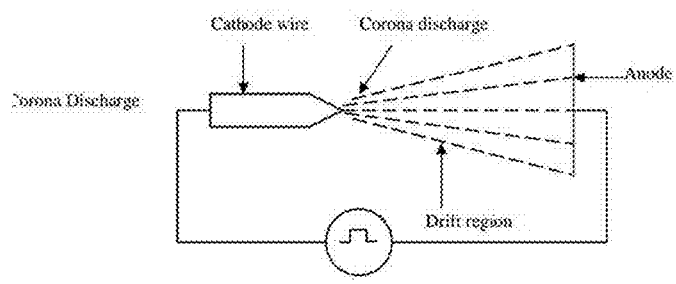
Figure 8:
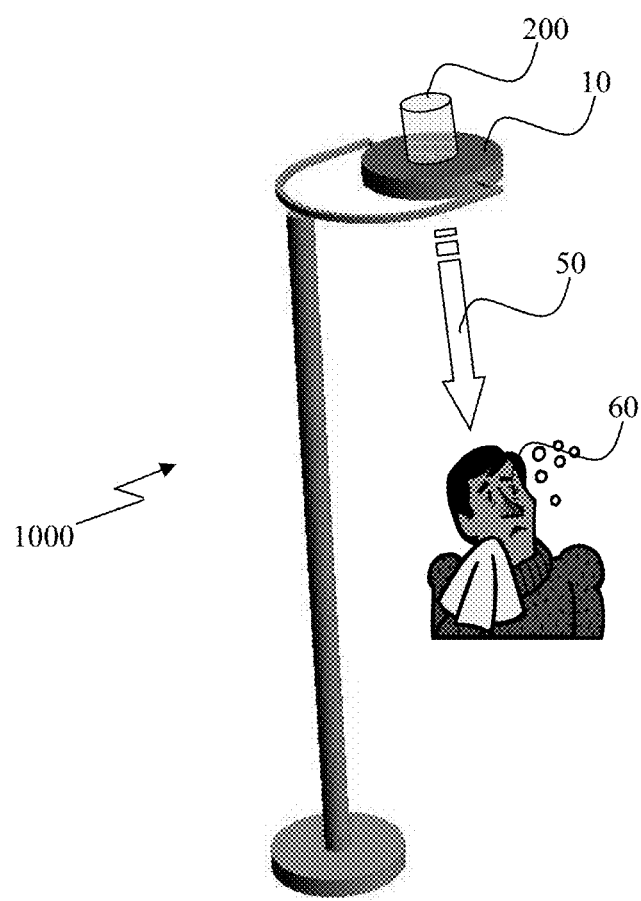
Figure 10A:
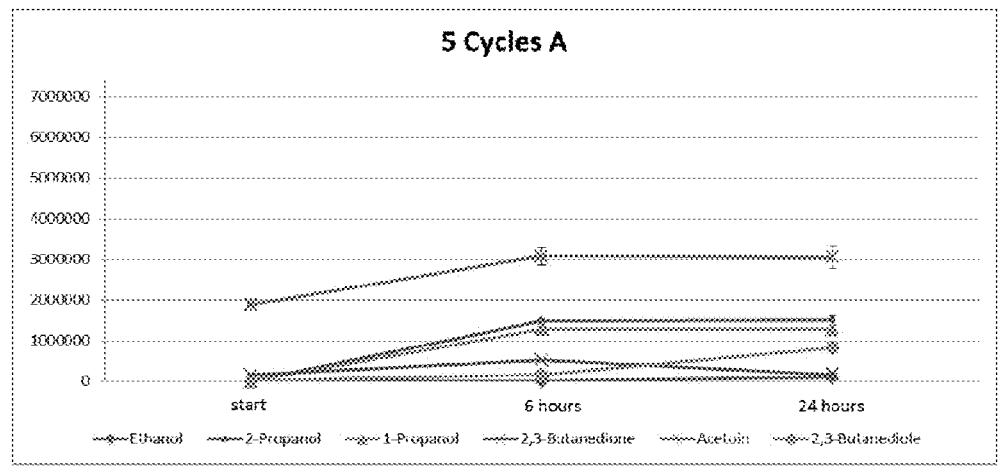
Figure 10B:
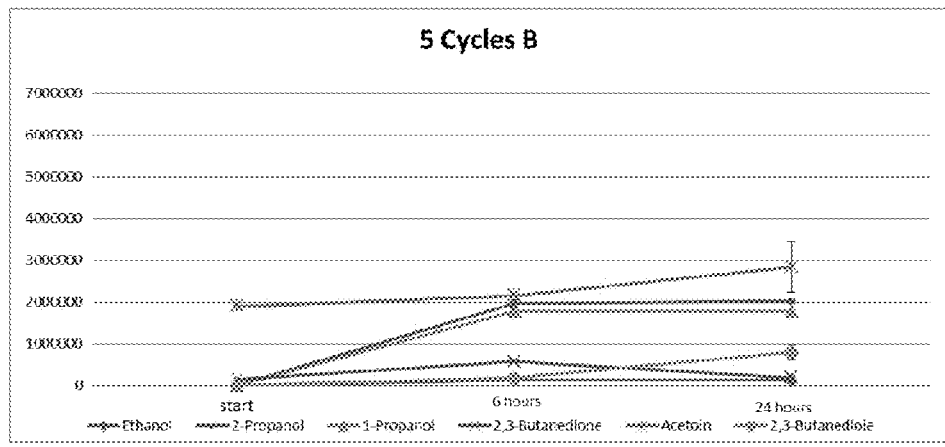
Figure 10C:
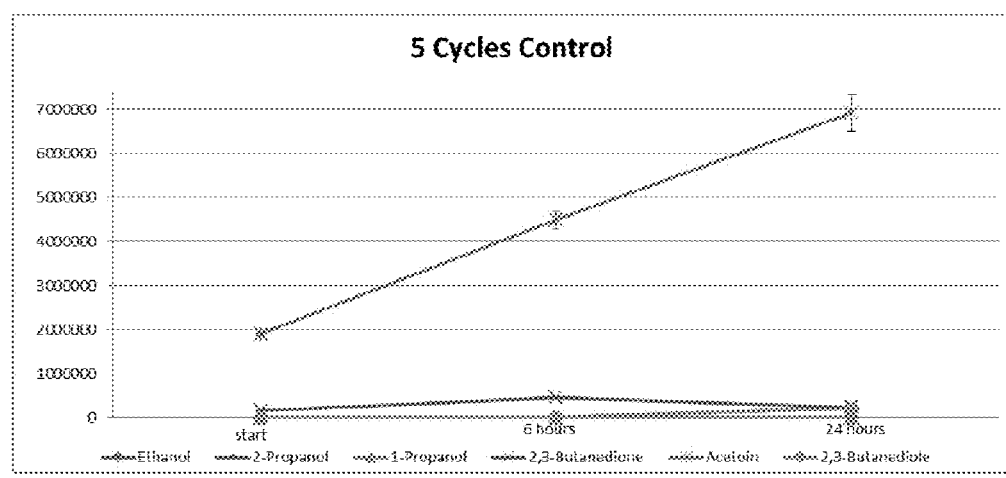
Figure 11A:
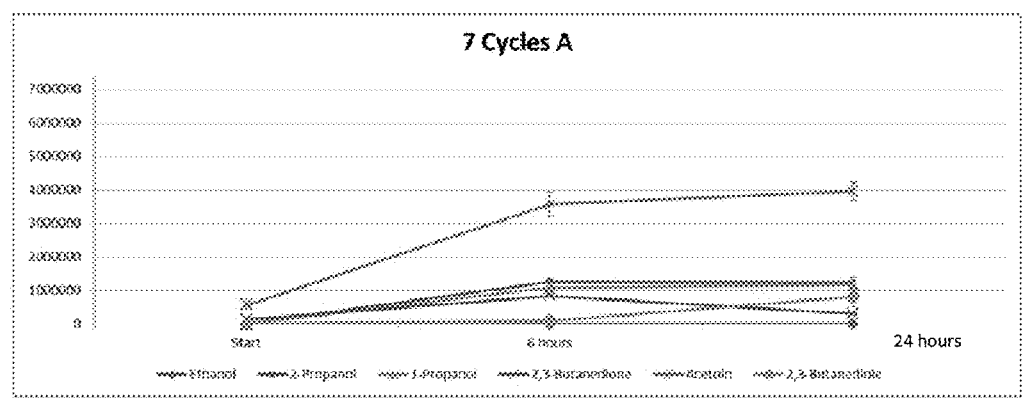
Figure 11B:
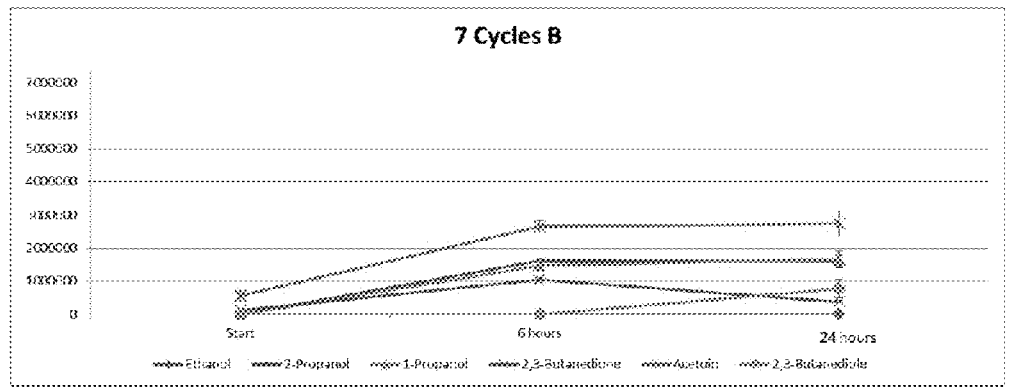
Figure 11C:
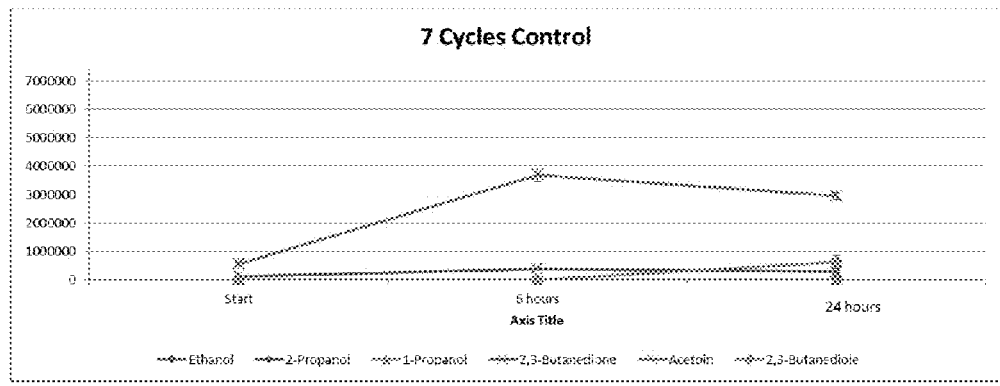
Figure 12A:
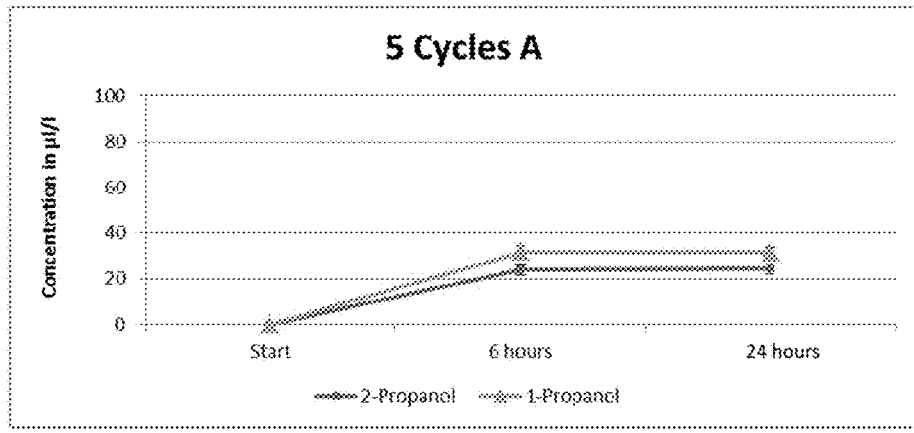
Figure 12B:
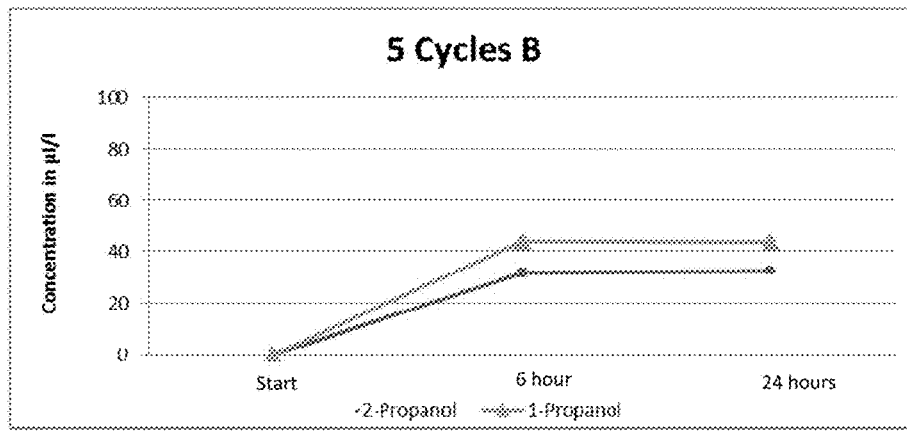
Figure 12C:
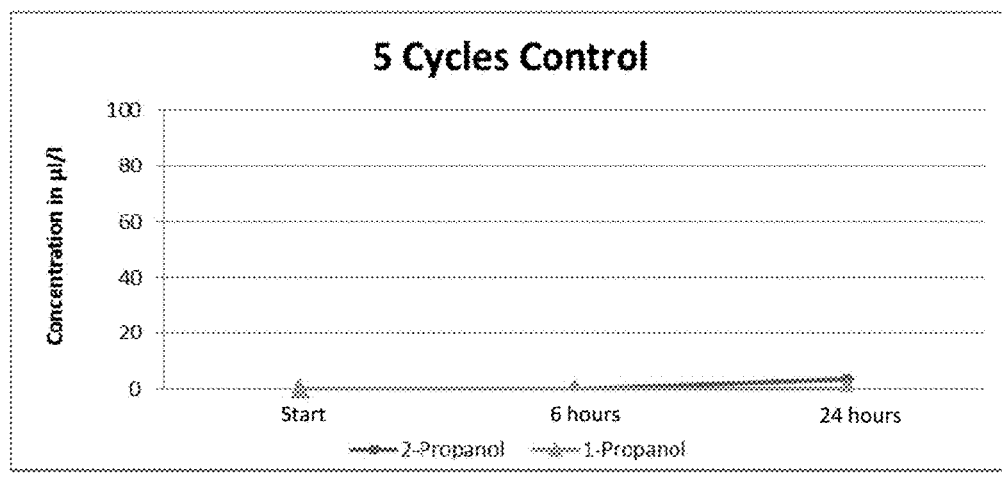
Figure 13A:
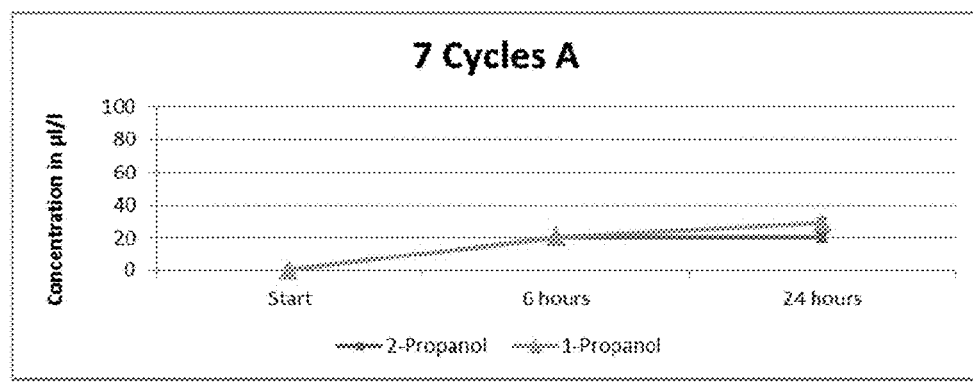
Figure 13B:
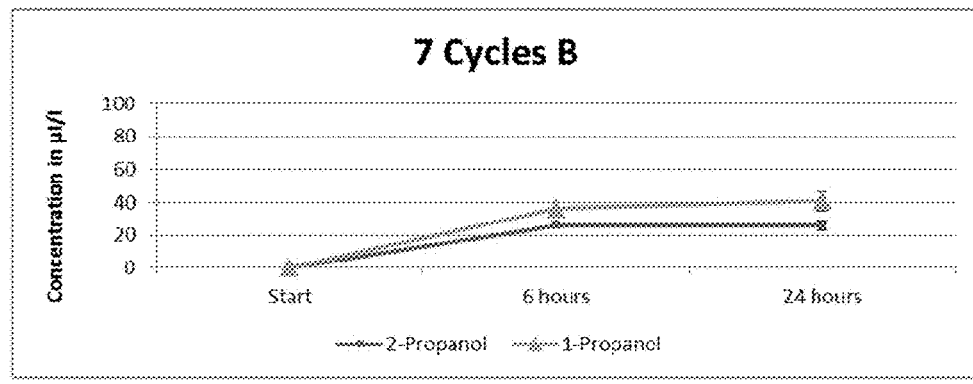
Figure 13C:
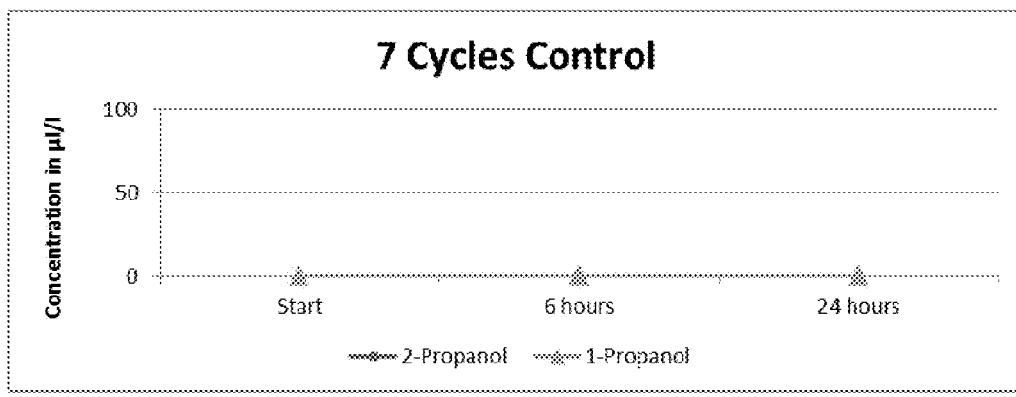

FIGS. 4A and 4B both illustrate in an out-of-scale-manner schematic views of a plasma beam dish (10) and stand thereof (100), FIG. 4A is a side view and FIG. 4B is a perspective view;

FIGS. 5A and 5B are illustrating in an out-of-scale-manner schematic views of a multiple coupling elements plasma beam dish (11a) and a single coupling element plasma dish (11b) as two embodiments of the present invention;

FIG. 6 is illustrating in an out-of-scale-manner schematic views of a plasma beam dish (11) according to a specific embodiment of the invention;

FIG. 7A is illustrating in an out-of-scale-manner a schematic view of an atmospheric pressure plasma jet as an alternative embodiment of the present invention; FIG. 7B is illustrating in an out-of-scale-manner a schematic view of a corona discharger as an alternative embodiment of the present invention;

FIG. 8 is illustrating in an out-of-scale-manner a schematic view of a system for applying modified plasma to a subject (1000) for inducing a biological and/or biochemical effect on the subject; and FIG. 9A-9F is illustrating in an out-of-scale-manner a schematic view of plasma modified field profiles, according to some embodiments of the invention, namely examples of the discharge profiles over time;

FIG. 10 is a graphic illustration of the biochemical compounds produced by S. cerevisiae exposed to one modified plasma treatment of 5 pulse cycles (FIG. 10A) and two modified plasma treatments of 5 pulse cycles (FIG. 10B) as compared to control (non treated) S. cerevisiae (FIG. 10C);

FIG. 11 is a graphic illustration of the biochemical compounds produced by S. cerevisiae exposed to one modified plasma treatment of 7 pulse cycles (FIG. 11A) and two modified plasma treatments of 7 cycles each (FIG. 11B), as compared to control S. cerevisiae (FIG. 11C);

FIG. 12 is a graphic illustration of the concentration of the biochemical compounds produced by S. cerevisiae exposed to one modified plasma treatment of 5 pulse cycles (FIG. 12A) and two modified plasma treatments of 5 pulse cycles each (FIG. 12B), as compared to control S. cerevisiae (FIG. 12C); and FIG. 13 is a graphic illustration of the concentration of the biochemical compounds produced by S. cerevisiae exposed to one modified plasma treatment of 7 pulse cycles (FIG. 13A) and two modified plasma treatments of 7 pulse cycles each (FIG. 13B), as compared to control S. cerevisiae (FIG. 13C).

DETAILED DESCRIPTION OF THE PREFERRED EMBODIMENTS

The following description is provided, alongside all chapters of the present invention, so as to enable any person skilled in the art to make use of said invention and sets forth the best modes contemplated by the inventor of carrying out this invention. Various modifications, however, is adapted to remain apparent to those skilled in the art, since the generic principles of the present invention have been defined specifically to provide means and method for administering a plasma modified field (PMF) to a subject for inducing regenerative or biological or biochemical effects.

According to one embodiment, the present invention provides a method for providing at least one biological effect in at least one microorganism, said method comprises steps of: (a) providing a system for administering modified plasma beam; (b) providing a substrate hosting said at least one microorganism; and (c) administering said generated modified plasma beam in a predetermined pulsed manner to said substrate hosting said at least one microorganism to provide said at least one biological effect to said at least one microorganism. The aforementioned system comprises: (a) a non-thermal plasma (NTP) emitting source for emitting a NTP beam; and (ii) a plasma coupling mechanism (PCM), wherein said PCM comprises a plasma beam dish having at least one opening for the passage of said NTP beam; said plasma beam dish having a first surface and a second opposite surface; said first surface of said plasma beam dish is mounted with at least one coupling element selected from a group consisting of: 1. at least one ferroelectric element for providing a ferroelectric induced field for coupling with said NTP beam; 2. at least one ferromagnetic element for providing a ferromagnetic induced field for coupling with said NTP beam; 3. at least one piezoelectric element for providing a piezoelectric induced field for coupling with said NTP beam; and 4. at least one piezomagnetic element for providing a piezomagnetic induced field for coupling with said NTP beam; further wherein said system additionally comprises at least one reflecting element configured to focus said NTP beam thereby generating modified plasma beam.

According to a further embodiment, the system for administering modified plasma optionally comprises a gas plasma flow regulator or monitoring means configured to control and/or monitor gas plasma flow parameters such as flow rate, flow pressure, mass flow, and gas plasma composition ratios.

In a specific embodiment, the gas plasma discharge comprises a gas mixture combination comprising Argon (Ar), $N_2$ and $O_2$. It is noted that the gas plasma flow regulator or monitoring means is configure to control and/or monitor the gas plasma flow parameters of the gas plasma mixture and of each of it's components or ingredients separately.

Reference is now made to Table 1 presenting optional plasma ingredients combinations (No. 1 to 10) within the scope of the present invention.

TABLE 1

Plasma ingredients % (wt.); R for any material other than Ar, $N_2$ or $O_2$; a, b, c and r refer to % (wt.) of each of the ingredients, respectively.

| No. | Ar | $N_2$ | $O_2$ | R |
|---|---|---|---|---|
| 1 | 80-99 | 0-10 | 0-5 | 0 |
| 2 | 80-95 | 5-12 | 0-4 | 0 |
| 3 | 80-95 | 0-15 | 0-5 | 0 |
| 4 | 80-95 | 0-12 | 0-4 | 0-4 |
| 5 | 90 | 8 | 2 | 0 |
| 6 | 85 | 9 | 6 | 0 |
| 7 | 90 | 6 | 4 | 0 |
| 8 | 95 | 3 | 2 | 0 |
| 9 | 100a<br>a = 0.7-1.3 | 100b<br>b = 0.13-0.06 | 100c<br>b = 0.01-0.03 | 0 |
| 10 | 100a<br>a = 0.6-1.2 | 100b<br>b = 0.075-0.22 | 100c<br>b = 0.005-0.025 | 100r<br>r = 0.005-0.075 |

It is a main aspect that the system and method of the present invention to provide efficacious modified non thermal gas plasma treatments and protocols that can be applied to a predetermined substrate or subject to control and/or enhance biological processes. The biological processes encompass effects on metabolite or biochemical compounds production and effects on microbial inactivation. It is emphasized that the modified plasma treatments and methods of the present invention are highly advantageous over the currently conventionally used methods for controlling biological processes in microorganisms. For example, the modified plasma treatments of the present invention require relatively short administration or exposure time of the substrate hosting the microorganism (between 8 seconds and up to 30 min). Furthermore, the resulted desirable effect is achieved after a relatively short recovery or incubation time (up to 6 or 24 or 48 hours) from the exposure to the modified plasma treatment. In addition, the modified plasma treatment of the present invention is applied without the requirement for engineering, transformation or transplantation processes, and/or without the need for additional materials or pretreatments, and moreover the modified plasma treatments of the present invention can be designed or adjusted for a predefined desirable biological effect and/or predefined microorganism or combination of microorganisms.

It is within the scope of the present invention that by exposing microbes to the modified plasma treatments of the present invention, advanced generation biofuels or products thereof can be effectively produced.

It is herein acknowledged that first- and second-generation biofuels such as ethanol and biodiesel have several inherent limitations and disadvantages that make them significantly less attractive as a long-term replacement for petroleum. For example, the primary feedstocks for first-generation ethanol (corn and sugarcane) and biodiesel (rapeseed, soybeans, and palm) are food-based crops that compete for scarce cropland, fresh water, and fertilizers. Moreover, these fuels cannot be used in unmodified engines above small blends and are not applicable to the jet fuel market.

Therefore the present invention provides advantageous and beneficial next generation (i.e. at least "third-generation" and "fourth-generation") biofuels based on advanced biochemistry, and revolutionary processes. The present invention utilizes novel metabolism and/or fermentation techniques to produce biofuel compounds such as propanol and butanol derivatives using yeast strains.

A feedstock is herein defined as any renewable, biological material or biomass that can be used directly or indirectly as a fuel, or converted to another form of fuel or energy product.

The advanced biofuels of the present invention encompass the various terms or approaches referring to biofuels including: first generation, second generation, third generation, fourth generation, 1G, 2G, 3G, next generation, sustainable, renewable, advanced, green hydrocarbons etc.

It is further acknowledged that the classifications of biofuels are generally based on: type of source; conversion technology used and properties of the fuel molecules produced.

According to other aspects, it is further within the scope that the term advanced biofuels is herein used in a general way to describe:

a. Biofuels produced by advanced processes, i.e. from non-food feedstocks (e.g. microorganisms). The end product may be equivalent to fuels produced by first generation technology (e.g. ethanol or FAME), or may be a different type of advanced biofuel (such as, propanol or butanol). Such "next generation" biofuels are considered more sustainable (may offer greater levels of GHG reduction and do not compete with food crops for land use).

b. Biofuels with improved properties, for example produced from sustainable feedstocks that are not considered to compete adversely with food production systems, or lead to loss of stored carbon through deforestation, may be more compatible with existing fuel infrastructures, enable greenhouse gas emission savings compared to first-generation biofuels or offer other technical benefits.

It is further within the scope that biofuels produced from non-food feedstock or via first generation technology may also be referred to as next generation or sustainable, or sometimes grouped with advanced biofuels, even if no advanced processing technology is used.

It is further noted that other factors relating to land use, competition with food crops, and the efficiency of the production process, total energy balance, etc may be taken into account when referring to advanced biofuels.

The method and system of the present invention is designed and developed to meet and achieve sustainability and/or fuel quality standards, as well as the needs of renewability.

According to another embodiment, the present invention provides a system for the administration of a plasma modified field (PMF) to a subject. The aforementioned system comprising: (a) a non-thermal plasma (NTP) emitting source for emitting a plasma beam; (b) a plasma modified field coupling mechanism (PMFCM) and (c) a controller for controlling said PMFCM. According to main aspects, the PMFCM comprises a plasma beam dish having at least one opening for the passage of said plasma beam; said plasma beam dish having a first surface and a second opposite surface; wherein the first surface of the plasma beam dish is mounted with: (i) at least one coupling element and (ii) at least one reflecting element. The at least one coupling element is preferably selected from the group consisting of: (1) at least one ferroelectric element for providing the field; (2) at least one ferromagnetic element for providing the field; (3) at least one piezoelectric element for providing the field; (4) at least one piezomagnetic element for providing the field and, any combination thereof. According to a core aspect of the invention, the PMFCM and the controller are configured to adjust any of the at least one coupling and reflecting element in a predetermined manner thereby providing the PMF in a predetermined pulsed manner for inducing a therapeutic or regenerative or biochemical or biological or beneficial effect on the subject or on a substrate hosting at least one microorganism.

It is further within the scope of the invention that the controller is configured to provide pulses of the modified plasma or PMF in a predetermined manner.

It is further within the scope of the invention wherein the unique system of the present invention, unexpectedly provides an effect beneath the outer integument of the treated subject. The relevant prior art relates to experiments showing surface modification (i.e. Feng et al., 2012. Appl. Phys. Lett. 101, 041602), particularly treating superficial wounds on the outer surface of the skin (epidermis) or affecting the seed coat or sterilization of the outer layer of the skin or seed. The present invention is further configured to induce a therapeutic or regenerative or beneficial effect on layers or tissues or regions not limited to the surface of the treated subject, for example affecting enteric diseases, providing an effect on cells or tissues in the brain or providing an effect on wounds penetrating to dipper layers of the skin and body.

It is further within the scope of the invention, wherein the system is adapted to provide a synergic effect with respect to inducing a therapeutic or regenerative or biological or biochemical or beneficial effect on the subject as compared to the effect induced by each of the plasma coupled elements, namely each of the at least one coupling element and at least one reflecting element, individually or in a partial combination administered.

In a further embodiment, the system is adapted to provide a synergic effect of at least about 5% in at least one of the properties of the PMF and/or with respect to inducing a therapeutic or regenerative or biochemical or beneficial effect on the subject as compared to the properties of and/or the effect induced by each of the plasma coupled elements, namely each of the at least one coupling element and at least one reflecting element, individually or in a partial combination administered.

The term "non-thermal plasma" or "non-thermal plasma" or "NTP" generally refers hereinafter to any plasma which is not in thermodynamic equilibrium, either because the ion temperature is different from the electron temperature, or because the velocity distribution of one of the species does not follow a Maxwell-Boltzmann distribution. It is in the scope of the invention wherein the NTP is referred to by the specific technology used to generate it i.e. "gliding arc", "plasma pencil", "plasma needle", "plasma jet", "dielectric barrier discharge", "one atmosphere uniform glow discharge plasma", "atmospheric plasma", "ambient pressure non-thermal discharges", "non-equilibrium atmospheric pressure plasmas"; wherein those terms related to both: non-thermal plasma and plasma operated at or near atmospheric pressure. It is further within the context of the present invention that the term further refers to "cold" plasma defined as the one-atmosphere, near room temperature plasma discharges, which is distinguished from other plasmas, operating at hundreds or thousands of degrees above ambient.

It is further in the scope of the invention, wherein the generated plasma is selected from a group consisting of positive ions, negative ions, electrons metastables, atoms, free radicals and photons.

According to certain embodiments, the NTP emitting source is selected from the group consisting of a dielectric barrier discharger, an atmospheric pressure glow discharger, a corona plasma discharger, a high voltage DC corona discharger, a high voltage negative DC corona discharger, a high voltage positive DC corona discharger, a floating electrode dielectric barrier discharger, gliding arc discharge (GD) induced plasma and a plasma jet. The term "dish" used herein generally refers to an article or element or object, preferably having a rounded-like or circular-like shape, such as a ring or a disk.

As used herein the term "about" denotes ±25% of the defined amount or measure or value.

The term "subject" as used herein refers to human, animal, plant, flatworms, micro-organisms, planaria, fluids, emulsions, soil, minerals, media, gas and liquid and gas mixtures and/or to an object.

The term "substrate" as used herein refers to food or food product, liquid, beverage, suspension, biological culture, medium, growth medium, emulsion, biological tissue, biological organism, human, animal, plant, fluid, soil, minerals, media, gas, gas and liquid mixtures, gas mixtures, cells, tissue culture, organs and any combination thereof.

The term "microorganism" as used herein generally refers to a microscopic living organism, which may be single celled or multicellular. It is within the scope that microorganisms include yeast, bacteria, archaea, algae, corynebacteria, aerobic bacteria anaerobic bacteria, fungi, protozoa, virus, spores, phyrhv, hypha, *Candida*, prion, and any combination thereof. In specific embodiments, it includes industrial microorganisms, which refer to types of microorganisms such as bacteria and yeast that are used for large-scale production of industrial items. Industrial microbiology includes the use of microorganisms to manufacture food or industrial products in large quantities. Numerous microorganisms are used within industrial microbiology; including naturally occurring organisms, selected mutants or otherwise treated micro-organisms or genetically modified organisms (GMOs).

Non limiting examples of bacteria included within the scope of the present invention are *Listeria monocytogenes, Escherichia coli, Salmonella*, bacteria of the Enterobacteriaceae family, bacteria of the Listeriaceae family, gram positive bacteria, gram negative bacteria, anaerobic bacteria, aerobic bacteria, *Staphylococcus aureus, Pseudomonas aeruginosa, Staphylococcus epidermidis, Staphylococcus haemolyticus, enterococcus faecalis*, Clostridiaceae family, *Clostridium, Corynebacterium*, actinobacteria and any combination thereof.

The term "plasma modified field" or "PMF" or "modified plasma" or "modified plasma beam" as used herein refers to a plasma or plasma beam coupled to, or modified, or transformed by, or generated by, at least one of ferroelectric means or elements, ferromagnetic means or elements, piezoelectric means or elements or by a combination of all elements or any partial combination thereof. According to a main embodiment, the plasma is further adjusted or influenced by a reflecting element as inter alia disclosed. It is within the scope of the present invention that a "modified plasma" or "modified plasma beam" or "plasma modified field" or "PMF" refers to plasma oscillations influenced by a coupling element selected from the group consisting of at least one ferroelectric element, at least one ferromagnetic element, at least one piezoelectric element or by any combination thereof, as well as by a reflecting element. The modified plasma or modified plasma beam is applied to a subject in a predetermined pulsed manner to induce a biological or renewable or regenerative or beneficial effect.

In one embodiment, the modified plasma or PMF is applied to the subject in a predetermined mode, particularly pulse mode, which is determined or more specifically adjusted according to the classification (i.e. taxonomic classification) of the treated subject or according to the desirable effect (e.g. microbial inactivation or biochemical production). For example, a PMF pulse profile designed to induce a regenerative or a biochemical effect or beneficial effect in a plant may be different (i.e. by pulse duration, pulse rate pulse intervals, pulse cycle profile or any combination thereof) from the PMF pulse profile designed to induce a therapeutic or regenerative or a biochemical processes or a beneficial effect in human and/or from the PMF pulse profile designed to induce a beneficial effect on water or to produce/control biochemical processes in bacteria, or yeast, or viruses, or fungi. Example of pulse profiles or cycles or patterns or parameters included within the scope of the present invention are provided in FIG. 9 and Table 3.

The term "plasma coupling mechanism" or "PCM" or "plasma modified field coupling mechanism" or "PMFCM" relates to a mechanism that is positioned distally or remotely or externally to the NTP source and is configured and designed to affect or influence or modify the plasma beam emitted from the NTP source. It is within the scope of the invention that the plasma coupling mechanism comprises the at least one coupling element and the at least one reflecting element in various configurations and arrangements.

The term "coupling element" as used herein refers to means including a material or a substance or a component or a pattern that is used to provide the modified plasma or PMF. In some embodiments, the coupling element is configured to provide electromagnetic and/or ferroelectric and/or ferromagnetic induced field. In preferred embodiments, the coupling element is selected from the group consisting of (1) at least one ferroelectric element; (2) at least one ferromagnetic element; (3) at least one piezoelectric element; (4) at least one piezomagnetic element and any combination thereof. According to certain embodiments, such coupling element or any combination of the aforementioned coupling elements are used as part of the system for the administration of a plasma modified field (PMF) to a subject to induce a therapeutic or regenerative or biological or beneficial effect on said subject. The at least one coupling element is designed to provide an electric and/or magnetic field.

The term "ferromagnetic element" used herein refers to an element comprising a material which exhibit ferromagnetism in the broad sense that includes ferrimagnetism. According to certain aspects, the ferromagnetic element is selected from the group consisting of a permanent magnet, an electromagnet, a superconducting magnet, and any combination thereof.

It is within the scope of the invention that such materials include elemental metals, and in other embodiments include alloys, oxides or other chemical compounds or mixtures thereof. Non limiting examples of Ferromagnetic materials include Chromium(IV) oxide, Cobalt, Dysprosium, Ferrite (iron), Ferrite (magnet), Magnetite ($Fe_3O_4$), α-ferrite (α Fe), Gadolinium, Gallium manganese arsenide, Iron, Neodymium magnet, Nickel, Permalloy, Rare-earth magnet, Samarium-cobalt magnet, Suessite, Yttrium iron garnet, ferromagnetic alloys, and any combination thereof.

The term "ferroelectric element" used herein generally refers to a material having a property of a spontaneous electric polarization that can be reversed by the application of an external electric field. In other words, ferroelectric materials refer to materials that maintain a permanent electric polarization that can be reversed, or switched, in an external electric field. In specific embodiments, ferroelectric materials are pyroelectric and inherently piezoelectric. In certain embodiments, ferroelectric capacitors may have the combined properties of memory, piezoelectricity, and pyroelectricity. According to some aspects, piezoelectricity generally refers to the generation of a surface charge in response to the application of an external stress to a material. According to further aspects, pyroelectricity generally refers to a change in the spontaneous polarization of a material in response to a change in temperature.

It is within the scope of the present invention that ferroelectric materials and/or elements include ferroelectric polymers, particularly polyvinylidene fluoride, or polyvinylidene difluoride (PVDF). In alternative embodiments, ferroelectric elements included within the scope of the present invention may at least partially comprise PZT, lead zirconium titanate, ferroelectric oxides, $Pb[Zr(x)Ti(1-x)]O_3$, $PbZrO_3$, Barium Titanate ($BaTiO_3$), $(Ba, Sr)TiO_3$, $Ba(1-x) Sr(x)TiO_3$ and any combination thereof.

The term "piezoelectric element" used herein generally refers to materials or certain crystals having the ability to generate a voltage in response to applied mechanical stress. PZT (lead-zirconia-titanate) is one of a large family of materials, whose structure change on the application of an electric current or, when strained, generate electricity. These specific piezo or ferroelectric effects have the properties that when a current is applied, a volume change occurs in the material.

Thus it is herein acknowledged that according to one embodiment, an important ferroelectric material is lead zirconate titanate (PZT), which is part of the solid solution formed between ferroelectric lead titanate and anti-ferroelectric lead zirconate. Different compositions of PZT are used for different applications. For example, for memory applications, lead titanate ($PbTiO_3$) is preferred, whereas piezoelectric applications make use of the diverging piezoelectric coefficients associated with the morphotropic phase boundary.

It is further within the scope of the present invention that piezoelectric transformers formed from the ferroelectric material $Pb(ZrTi)O_3$ (PZT) or $PbTiO_3$ are high voltage generators in which interactive electrical-mechanical energy conversion occurs based on piezoelectric effect.

It is herein further acknowledged that PZT (Lead zirconium titanate) is an inorganic compound with the chemical formula $Pb[Zr_xTi_{1-x}]O_3$ $0 \leq x \leq 1$. It is a ceramic perovskite material that shows a marked piezoelectric effect, which finds practical applications in the area of electroceramics. It is a perovskite crystal structure, each unit of which consists of a small tetravalent metal ion in a lattice of large divalent metal ions. In the case of PZT, the small tetravalent metal ion is usually titanium or zirconium. PZT materials exhibit improved properties such as high sensitivity, high operating temperature, high dielectric constants and low dielectric loss, i.e. in comparison to the metallic oxide based piezoelectric material Barium Titanate ($BaTiO_3$).

The term "piezomagnetic element" used herein generally refers to antiferromagnetic crystals and materials, such as Piezomagnetic ferrite materials, magnetoelectric ceramic materials (e.g., $Ba_{6/x}R_{2x}(Nb_{1/x}Fe_{2+x})O_3$), nickel, Ni—Fe alloy, V—Fe alloy, Fe—Co—Ni alloy, Ni—Cr—V alloy, (Fe, Cu system) Monel alloy; nickel ferrite, nickel-copper ferrite, nickel-zinc ferrite, composition systems including magnesium-manganese ferrite, nickel-cobalt ferrite etc. Piezomagnetizem may be characterized by a linear coupling between the system's magnetic polarization and mechanical strain. In a piezomagnetic, one may induce a spontaneous magnetic moment by applying physical stress, or a physical deformation by applying a magnetic field, see IEEE Std 319-1990 (1991), IEEE Standard on Magnetostrictive Materials: Piezomagnetic Nomenclature, which is incorporated herein as a reference. Moreover, it is further in the scope of the invention wherein at least one or more members of a group comprising magnetostrictive, electromagnetic, piezoelectric, and electrostrictive transducers and elements thereof are utilized.

The term "reflecting element" used herein generally refers to a component at least partially comprising a material selected from the group consisting in a non-limiting manner of: high-reflector coating, glass or amorphous materials, solid or crystalline materials such as calcium fluoride ($CaF_2$), polymers, metals such as iron and alloys thereof, stainless steel, aluminum, silver, gold and mixtures thereof, dielectric coating, extreme ultraviolet coating, UV reflecting materials, 100-280 nm reflecting materials and any combination thereof. Further examples of materials used as reflecting elements within the scope of the present invention may include: Titanium, Vanadium, Chromium, Yttrium, Zirconium, Niobium, Molybdenum, Technetium, Ruthenium, Rhodium, Palladium, Silver, Tantalum, Tungsten, Rhenium, Osmium, 0 Iridium, Platinum, Gold, Thallium, Lead, diamond-like carbon (DLC), graphite-containing materials, mixtures, blends and/or alloys thereof.

In other embodiments, a reflecting element refers to a device, surface or portion thereof that at least minimally reflects light or a plurality of wavelengths, back to its source with e.g., a minimum of scattering. In specific embodiments, an electromagnetic wave is reflected, in at least minimal extent, back along a vector that is parallel to but opposite in direction from the wave's source. Retroreflectors are devices that operate by returning light back to the light source along the same light direction. The coefficient of luminous intensity, RI, is the measure of a reflector performance, which is defined as the ratio of the strength of the reflected light (luminous intensity) to the amount of light that falls on the reflector (normal illuminance). According to a certain aspect of the invention, aluminum serves as a good reflector (approximately 92%) of visible light and an excellent reflector (as much as 98%) of medium and far infrared radiation The term "reflecting element" may also refer to an optical coating, which generally means one or more thin layers of material deposited on at least a portion of an optical component such as a lens or mirror, which alters the way in which the optic reflects and transmits light. In a specific embodiment, high-reflector coating can be used to produce mirrors which reflect greater than 99.99% of the light which falls on them. More complex optical coatings exhibit high reflection over some range of wavelengths, and anti-reflection over another range, allowing the production of dichroic thin-film optical filters. The simplest optical coatings are thin layers of metals, such as aluminum, which are deposited on substrates to make mirror surfaces. The metal used determines the reflection characteristics of the mirror; aluminum for example, yields a reflectivity of around 88%-92% over the visible spectrum; silver, which has a reflectivity of 95%-99% even into the far infrared, exhibits a decreased reflectivity (<90%) in the blue and ultraviolet spectral regions; gold, which gives excellent (98%-99%) reflectivity throughout the infrared, has a limited reflectivity at wavelengths shorter than 550 nm.

According to certain embodiments, aluminum mirror coating has the highest reflectance of any metal in the 200-400 nm (UV) and the 3,000-10,000 nm (far IR) regions; in the 400-700 nm visible range it is slightly outperformed by tin and silver and in the 700-3000 (near IR) by silver, gold, and copper. Nevertheless, according to certain embodiments of the invention, the reflecting elements as defined in any of the above are low-reflection (LR) members and structural elements of the device, adapted to reflect UV, visible light and/or IR in a very minor measure (e.g., less than 7.5%).

In alternative embodiments, high-reflection (HR) coatings are usually based on the periodic layer system composed from two materials, one with a high index, such as zinc sulfide (n=2.32) or titanium dioxide (n=2.4) and low index material, such as magnesium fluoride (n=1.38) or silicon dioxide (n=1.49). This periodic system significantly enhances the reflectivity of the surface in the certain wavelength range called band-stop, whose width is determined by the ratio of the two used indices, while the maximum reflectivity is increasing nearly up to 100% with a number of layers in the stack. The thicknesses of the layers are generally quarter-wave designed such that reflected beams constructively interfere with one another to maximize reflection and minimize transmission. Coatings built-up from deposited dielectric lossless materials can reach reflectivities greater than 99.999%, over a relatively narrow range of wavelengths. Common HR coatings can achieve 99.9% reflectivity over a broad wavelength range (tens of nanometers in the visible spectrum range).

Multilayer mirrors that are constructed of hundreds of alternating layers of a high-mass metal such as molybdenum or tungsten, and a low-mass spacer such as silicon, vacuum deposited onto a substrate such as glass, causes the mirror to reflect EUV light (wavelengths shorter than about 30 nm) of the desired wavelength as would a normal metal mirror in visible light. Using multilayer optics it is possible to reflect up to 70% of incident EUV light (at a particular wavelength chosen when the mirror is constructed).

It is also within the scope of the invention that the system comprising the claimed elements of at least one coupling element and at least one reflecting element may operate and designed as a holographic prism, influencing the treated subject. In this embodiment the system comprising the reflecting element may simultaneously satisfy the requirements of high discreteness and accuracy. It is herein acknowledged that holographic prism-like elements or holograms has the advantage of high temperature stability, high efficiency, relatively small size and weight, and the ability to tolerate sharp changes in the optical and geometric characteristics (i.e. devitrification). In other aspects, the system for the administration of PMF is designed and operated as a diffraction grating device.

According to certain aspects, the at least one reflecting-element component of the system of the present invention is configured to focus and enhance the plasma modified field. According to other aspects, the at least one reflecting element is configured to centralized and/or gather and/or reduce loss of the generated plasma modified field. According to a still other aspect of the invention, the at least one reflecting element is configured to increase the efficiency of the discharged plasma modified field. Furthermore, without wishing to be bound by theory, the system comprising the at least one reflecting element is designed to adjust and to balance the energetic resonance of the PMF interacting with the treated object or subject.

Reference is now made to magnetohydrodynamics (MHD) (magneto fluid dynamics or hydromagnetics) as an aspect of the present invention. This embodiment refers to the studies of the dynamics of electrically conducting fluids. Examples of such fluids include plasmas, liquid metals, and salt water or electrolytes. It is herein acknowledged that the fundamental concept behind MHD is that magnetic fields can induce currents in a moving conductive fluid, which in turn creates forces on the fluid and also changes of the magnetic field itself. The set of equations which describe MHD are a combination of the Navier-Stokes equations of fluid dynamics and Maxwell's equations of electromagnetism. Magnetohydrodynamics (MHD) is the physical-mathematical framework that concerns the dynamics of magnetic fields in electrically conducting fluids, e.g. in plasmas and liquid metals.

The term "brain" as used herein refers to brain cell types including neurons (also known as nerve cells) and glial cells; brain lobes including the frontal lobe, parietal lobe, occipital lobe, and temporal lobe; and brain tissues including the cortex, cranium, basal ganglia, brain stem, cerebellum, dura, the spinal cord and brain membranes and outer parts of the brain, including the meninges.

The term "fluid" as used herein generally refers to a substance that flows or continually deforms. In certain aspects, such substance continually deforms under an applied shear stress. The term "fluid" includes liquids, gases, liquid and gas mixtures, emulsions, plasmas and, to some extent, plastic solids. Non limiting examples of "fluid" included within the scope of the present invention comprise any liquid or fluid or suspension such as water, oil, raw oil, milk, honey, ketchup, blood, other media, water in oil or oil in water mixtures, petroleum, fuel, fossil oil, liquefied petroleum gas also called LPG, GPL, LP gas, liquid petroleum gas or propane or butane or mixtures thereof, biofuels and products thereof, biodiesel and products thereof, hydrocarbon gas, gas, liquid and mixtures thereof, gas mixtures, and any combination thereof.

The term "raw oil" as used herein is meant to include petroleum, crude oil, refined crude oil, fossil fuel, naturally occurring or unprocessed crude oil and any product or fraction thereof. In some aspects the aforementioned term refers to a naturally occurring, yellow-to-black liquid found in geologic formations beneath the Earth's surface. Such a liquid is commonly refined into various types of fuels. It may consist of hydrocarbons of various molecular weights and other organic compounds.

The term "unit discharge" as used herein refers to the voltage oscillation at a time.

It is according to one embodiment of the invention wherein a system for the administration of a plasma modified field (PMF) to a subject or to a substrate hosting at least one microorganism is provided. This system comprises, inter alia, modules as follows: a non-thermal gas plasma emitting source for emitting a plasma beam in a pre-defined rate or flow parameters, and a plasma modified field coupling mechanism (PMFCM). The PMFCM comprises, inter alia, a plasma beam dish having at least one opening for the passage of said plasma beam; said plasma beam dish having a first surface and a second opposite surface; said first surface of said plasma beam dish is mounted with: (i) at least one coupling element preferably selected from the group consisting of: (1) at least one ferroelectric element for providing the field; (2) at least one ferromagnetic element for providing the field; (3) at least one piezoelectric element for providing the field; and (4) at least one piezomagnetic element for providing the field and, (5) a combination thereof; and (ii) at least one reflecting element. The system further comprises at least one controller for controlling said PMFCM. In this way, the PMFCM and the controller are configured to adjust any of the at least one coupling and reflecting element in a predetermined manner thereby providing the PMF in a predetermined pulsed manner for inducing a therapeutic or regenerative or biochemical or biological or beneficial effect on the subject or on a substrate hosting at least one microorganism.

It is according to a main embodiment of the invention wherein the PMFCM is adapted to couple the plasma beam with at least one of a ferroelectric element, a ferromagnetic element, a piezoelectric element or any combination thereof. Thus the present invention uniquely provides a mechanism for discharging plasma modified field (PMF), in a predetermined manner for inducing therapeutic and/or regenerative and or biochemical or biological effects and/or beneficial or renewable effects on a subject.

It is according to another embodiment of the invention wherein the system is designed and operated to a remote or indirect treatment of the object; Gadri et al., 2000. Surface Coatings Technol 131:528-542 and Laroussi and Lu, 2005. Appl. Phys. Lett. 87:113902 and Montie et al., 2000. IEEE Trans Plasma Sci 28:41-50 and Topala and Nastuta, 2012. Plasma for Bio-Decontamination, Medicine and Food Security, NATO Science for Peace and Security Series A: Chemistry and Biology. ISBN 978-94-007-2851-6. Springer Science+Business Media B.V., p. 335 and Middelkoop et al. Burn wound healing: a role for plasma medicine and Vasile Nastuta et al., 2011. Journal of Physics D: Applied Physics. 44(10):105204; are publications incorporated herein as a reference and non limiting examples of NTP. This type of NTP in use is, e.g. a decaying plasma (afterglow)—longer lived chemical species. The NTP density and energy is e.g., of a moderate density—subject is located remote from electrodes. However, a larger volume of NTP can be generated using multiple electrodes. The spacing of target from NTP-generating electrode is approx. 5 to 20 cm; particularly 15 cm arcing (filamentous discharge) unlikely to contact subject at any power setting. In this system, there is no electrical conduction through target. The suitability for irregular surfaces is high—remote nature of NTP generation means maximum flexibility of application of NTP afterglow stream.

In other embodiments, the NTP in use is atmospheric pressure plasma jet (APPJ). The plasma may be generated using principles of corona discharge, DBD and microdischarges. Examples of applications of the NTP plasma or modified-plasma may include treatment of living cells or tissues, wound healing, cancerous cell apoptosis, blood coagulation i.e. on wounds, bone tissue modification, sterilization and decontamination. In such a case, the low temperature plasma jet is driven by high voltage pulses. In a specific embodiment, plasma jet works in helium. According to a main object, the system for administering modified plasma to a subject is applied to provide positive medical results related to recovery process of wounds i.e. of burned wounds, skin regeneration and re-epitelization.

It is according to another embodiment of the invention wherein the system is designed and operated to a direct treatment of the object; Lee et al., 2005. *Surface Coatings Technol* 193:35-38; Sladek and Stoffels, 2005. *J Phys D: Appl Phys* 38:1716-1721 and Stoffels et al., 2002. *Plasma Sources Sci. Technol.* 11:383-388 are publications incorporated herein as a reference and non limiting examples of systems designed and operated to a direct treatment. This type of NTP in use is, e.g., Active plasma—short and long-lived species. The NTP density and energy is e.g., Higher density—target in the direct path of a flow of active NTP. The spacing of target from NTP-generating electrode is approx. 1-5 cm; arcing can occur at higher power settings, can contact target. In this system, an electrical conduction through target is provided under a normal operation, but possible during arcing. The suitability for irregular surfaces is moderately high—NTP is conveyed to target in a directional manner, requiring either rotation of target or multiple NTP emitters.

It is according to another embodiment of the invention wherein the system is designed and operated in a method of electrode contact; Kelly-Wintenberg et al., 1999. *J. Vac. Sci. Technol.* A 17(4):1539-44; Laroussi et al., 2003. *New J Phys* 5:41.1-41.10; and Montenegro et al., 2002. *J Food Sci* 67:646-648 are publications incorporated herein as a reference and are provided as non limiting examples of embodiments included within the scope of the present invention. This type of NTP in use is, e.g., Active plasma—all chemical species, including shortest lived and ion bombardment. The NTP density and energy is e.g., highest density—target within NTP generation field. The spacing of target from NTP-generating electrode is approx. ≤1 cm; arcing can occur between electrodes and target at higher power settings. In this system, regarding the electrical conduction—the system is operatable e.g., if target is used as an electrode or if target between mounted electrodes is electrically conductive. The suitability for irregular surfaces is moderately low—close spacing is required to maintain NTP uniformity. However, electrodes can be shaped to fit a defined, consistent surface.

It is according to another embodiment of the invention wherein the system is designed and operated to discharge plasma generated by piezoelectric transformers (PTs). P. Rajasekaran et al., *Institute for electrical Engineering and Plasma Technology*; Ruhr-Universitaet Bochum, Germany; and Itoh et al. 2006. *Plasma Sources Sci. Technol.* 15 S51-S61, are publications incorporated herein as a reference and are provided as non limiting examples of embodiments included within the scope of the present invention. Such PT-based plasma reactors are herein shown to have various therapeutic and beneficial and regenerative effects. Example of piezoelectric transformers (PTs) used in the system of the present invention is of the material $Pb(ZrTi)O_3$ or $PbTiO_3$. Such PTs generate high voltage by the piezoelectric effect, which can cause excitation and ionization of atoms and molecules resulting in the generation of discharge plasma. In a specific embodiment, DBD occurs at atmospheric pressure and above between the PT surface and a dielectric metal having a metal back electrode. In this case an electromechanical energy conversion by the piezoelectric effect is related to the mechanical vibration of the PT and the resultant surface potential.

It is herein acknowledged that the piezoelectric transformers (PT)-based plasma reactors of the present invention are capable of generating various kinds of discharge plasma, including corona discharge, glow discharge and DBD at low voltages over a wide range of gas pressure.

It is according to another embodiment of the invention wherein the system is designed and operated to discharge non-thermal plasma created by a plasma source (i.e. plasma jet) and exposed to the plasma coupling mechanism (PCM) configured to discharge generated modified plasma in a predefined pulsed manner.

It is according to another embodiment of the invention wherein the system is designed and operated to discharge non-thermal plasma coupled to a magnetic field. Liu Jingjing et al. 2005. *Plasma Science& Technology* Vol. 7 No. 5 3073-3077; and Zongbao Feng et al., 2012 *App. Phys. Lett* 101 041602 are publications incorporated herein as a reference and are provided as non limiting examples of embodiments included within the scope of the present invention.

It is according to another embodiment of the invention wherein the system is designed and operated to discharge ferroelectric coupled non-thermal plasma field. Dunaevsky A. et al., 2001. *Journal of applied Physics* 90: 8 4108-4114; and Holzer F. et al., 2005. Plasma Chemistry and Plasma Processing 25:6 595-611, are publications incorporated herein as a reference and are provided as non limiting examples of embodiments included within the scope of the present invention.

It is according to another embodiment of the invention wherein the system is designed and operated to discharge non-thermal plasma coupled to at least one of the following: a magnetic field, an electric field or a combination thereof. Such a coupling mechanism (i.e. PMFCM) is herein demonstrated to have significantly increased or in other embodiments, synergistic effect with respect to efficiency and improved properties and results relative to applying non-thermal plasma deprived of the coupling mechanism (i.e. PMFCM).

Reference is now made to FIG. 1 presenting a schematic illustration of an out-of-scale-manner of a cross section of preferred embodiments of the system for the administration of aplasma modified-field (PMF) to a subject. The figure presents elements mounted with the plasma beam dish. According to certain embodiments of the apparatus of the present invention, H.V. (high voltage) electrode (360), shown in FIG. 1, is energized by a high frequency, high voltage power source. The electrode (360) is protruding through the second surface of the plasma beam dish, preferably at least partially comprising a polymeric material. Non limiting examples of such polymeric materials may include polycarbonates, Polystyrene (PS), polyesters, polyphenylene oxide, acrylonitrile butadiene styrene (ABS), Polyoxymethylene (POM) also called acetal, polyacetal and polyformaldehyde, styrene acrylonitrile, polyimide and blends and polymeric combinations thereof. In this embodiment, the H.V. electrode 360 is positioned in the center of the plasma beam dish.

According to a specific embodiment, no voltage is applied to the treated object or subject (400). In this embodiment, the object (400) which may be a human or animal body or a plant or a liquid or gas sample, acts as a floating electrode, and the non-thermal plasma discharge may be referred to as a floating electrode dielectric barrier discharge (FE-DBD).

In an alternative embodiment, the plasma discharger is referred to as a H.V. negative DC corona.

Figure 1A:
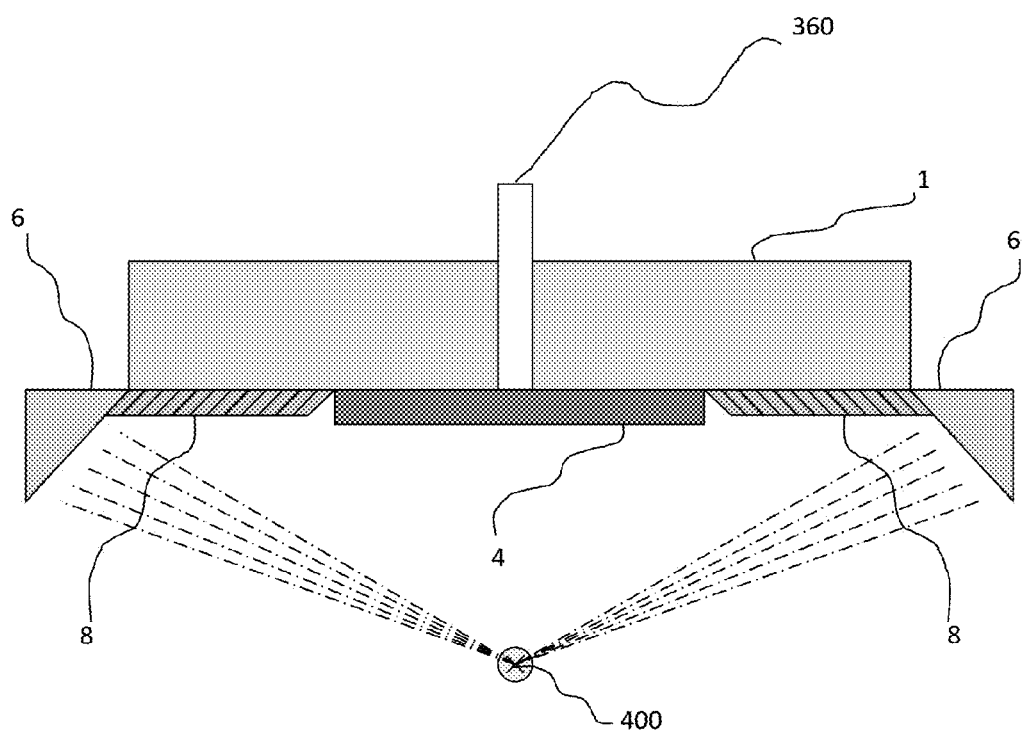
Figure 1B:
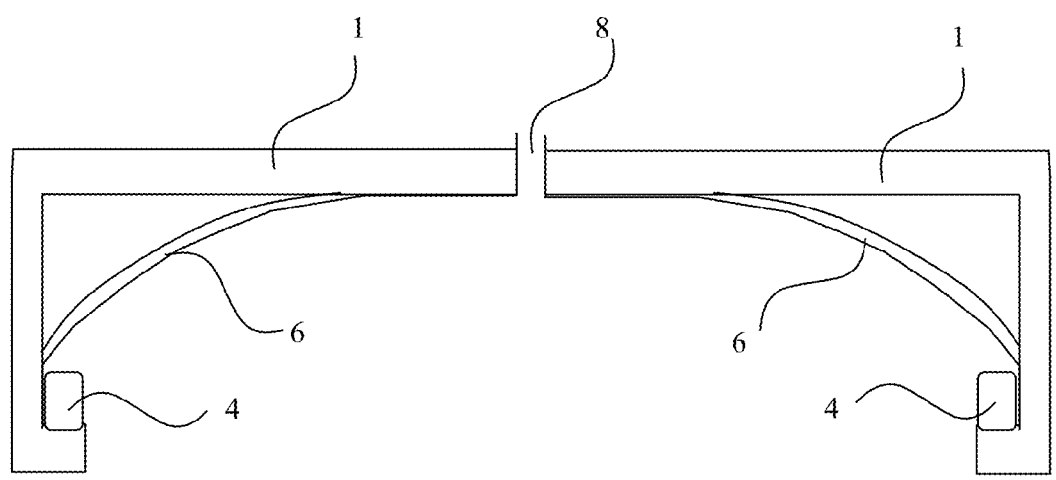
Figure 1C:
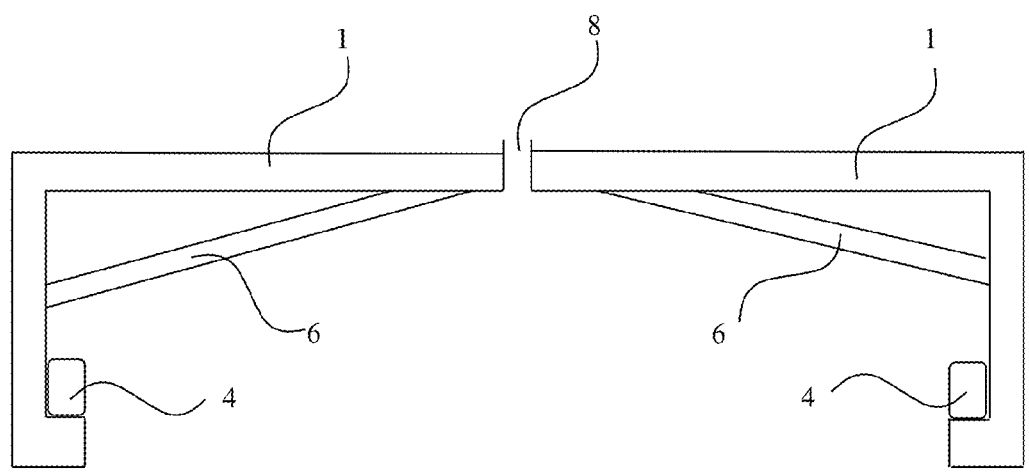

Still in the embodiment presented in FIG. 1A to 1C, the first surface of the plasma beam dish is mounted with a coupling mechanism (PMFCM) comprising elements configured to influence the H.V. NTP discharge. According to one embodiment, at least one coupling element (4), particularly a single coupling element (4) is disposed in the first surface of the plasma beam dish, i.e. in the center of the plasma beam dish. The at least one coupling element (4) together with the reflecting element (6) is configured to alter or modify or affect the plasma discharge, i.e. by improving the efficiency of the resulted modification over larger areas or to have more intense or marked effects, not limited to surface modification of the treated subject, but to affecting layers, areas or tissues beneath the outer integument of the treated subject The at least one coupling element (4) may be selected from the group consisting of: at least one ferroelectric element; at least one ferromagnetic element; at least one piezoelectric element; and any combination thereof. The plasma modified-field (PMF) (8) is discharged in a predetermined pulsed manner. The plasma beam dish is further mounted with at least one reflecting element (6). In this figure, the reflecting elements (6) are disposed in the outer rim of the plasma dish, i.e. in an opposite configuration. It is submitted that the reflecting elements have a significant and highly important effect on focusing and/or improving the modification area or efficiency applied by the plasma modified-field (PMF) (8) on subject 400. It is further submitted that the system as described herein comprising the at least one reflecting element is designed to adjust or adapt or balance the energetic resonance of the PMF interacting with, or discharged-received by the subject.

In FIGS. 1B and 1C, reflecting elements (6) are disposed on the first surface of the plasma beam dish, in both sides of the plasma beam opening (8) in opposite orientation. The reflecting elements are positioned opposite each other so as to reflect the emitted plasma ions and focus them towards the treated subject thus increasing the plasma beam penetration depth. In one embodiment, the reflecting elements (6) are characterized by amorphous configuration. In another embodiment, the opposing reflecting elements (6) are characterized by a curved (FIG. 1B) or straight (FIG. 1C) cross section on a diagonal between the x and y axis of the plasma beam dish.

With respect to materials of the reflecting elements, in one embodiment they comprise solid materials such as $CaF_2$. Furthermore, FIG. 1B and FIG. 1C present embodiments wherein the coupling elements (i.e. magnets) (4) are disposed below the reflecting elements (6), without contacting them, in both sides of the plasma beam opening. In a specific embodiment, the coupling elements are disposed in an opposite orientation in both sides of the plasma beam opening to affect the reflected plasma beam. It is within the scope of the invention that the system of FIG. 1 can be adapted for ozone treatment i.e. decomposition.

Figure 2:
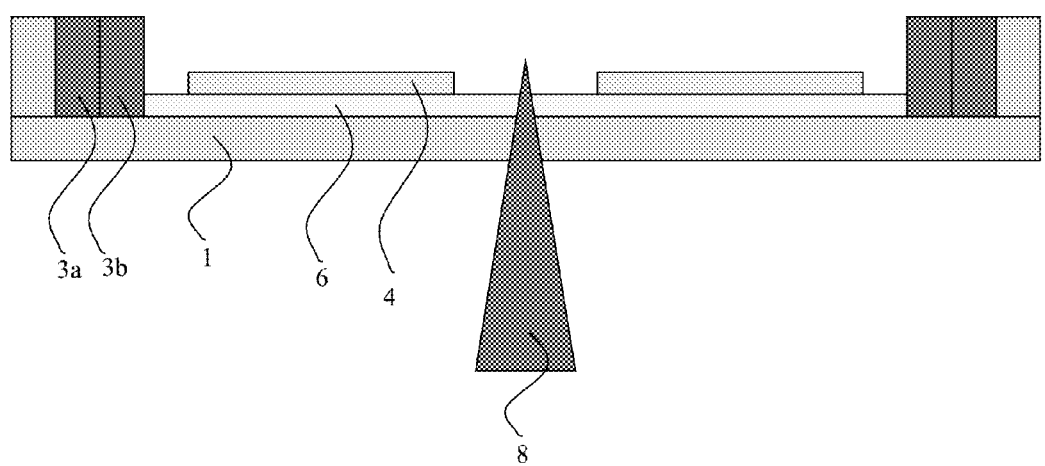
FIG. 2 is presenting in an out-of-scale-manner a schematic illustration of a cross section view of embodiments of the system for the administration of a plasma modified field (PMF) to a subject.

Reference is now made to FIG. 2 presenting in an out-of-scale-manner a schematic illustration of a cross section view of alternative embodiments of the system for the administration of plasma modified-field (PMF) to a subject. In this embodiment, a plasma beam dish having an opening for the passage of a NTP beam (8) is presented. The plasma beam dish has a first surface mounted with elements as disclosed hereinafter, and a second surface (1). The second surface (1) at least partially comprises a polymeric material. The first surface is mounted with at least one reflecting element (6). In this embodiment, the at least one reflecting element (6) is designed to be disposed as a ring like shape surrounding the plasma beam opening (8). At least one coupling element (4) is further disposed on said first surface of the plasma bean dish, preferably attached to the at least one reflecting element (6). As shown in FIG. 2, coupling elements (4) are disposed in pairs, in opposite orientation i.e. around the plasma beam opening (8). The coupling elements (4) may include ferroelectric and/or piezoelectric materials or elements or transformers. It is further presented in this figure that, ferromagnetic elements (3a and 3b) are disposed in the outer rim, or the distal part (relative to the plasma beam opening), of the plasma dish, preferably in the first surface of the plasma dish. In this embodiment, the ferromagnetic elements (3a and 3b) are disposed in pairs or sets containing two, three or more elements.

Figure 3:
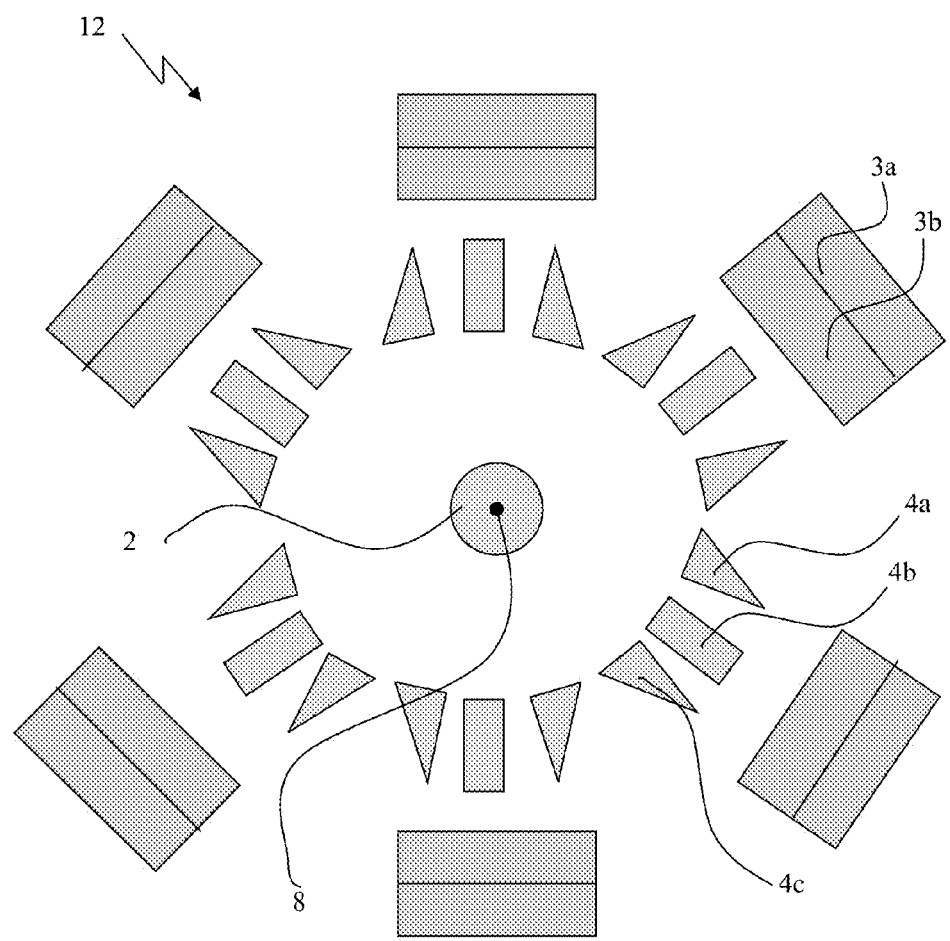
FIG. 3 is presenting in an out-of-scale-manner a schematic illustration of a top view of embodiments of the system for the administration of a plasma modified field (PMF) to a subject.

Reference is now made to FIG. 3 presenting in an out-of-scale-manner a schematic illustration of a top view of embodiments of the system as illustrated in FIG. 2. This figure presents elements mounted within the first surface of the plasma beam dish (12) comprising the PMFCM. According to one embodiment, the plasma dish (12) comprises a rounded structure. In more specific embodiments the plasma dish (12) having a diameter of about 15-20 cm. As can be seen, the elements are arranged radially around a central aperture (2) adapted for the passage of the plasma beam (8), particularly a high voltage negative DC corona discharger (not shown). The elements disclosed inter alia in combination with the at least one reflecting element (not shown) are designed to couple or modify or transform the plasma beam with at least one of a ferroelectric, a piezoelectric, ferromagnetic element or any combination thereof. The coupling elements comprising: ferroelectric and/or piezoelectric elements (4) disposed around the central aperture (2). According to certain embodiments, the coupling or transforming elements (4a, 4b, 4c) are arranged in sets of three elements per set, preferably disposed around the central aperture (2). As shown in this figure, each set of transforming elements (4a, 4b, 4c) is positioned opposite to at least one ferromagnetic element (3a, 3b). The ferroelectric elements are configured to couple the plasma beam (8) with a ferroelectric field.

In other embodiments shown in FIG. 3, ferromagnetic elements (3a, 3b) are arranged in pairs along the inner perimeter of the dish (12). In specific embodiments, six pairs of ferromagnetic elements are radially positioned in the outer rim of the first surface of the dish (12). In some aspects, the coupling elements are arranged in pairs of segments (3a and 3b) configuring an outer and inner ring-like structure. In a further aspect of the invention, the at least one pair of ferromagnetic elements is made of at least one ferromagnetic material, particularly, magnetite, ferrite, cobalt or cobalt alloy, iron and iron oxides as Fe3O4 such as samarium-cobalt magnet (e.g., $SmCo_5$, or SmCo Series 1:5; $Sm_2Co_{17}$, or SmCo Series 2:17), neodymium magnets, ferromagnetic, ferroelectric and ferrimagnetic materials, such as $Fe_3O_4$ magnetic ferrite, Alfa ferrite ($\alpha$-Fe) and beta iron ($\beta$-iron) or other paramagnetic substances or any combination thereof.

Thus the system is designed to generate a unique plasma modified-source driven by the synergic effect resulting from the combination of NTP (8) with at least one ferroelectric and/or piezoelectric element (i.e. (4a, 4b, 4c) and/or at least one magnetic field element (i.e. 3a, 3b), whereby these fields are combined with at least one reflecting element (shown in FIGS. 1 and 2).

According to one embodiment, the at least one coupling element (4) or ferromagnetic element (3a and 3b) is arranged radially around said plasma beam opening (8).

According to a further embodiment the at least one coupling element (4) or ferromagnetic element (3a and 3b) is arranged in sets of pairs or triplicates, around the plasma beam opening (8).

According to a further embodiment, the PMFCM comprises at least one pair of coupling elements (4) or ferromagnetic element (3a and 3b).

According to a further embodiment, the PMFCM comprises at least one pair of oppositely oriented coupling elements (4) or ferromagnetic element (3a and 3b).

According to a further embodiment, the PMFCM comprises at least one pair of oppositely oriented pairs of coupling elements (4) or ferromagnetic elements (3a and 3b).

According to a further embodiment, the at least one pair of coupling elements (4) or ferromagnetic elements (3a and 3b) is arranged in parallel orientation.

According to a further embodiment, the at least one pair of coupling elements (4) is arranged in the same plane, and in other embodiments the coupling elements are on different planes in succession on opposite axes.

According to a further embodiment, the at least one pair of coupling elements (4) or ferromagnetic elements (3a and 3b) is positioned such that the poles of the coupling elements (4) or ferromagnetic elements (3a and 3b) having attractive polarities or repulsive polarities.

It is well within the scope of invention wherein both (i) a plasma beam dish with a coupling element and (ii) a plasma beam dish deprived of a coupling element are disclosed. In those two embodiments, one or more coupling elements are mounted in an approximate centralized position on the first surface of the plasma dish. According to yet another embodiment, one or more coupling elements are designed as a disk having a diameter of approximately 0.5 to about 2.25 cm. In other embodiments one or more coupling elements made of or otherwise comprises material APC 841 or any suitable alternative, e.g., as defined in Table 2 below. A plasma field, emitted from an NTP source to the PMFCM comprising a plasma beam dish, is modified by at least one coupling element and discharged from the surface surrounding the coupling element. According to still another embodiment of the invention, a similar plasma beam dish, characterized by being deprived of a coupling element. Here, NTP beam discharges from the plasma dish via a centralized beam, whereas the plasma discharges from a reactor containing the coupling element affects a wider surface and a characterized by a higher intensity.

Thus the system for the administration of a plasma modified-field has many advantages. It is designed to generate and provide a highly efficient and highly powered plasma field, driven in parallel by at least one coupling element selected from a group consisting of: at least one piezoelectric element, at least one ferroelectric element, at least one magnetic element and any combination thereof, and by at least one reflecting element.

Reference is now made to FIGS. 4A and 4B, illustrating in an out-of-scale-manner a schematic view of a plasma beam dish (10) and stand thereof (100). Stand (100) reversibly- and maneuverable-immobilizing dish (10) in a predefined spatial location and 3D orientation, e.g., by means of one or more sets of arms (20) operable mechanically (See arms 21 and 22) or otherwise electrically of hydraulically. Stand (100) further comprises, e.g. reciprocally or rotatably elongatable shaft (30), affixably mounted on a suitable base (40). Stand (100) is made of a suitable material, such as polymeric composition, metal ware, composite materials and any mixture and combination thereof.

Reference is now made to FIG. 5A and FIG. 5B which illustrate in an out-of-scale-manner a set of two schematic views of plasma beam dish (11a and 11b, respectively). Dish 11a comprises a plurality of magnets, here located at the circumference of the dish, whereas dish 11b comprises at least one (here-one) magnet, located, e.g., at the central inner portion of the said dish. Dish 11a comprises a rounded structure (1) with at least one central aperture (2), adapted by means of size and shape to accommodate within at least one plasma emitting source. Along the inner perimeter of the dish a plurality of coupling elements are affixed for coupling said plasma beam with an electromagnetic and/or ferroelectric and/or piezoelectric element. The plasma beam dish further comprises at least one reflecting element (not shown). According to a further aspect, the plasma beam is herein used to focus the at least one field generated by the at least one coupling element to provide a plasma modified field (PMF): see for example coupling elements 3a and 3b. The dish, as defined above, is 3D oriented and spatially arranged by means of immobilizing arms mechanism (20).

It is in the scope of the invention wherein the dish, particularly the second surface of the dish is made or comprises polymers, such as 70% Acrylonitride Butadiene Styrene (ABS) and Polysterene (PS). It is further in the scope of the invention wherein the dish is made of, or otherwise comprises, a mixture of polymers, such as 70% PS and 30% ABS (wt/wt or mole/mole).

Reference is now made to FIG. 6 illustrating in an out-of-scale-manner a various schematic views of a plasma beam dish (11) according to one embodiment of the invention. It is well within the scope of the invention wherein the external diameter of the dish is about 200 mm, the width of the perimeter rim (1) is 15 mm and dish width is 30 mm. These are non limiting examples of the plasma beam dish. In this embodiment, six coupling elements, i.e. magnets and/or ferroelectric elements are evenly applied along the dish' perimeter (i.e., θ between element 3a and 3b is 60°). Nevertheless, it is well within the scope of the invention wherein one coupling element is applied, 2 to 4 coupling elements are applied, 4 to 12 coupling elements are applied and wherein 20 or less to 240 and more coupling elements are applied. Thus, the θ between coupling element 3a and 3b is varied between 0.5° to 270°.

It is in the scope of the invention wherein the coupling elements are set in pairs, each of which is arranged as a first coupling element and a second coupling element. Said first coupling element is located opposite to said second coupling element (θ between $1^{st}$ and $2^{nd}$ coupling elements is 180°).

It is further in the scope of the invention wherein at least one of the coupling elements, i.e. magnet is made of cobalt or cobalt alloy, such as samarium-cobalt magnet (e.g., $SmCo_5$, or SmCo Series 1:5; $Sm_2Co_{17}$, or SmCo Series 2:17), neodymium magnets, ferromagnetic, ferroelectric and ferrimagnetic materials, such as $Fe_3O_4$ magnetic ferrite, Alfa ferrite (α-Fe) and beta iron (β-iron); paramagnetic substances, such as platinum, aluminum, and oxygen; Diamagnetic means repelled by both poles. Compared to paramagnetic and ferromagnetic substances, diamagnetic substances, such as carbon, copper, water, and plastic and any mixtures and combinations thereof.

It is further in the scope of the invention wherein the dish comprises six coupling elements: positioned at 12 o'clock, 2 o'clock, 4 o'clock, 6 o'clock, 8 o'clock, and 10 o'clock. It is further in the scope of the invention wherein said 12 and/or 10 o'clock is a cobalt-containing coupling element, i.e. magnet. It is further in the scope of the invention wherein said 2 and/or 4 o'clock is a magnetite-type coupling element, i.e. magnet. It is further in the scope of the invention wherein said 6 and/or 8 o'clock is an alfa-ferrite-type coupling element, i.e., magnet.

It is further in the scope of the invention wherein the pairs of magnets' or the coupling elements poles are of S-S, N-N or S-N orientation.

It is further in the scope of the invention wherein the NTP plasma discharger is provided in a plasma discharging technology. Non limiting examples of NTP discharging technology within the scope of the present invention include Glow, corona, an atmospheric pressure plasma jet (APPJ), dielectric barrier discharge (DBD), micro-hollow cathode discharge (MHCD), one atmosphere uniform glow-discharge plasma (OAUGDP), plasma needle, an atmospheric pressure glow discharger, a high voltage DC corona discharger, a high voltage negative DC corona discharger, a high voltage positive DC corona discharger, a floating electrode dielectric barrier discharger, gliding arc discharge (GD) induced plasma and a plasma jet.

Reference is now made to FIG. 7A, illustrating in an out-of-scale-manner a schematic view of an atmospheric pressure plasma jet as an alternative embodiment of the present invention. As been stated by n Nehra et al. (See Nehra V, Kumar A, Dwivedi H (2008) Atmospheric non-thermal plasma sources. *Int J Eng* 2(1):53-68 which is incorporated herein as a reference), discharge capable of generating non-thermal plasmas at atmospheric pressure is atmospheric-pressure plasma jet. This type of APPJ consists of two concentric electrodes through which a mixture of helium, oxygen or other gases flows. In this arrangement, the inner electrode is coupled to 13.56 MHz radio frequency power at a voltage between 100-250 V and the outer electrode is grounded. By applying RF power, the discharge is ignited and operates on a feed stock gas, which flows between an outer grounded, cylindrical electrode and a central electrode and produces a high velocity effluent stream of highly reactive chemical species. Central electrodes driven by radio frequency power accelerate free electrons. These energetic electrons undergo inelastic collisions with the feed gas, producing excited state molecules, atoms, free radicals and additional ion-electron pairs. Once the gas exits the discharge volume, ions and electrons are rapidly lost by recombination, but the fast flowing effluent still contains neutral metastable species and radicals. The key operational features of APPJ are as follows: (1) it produces a stable, homogenous and uniform discharge at atmospheric pressure; (2) operates at radio frequency (RF) power of 250 W and frequency of 13.56 MHz; (3) the ionized gas from the plasma jet exits through the nozzle where it is directed onto the substrate and hence utilized in downstream processing; (4) it operates without a dielectric cover over the electrode, yet is free from filaments, streamers and arcing; (4) The gas temperature of the discharge is as low as 50° C., allowing it to treat delicate surfaces without damage, or as high as 300° C., allowing it to treat robust surfaces much more aggressively. (5) It exhibits a great similarity to low-pressure DC glow discharge.

Reference is now made to FIG. 7B, still illustrating in an out-of-scale-manner a schematic view of a corona discharger (See all details in Nehra et al.) as alternative embodiments of the present invention. Corona discharge technology involves generating non thermal atmospheric plasma. It directly affects the generation of free radicals. Corona discharge exists in several forms, depending on the polarity of the field and the electrode geometrical configuration. Corona discharge arrangements comprising asymmetric electrode pair and results from the electric field that surrounds the inhomogeneous electrode arrangements powered by a continuous or pulsed DC voltage. The development of a coronal discharge preferably involves the following steps: an asymmetric electrode configuration is made; a high voltage is applied and free electric charge is made available; and the creation of electric current multiplication and avalanche breakdown.

In other alternative embodiments involving DBD plasma technology, plasma discharges between two electrodes, at least one electrode insulated with a dielectric layer can be operated in a wide range of geometrical configurations such as the classical volume discharge, surface discharge, and coplanar discharge. Volume discharges can also have either planar or coaxial arrangements. In planar electrode arrangements, the two electrodes are parallel to each other, and one or two dielectric barriers are always located either (i) on the powered or the ground electrode, or (ii) on both the electrodes, or (iii) in between the two metal electrodes. The electrodes in DBD can also be arranged in a coaxial manner having one electrode inside the other with at least one or two dielectric barriers located either (i) on the outer side of the inner electrode/on the inner side of the outer electrode, or (ii) on both the electrodes facing each other, or (iii) in between the two cylindrical electrodes. Besides the volume discharges, other designs also exist that use either surface or coplanar discharge geometry. Surface discharge device have a thin and long electrode on a dielectric surface and an extended counter-electrode on the reverse side of the dielectric. In this configuration, the discharge gap is not clearly defined and so the discharge propagates along the dielectric surface. There also exist combinations of both volume and surface discharge configuration such as the coplanar arrangement used in plasma display panel. The coplanar discharge device is characterized by pairs of long parallel electrodes with opposite polarity, which are embedded within a dielectric bulk nearby a surface. In addition to these configurations, other variants of DBD are also used in various applications. The typical arrangements of DBD, shown by Nehra et al., exhibit two major discharge modes, either filamentary mode, which is the common form of discharge composed of many micro-discharges that are randomly distributed over the electrode surface; or homogenous glow discharge mode, also known as atmospheric pressure glow discharge mode due to similarity with dc glow discharges.

Reference is now made to FIG. 8 illustrating in an out-of-scale-manner a schematic view of a system for the administration of a plasma modified field (PMF) to a subject (1000). The system comprising NTP discharger (200) mounted on a plasma modified-field coupling mechanism (PMFCM) comprising dish (10) in a manner that plasma generated by discharger (200) is discharged, influenced or modified or coupled by the field generated by at least one coupling element and optionally, by at least one reflecting element (not shown) fixed on dish (10), and a plasma modified-field (PMF) is discharged (50) in a highly efficient, focused and predefined manner towards object (60).

Figure 9A:
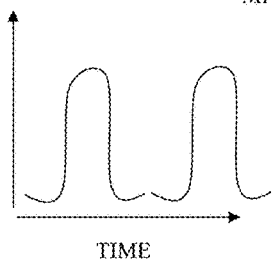
Figure 9B:
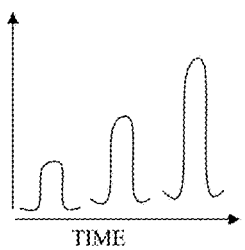
Figure 9C:
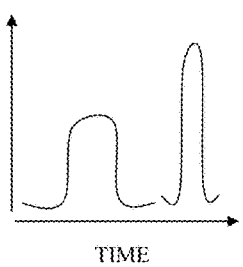
Figure 9D:
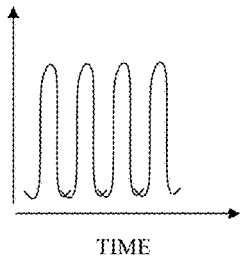
Figure 9E:
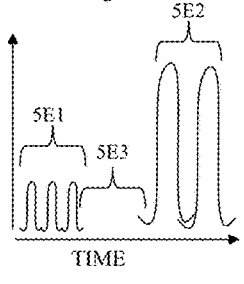
Figure 9F:
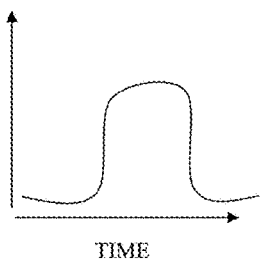

Reference is now made to FIG. 9A-9F illustrating in an out-of-scale-manner a schematic view of plasma modified-field pulse profiles, according to some embodiments of the invention, namely the profile of the intensity of the discharge plasma over time. FIG. 9A illustrates a profile wherein a PMF is discharged in an equal and homogenous intensity over the treatment time. FIG. 9B illustrates a profile wherein PMF is discharged in a non-equal and heterogeneous intensity over the treatment time. Here the intensity of the PMF is increased and the pulse duration is equal along all pulses. Thus, a decrease in intensity and decrease-then-increase and/or increase-then-decrease intensities are possible. FIG. 9C illustrates a profile wherein PMF is discharged non-evenly and in various intensities. FIG. 9D illustrates a profile of many pulses shot in a predefined pattern. FIG. 9E illustrates a profile wherein PMF is discharged non-evenly and in various intensities: at least one first set or cycle of pulses (5E1), at least one second set or cycle of pulses (5E2), where at least one time laps (e.g., 0 to 1 min., 5E3) is provided between the said two sets or cycles of pulses. Additional and/or alternative examples of pulse cycles or pulse profiles within the scope of the present invention are provided in Table 3.

In one embodiment, the PMF is applied to the subject in a predetermined mode, particularly pulse profile mode, which is determined or more specifically adjusted according to the classification (i.e. taxonomic classification) of the treated subject or according to a predetermined desirable effect. For example, a PMF pulse profile designed to induce a regenerative or beneficial effect or a biochemical effect on a plant may be different (i.e. by pulse duration or pulse intervals or both) from the PMF pulse profile designed to induce a therapeutic or biological or biochemical or regenerative or beneficial effect in human and/or from the PMF pulse profile designed to induce a beneficial effect on water or gas or raw oil or tissue or on microorganism.

It is within the scope of the present invention to provide a method for providing at least one biological effect in at least one microorganism, wherein the method comprises steps of: (a) providing a system for administering modified plasma. The aforementioned system comprises: (i) a non-thermal plasma (NTP) emitting source for emitting a NTP beam in a pre-defined flow rate; and (ii) a plasma coupling mechanism (PCM), wherein the PCM comprises a plasma beam dish having at least one opening for the passage of the NTP beam; the plasma beam dish having a first surface and a second opposite surface; the first surface of the plasma beam dish is mounted with at least one coupling element selected from a group consisting of: 1. at least one ferroelectric element for providing a ferroelectric induced field for coupling with the NTP beam; 2. at least one ferromagnetic element for providing a ferromagnetic induced field for coupling with the NTP beam; 3. at least one piezoelectric element for providing a piezoelectric induced field for coupling with the NTP beam; and 4. at least one piezomagnetic element for providing a piezomagnetic induced field for coupling with the NTP beam; further wherein the system additionally comprises at least one reflecting element configured to focus the NTP beam thereby generating modified plasma beam; (b) providing a substrate hosting the at least one microorganism; and (c) administering the generated modified plasma beam in a predetermined pulsed manner to the at least one microorganism hosted in the substrate, to provide the at least one biological effect to the at least one microorganism.

It is further within the scope to provide the method as defined in any of the above, wherein the substrate is selected from the group consisting of: food, liquid, beverage, suspension, biological culture, medium, growth medium, emulsion, biological tissue, biological organism, human, animal, plant, fluid, soil, minerals, media, gas, gas and liquid mixtures, gas mixtures, cells, tissue culture, organs and any combination thereof.

It is further within the scope to provide the method as defined in any of the above, wherein the microorganism is selected from the group consisting of: yeast, bacteria, archaea, algae, corynebacteria, aerobic bacteria anaerobic bacteria, fungi, protozoa, virus, spores, phyrhv, hypha, Candida, prion, and any combination thereof.

It is further within the scope to provide the method as defined in any of the above, wherein the bacteria is selected from the group consisting of Listeria monocytogenes, Escherichia coli, Salmonella, bacteria of the Enterobacteriaceae family, bacteria of the Listeriaceae family, gram positive bacteria, gram negative bacteria, anaerobic bacteria, aerobic bacteria, Staphylococcus aureus, Pseudomonas aeruginosa, Staphylococcus epidermidis, Staphylococcus haemolyticus, enterococcus faecalis, Clostridiaceae family, Clostridium, Corynebacterium, actinobacteria and any combination thereof. It is further within the scope to provide the method as defined in any of the above, additionally comprises steps of providing the at least one biological effect up to 6 hours from the administration of the modified plasma beam.

It is further within the scope to provide the method as defined in any of the above, additionally comprises steps of comparing the level of the at least one biological effect to the level of the effect in a control microorganism.

It is further within the scope to provide the method as defined in any of the above, wherein the at least one biological effect is selected from the group consisting of: activation effect, inactivation effect, metabolic effect, anabolic effect, amphibolic effect, regeneration effect, renewable effect, effect on a biochemical pathway, effect on the production of at least one biochemical compound, catabolic effect, anabolic effect, sterilization, antibacterial effect, deactivation effect, survival effect, sterilization effect, infertility effect, loss of viability effect, killing effect, destruction effect, induction effect, destruction of pathogens effect, bacterial destruction effect, viruses destruction effect, genetic effect, water or gas disinfection effect, effect on water or gas contamination parameters, effect on chemical composition, bacteria concentration, phenol concentration, effect on chemical composition of raw oil, effect on raw oil components and concentration, effect on biofuel or biodiesel compounds production and/or destruction, and any combination thereof.

It is further within the scope to provide the method as defined in any of the above, wherein the method provides an effect on enhancing production of at least one biochemical compound in the at least one microorganism.

It is further within the scope to provide the method as defined in any of the above, additionally comprises steps of harvesting the at least one biochemical compound.

It is further within the scope to provide the method as defined in any of the above, additionally comprises steps of selecting the biochemical compound from the group consisting of biofuel and/or products thereof, biodiesel and/or products thereof, organic compounds, metabolic compounds, metabolites, antibiotics, prodrugs, fermentation products, acid compounds, gas compounds, alcohol compounds, precursors of amino acids, and any combination thereof.

It is further within the scope to provide the method as defined in any of the above, additionally comprises steps of selecting the biochemical compound from the group consisting of ethanol, 1-propanol, 2-propanol, 2,3-butanedione, vicinal diketone, acetoin, acetone, 2,3-butanediole, methanol, Isobutanol, butanol, 1-butanol, n-butanol, propandiol also referred to as Propanediol or 1,3-Propanediol, any isomer or racemic compound thereof, any intermediate pathway compound or precursor thereof, and any mixture thereof.

It is further within the scope to provide the method as defined in any of the above, additionally comprises steps of inducing the production of the at least one biochemical compound to a concentration of between about 5 mg/l to about 200 mg/l or more, more particularly, about 10 mg/l to about 100 mg/l or more.

It is further within the scope to provide the method as defined in any of the above, wherein the method provides an effect selected from the group consisting of sterilization, killing, deactivation, inactivation, infertilization and any combination thereof of said at least one microorganism.

It is further within the scope to provide the method as defined in any of the above, additionally comprises steps of providing said at least one biological effect in said at least one microorganism without significantly altering the pH or Hydrogen peroxide concentration or a combination thereof of said substrate hosting said at least one microorganism.

It is further within the scope to provide a system for administering modified plasma to a substrate hosting at least one microorganism, the system comprising: (a) a non-thermal plasma (NTP) emitting source for emitting a NTP beam in a pre-determined flow rate; and (b) a plasma coupling mechanism (PCM), wherein the PCM comprises a plasma beam dish having at least one opening for passage of the NTP beam; the plasma beam dish having a first surface and a second opposite surface; the first surface of the plasma beam dish comprises at least one coupling element selected from a group consisting of: (i) at least one ferroelectric element for providing a ferroelectric induced field for coupling with the NTP beam; (ii) at least one ferromagnetic element for providing a ferromagnetic induced field for coupling with the NTP beam; (iii) at least one piezoelectric element for providing a piezoelectric induced field for coupling with the NTP beam; and (iv) at least one piezomagnetic element for providing a piezomagnetic induced field for coupling with the NTP beam; wherein the system additionally comprises at least one reflecting element configured to focus the plasma beam, thereby providing the modified plasma in a predetermined pulsed manner, further wherein the system provides at least one biological effect to the at least one microorganism.

It is further within the scope to provide the system as defined in any of the above, wherein the NTP emitting source is selected from the group consisting of a dielectric barrier discharger, an atmospheric pressure glow discharger, a corona plasma discharger, a high voltage DC corona discharger, a high voltage negative DC corona discharger, a high voltage positive DC corona discharger, a floating electrode dielectric barrier discharger, gliding arc discharge (GD) induced plasma and a plasma jet.

It is further within the scope to provide the system as defined in any of the above, wherein the at least one coupling element at least partially comprises Polyvinylidene fluoride, polyvinylidene difluoride (PVDF), PZT, lead zirconium titanate, ferroelectric oxides, $Pb[Zr(x)Ti(1-x)]O3$, $PbZrO3$, $PbTiO_3$, Barium Titanate ($BaTiO3$), $(Ba, Sr)TiO3$, $Ba(1-x)Sr(x)TiO3$, a ferroelectric material characterized by at least one of piezoelectricity, pyroelectricity and memory properties, a permanent magnet, an electromagnet, a superconducting magnet, Cobalt, Magnetite ($Fe3O4$), α-ferrite (α Fe), iron, ferromagnetic alloys, piezomagnetic ferrite materials, magnetoelectric ceramic materials and any combination thereof.

It is further within the scope to provide the system as defined in any of the above, wherein the at least one reflecting element at least partially comprises a material or element selected from the group consisting of: a reflector coating, metals, iron, metal alloys, stainless steel, aluminum, silver, gold and mixtures thereof, dielectric coating, ultraviolet coating, UV reflecting materials, 100-280 nm reflecting materials, glass, amorphous materials, solid materials, insoluble materials, crystalline materials, polymers and any combination thereof.

It is further within the scope to provide the system as defined in any of the above, wherein the at least one coupling element is arranged in at least one set of pairs or triplicates or in at least one set of more than three coupling elements.

It is further within the scope to provide the system as defined in any of the above, wherein the modified plasma is characterized by at least one parameter selected from the group consisting of: a dose range of between about 0.1 J/cm2 to about 4 J/cm2, a frequency range of between about 100 Hz and about 20 MHz, a relative dielectric constant in the range of between about 500 and about 2500, a piezoelectric charge constant in the range of between about 100 (10-12 C/N or 10-12 m/V) to about 1000 (10-12 C/N or 10-12 m/V), a piezoelectric voltage constant in the range of between about 5 (10-3 Vm/N or 10-3 m2/C) to about 50 (10-3 Vm/N or 10-3 m2/C), frequency constants in the range of between about 1000 (Hz·m or m/s) to about 5000 (Hz·m or m/s) and any combination thereof.

It is further within the scope to provide the system as defined in any of the above, wherein the modified plasma is adapted to provide at least one biological or biochemical effect selected from the group consisting of: at least one brain related parameter, protein fingerprint or profile, enzymatic activity, protein crystallization, at least one medical or therapeutic effect, at least one plant parameter, at least one water parameters, at least one air pollution parameter, at least one fluid or gas parameter, at least one oil or raw oil parameter, treatment of gaseous emissions, ozone treatment, increased functional recovery after a disruptive effect, at least one immune system parameter, at least one skin related parameter, wound healing, recovery from bacterial infection, recovery from viral infection, tissue regeneration, pain relief, antioxidant activity, at least one rheological property, in vivo effect, in vitro effect and any combination thereof.

It is further within the scope to provide the system as defined in any of the above, wherein said at least one biological effect in said at least one microorganism is provided without significantly altering the pH or Hydrogen peroxide concentration or a combination thereof of said substrate hosting said at least one microorganism.

It is in the scope of the invention to disclose a system for the administration of a plasma modified field (PMF) to a subject. The system comprises, inter alia, (a) a non-thermal plasma (NTP) emitting source for emitting a plasma beam in a predetermined rate; (b) a plasma modified field coupling mechanism (PMFCM) comprising a plasma beam dish having at least one opening for the passage of the plasma beam; the plasma beam dish having a first surface and a second opposite surface; and (c) a controller for controlling the PMFCM. It is within the scope that the first surface of the plasma beam dish is mounted with: (i) at least one coupling element, and (ii) at least one reflecting element. The at least one coupling element is selected from the group consisting of: (1) at least one ferroelectric element for providing the field; (2) at least one ferromagnetic element for providing the field; (3) at least one piezoelectric element for providing the field and (4) at least one piezomagnetic element for providing the field. It is also within the scope that the PMFCM and the controller is configured to adjust any of the at least one coupling and reflecting element in a predetermined manner thereby providing the PMF for inducing a therapeutic or biochemical or biological or renewable effect or beneficial effect on the subject or on a substrate hosting at least one microorganism According to a main embodiment of the invention, the modified plasma or PMF generated by the system of the present invention is applied in a predetermined pulsed manner.

It is in the scope of the invention wherein the NTP plasma emitting source of the system as defined in any of the above is mounted on the second opposite surface of the plasma beam dish.

It is in the scope of the invention, wherein the system as defined in any of the above is further adapted to provide pulses of the PMF in a predetermined manner. In a specific embodiment, the system comprises a controlling or regulating mechanism for providing the modified plasma pulses in a predefined manner. Such a mechanism may comprise computerized algorithm or software.

It is in the scope of the invention, wherein the NTP emitting source of the system as defined in any of the above is selected from the group consisting of a dielectric barrier discharger, an atmospheric pressure glow discharger, a corona plasma discharger, a high voltage DC corona discharger, a high voltage negative DC corona discharger, a high voltage positive DC corona discharger, a floating electrode dielectric barrier discharger, gliding arc discharge (GD) induced plasma and a plasma jet.

It is in the scope of the invention, wherein the at least one coupling element of the system as defined in any of the above comprises a ferroelectric material characterized by at least one of piezoelectricity, pyroelectricity and memory properties.

It is further within the scope of the invention, wherein the coupling element at least partially comprises Polyvinylidene fluoride, polyvinylidene difluoride (PVDF), PZT, lead zirconium titanate, ferroelectric oxides, Pb[Zr(x)Ti(1−x)]O3, PbZrO3, Barium Titanate (BaTiO3), (Ba, Sr)TiO3, Ba(1−x)Sr(x)TiO3, PbTiO$_3$, piezomagnetic ferrite materials, magnetoelectric ceramic materials and any combination thereof.

It is further within the scope of the invention, wherein the coupling element is selected from the group consisting of a permanent magnet, an electromagnet, a superconducting magnet, and any combination thereof.

It is further within the scope of the invention, wherein the ferromagnetic element comprises at least one material selected from the group consisting of Cobalt, Magnetite (Fe$_3$O$_4$), α-ferrite (α Fe), iron, ferromagnetic alloys and mixtures thereof.

It is further within the scope of the invention, wherein the plasma beam dish, at least partially comprises a polymeric material selected from the group consisting of polycarbonates, Polystyrene (PS), polyesters, polyphenylene oxide, acrylonitrile butadiene styrene (ABS), styrene acrylonitrile, polyimide and blends and polymeric combinations thereof.

It is further within the scope of the invention, wherein the at least one reflecting element at least partially comprises a material or element selected from the group consisting of: high-reflector coating, metals such as iron and alloys thereof, stainless steel, aluminum, silver, gold and mixtures thereof, dielectric coating, extreme ultraviolet coating, high energy UV, glass, amorphous (non-crystalline) solid materials, polymers and any combination thereof.

It is further within the scope of the invention, wherein the at least one plasma beam opening is positioned in the center of the plasma beam dish.

It is further within the scope of the invention, wherein the at least one coupling element is positioned in the center of the plasma beam dish.

It is further within the scope of the invention, wherein the at least one coupling element is arranged radially around the plasma beam opening.

It is further within the scope of the invention, wherein the at least one coupling element is arranged in at least one set of pairs or triplicates or in at least one set of more than three coupling elements.

It is further within the scope of the invention, wherein the PMFCM comprises at least one pair of coupling elements.

It is further within the scope of the invention, wherein the PMFCM comprises at least one pair of oppositely oriented coupling elements.

It is another object of the invention to disclose the system for the administration of a plasma modified field (PMF) as defined above, wherein the PMFCM comprises at least one pair of oppositely oriented pairs of coupling elements.

It is further within the scope of the invention, wherein the at least one pair of coupling elements is arranged in parallel orientation.

It is further within the scope of the invention, wherein the at least one pair of coupling elements is positioned such that the poles of the coupling elements having attractive polarities or repulsive polarities.

It is further within the scope of the invention, wherein the at least one coupling element provides a magnetic field in the range of 25 μT to 10 T and higher.

It is further within the scope of the invention, wherein the at least one coupling element comprises a plurality of coupling elements positioned around the plasma beam opening.

It is further within the scope of the invention, wherein the at least one reflecting element is positioned in the outer rim of the plasma dish.

It is further within the scope of the invention, wherein the at least one reflecting element comprises one, two, three or more reflecting elements, or the at least one reflecting element is configured as a ring-like shape surrounding the plasma beam opening.

It is further within the scope of the invention, wherein the PMF is applied in a pulsed manner or in a continuous manner or in a combination thereof.

It is further within the scope of the invention, wherein the PMF is applied in a series of pulses having predetermined rates and duration.

It is further within the scope of the invention, wherein the PMF is applied in a series of pulses characterized by a constant frequency value.

It is further within the scope of the invention, wherein the PMF is applied in a series of pulses characterized by increasing duration and/or increasing pulse intervals.

It is further within the scope of the invention, wherein the PMF is applied in a series of pulses selected from the group consisting of nanosecond pulses, millisecond pulses, second pulses and a combination thereof.

It is further within the scope of the invention, wherein the PMF is applied at a dose range of between about 0.1 J/cm2 to about 4 J/cm2.

It is further within the scope of the invention, wherein the PMF is applied in a frequency range of between about 100 Hz and about 20 MHz.

It is further within the scope of the invention, wherein the PMF is characterized by a relative dielectric constant in the range of between about 500 and about 2500.

It is further within the scope of the invention, wherein the PMF is characterized by a piezoelectric charge constant in the range of between about 100 (10-12 C/N or 10-12 m/V) to about 1000 (10-12 C/N or 10-12 m/V).

It is further within the scope of the invention, wherein the PMF is characterized by a piezoelectric voltage constant in the range of between about 5 (10-3 Vm/N or 10-3 m2/C) to about 50 (10-3 Vm/N or 10-3 m2/C).

It is further within the scope of the invention, wherein the PMF is characterized by frequency constants in the range of between about 1000 (Hz·m or m/s) to about 5000 (Hz·m or m/s).

It is further within the scope of the invention, wherein the power of a pulse of the potential (or voltage) ranges between about 0.1 W to about 10 W.

It is in the scope of the invention wherein the system as defined in any of the above is provided useful for treating, objects, human, animals, plant and fluids such as water, oil, raw oil, milk, honey, emulsion, ketchup, blood, suspension, other media, gas and liquid and mixtures thereof.

It is in the scope of the invention wherein the system as defined in any of the above is provided useful for functional recovery, for pain relief, water purification, gas pollution purification, ozone decomposition, disease and/or medical disorders therapy, plant growth, increase and improve agriculture yield, such as fruit size, fruit weight and increase root system strength.

It is further within the scope of the invention, wherein said subject is selected from the group consisting of: human, animal, plant, flatworms, planaria, micro-organisms, fluid, emulsion, suspension, soil, minerals, media, gas, liquid and gas mixtures and any predetermined object.

It is further within the scope of the invention, wherein the system is adapted to provide a therapeutic or regenerative or beneficial effect on cells, tissues, tissue culture, organs and a combination thereof.

It is further within the scope of the invention, wherein the system is adapted to provide an effect beneath the outer integument of the treated subject.

It is further within the scope of the invention, wherein the system is adapted to provide a synergic effect with respect to inducing a therapeutic or regenerative or biological, or beneficial effect on the subject as compared to the effect induced by each of the plasma coupled elements individually administered.

It is further within the scope of the invention, wherein the applied PMF affect the brain.

It is further within the scope of the invention, wherein the applied PMF is adapted to affect at least one brain cell or tissue type selected from the group consisting of: neurons, nerve cells, glial cells, brain membranes, the frontal brain lobe, the parietal brain lobe, the occipital brain lobe, the temporal brain lobe, the cortex, cranium, basal ganglia, brain stem, cerebellum, dura, the spinal cord and any combination thereof.

It is further within the scope of the invention, wherein the PMF discharge effect provided by the system of the present invention can be detected by detecting means and methods including among other direct measures such as gas discharge visualization (GDV) means, Kirlian photography means, digital visualization of biofield (DVB) and indirect measurement such as a superconducting quantum interference device (SQUID), biophton measurement, Biophoton Imaging, CCD (charge-coupled device), photomultiplier tube (PT), eletrophotonic imaging or Electro Photon Imaging (EPI).

It is further within the scope of the invention, wherein said applied PMF is adapted to affect biochemical parameters selected from the group consisting of: brain related parameters, protein fingerprint or profile, enzymatic activity, protein crystallization, medical therapeutic effects, improved plant parameters, improved water parameters, improved air pollution parameters, gas parameters, treatment of gaseous emissions, ozone treatment, increased functional recovery after a disruptive effect, antimicrobial activity, sterilization, disinfection, microbial deactivation, production of biochemical compounds and/or metabolites, food sterilization; production of fermentation products, production of biofuels or derivative or compounds thereof, especially in microorganisms, improved immune system, skin related parameters, wound healing, recovery from bacterial infection, recovery from viral infection, tissue regeneration, pain relief, antioxidant activity, improved rheological properties and any combination thereof.

It is further within the scope of the invention, wherein said system is adapted to induce a therapeutic effect on a disease or condition selected from the group consisting of: rheological properties of blood, autoimmune diseases, degenerative diseases, neurological diseases, neurodegenerative diseases, inflammatory diseases, cancer-related diseases, cardiovascular diseases, skin-related diseases or conditions, pain relief, antiaging, functional recovery after having a disruptive effect, bowel-related diseases, enteric diseases, attention disorder (ADHD) syndromes and any combination thereof.

It is further within the scope of the invention, wherein said skin-related diseases or conditions are selected from the group consisting of: wound, burn injury, fresh trauma wound, skin infections, skin injuries such as scratches or scraps, skin inflammatory disease, psoriasis, dermatitis, lupus, necrosis, gangrene, eczema, atopic dermatitis, chronic wounds, skin cells regeneration, wrinkles, acne, UV radiation diseases, skin cancer, malignancy, cancerous tissue, melanoma, nodular melanoma, Acral lentiginous melanoma, Lentigo maligna, Superficial spreading melanoma, basal cell carcinoma, Bowen's disease, infections wounds, ulcers, burn injuries, fresh trauma wounds, wound at a haemostasis stage, wound at an inflammation stage, wound at a granulation or proliferation stage, wound at a contracture stage, wound at an epithelisation stage, wound at cancerous stage and any combination thereof.

According to certain embodiments, it is herein acknowledged that basal-cell carcinomas may include the following types: Nodular basal-cell carcinoma (Classic basal-cell carcinoma), Cystic basal-cell carcinoma, Cicatricial basal-cell carcinoma (Morpheaform basal-cell carcinoma, Morphoeic basal-cell carcinoma), Infiltrative basal-cell carcinoma, Micronodular basal-cell carcinoma, Superficial basal-cell carcinoma (Superficial multicentric basal-cell carcinoma), Pigmented basal-cell carcinoma, Rodent ulcer (Jacobi ulcer), Fibroepithelioma of Pinkus, Polypoid basal-cell carcinoma, Pore-like basal-cell carcinoma and Aberrant basal-cell carcinoma.

In other certain embodiments, basal-cell carcinoma may be divided into 3 groups, based on location and difficulty of therapy: (1) Superficial basal-cell carcinoma, which is considered as equivalent to "in-situ". Up until the present invention it is known to be effectively treated with topical chemotherapy; (2) Infiltrative basal-cell carcinoma, which often encompasses morpheaform and micronodular basal-cell cancer. Up until the present invention it is known as being more difficult to treat with conservative treatment methods such as electrodessiccation and curettage, or with curettage alone; and (3) Nodular basal-cell carcinoma, which essentially includes most of the remaining categories of basal-cell cancer. It is well within the scope of the present invention that it is not unusual to encounter morphologic features of several variants of basal-cell cancer in the same tumor. It is also within the scope of the present invention that Nevoid basal-cell carcinoma syndrome is treated by the system of the present invention.

According to a further embodiment, Melanoma include three categories that begin in situ, meaning they occupy only the top layers of the skin, and may become invasive; the fourth category is invasive from the start. It is herein acknowledged that invasive melanomas are more severe, as they have penetrated deeper into the skin and may have spread to other areas of the body. It is also within the scope of the invention that superficial spreading melanoma is the most common type. This melanoma grows along the top layer of the skin for a relatively long period of time before penetrating more deeply. This type of melanoma can occur in a previously benign mole. The melanoma can be found almost anywhere on the body.

Reference is now made to Lentigo maligna which is similar to the superficial spreading type, as it also remains close to the skin surface in the first stage of the disease, and usually appears as a flat or mildly elevated mottled tan, brown or dark brown discoloration. When this cancer becomes invasive, it is referred to as lentigo maligna melanoma.

Reference is now made to Acral lentiginous melanoma, also spreads superficially before penetrating more deeply. This type of melanoma can often advance more quickly than superficial spreading melanoma and lentigo maligna.

Reference is now made to Nodular melanoma, which is usually invasive at the time it is first diagnosed. The malignancy is recognized when it becomes a bump. The most frequent locations are the trunk, legs, and arms, mainly of elderly people, as well as the scalp in men. This is the most aggressive of the melanomas, and is found in 10 to 15 percent of cases.

Reference is now made to Bowen's disease, also related to as intraepidermal carcinoma, IEC or Squamous cell carcinoma in-situ.

It is further within the scope of the invention, wherein said degenerative diseases or neurological diseases or neurodegenerative diseases or disorders thereof are selected from the group consisting of: Parkinson, Alzheimer, Huntington, Alzheimer, Amyotrophic lateral sclerosis (ALS), Friedreich's ataxia, Lewy body disease, Spinal muscular atrophy, Creutzfeldt-Jakob disease, Primary progressive aphasia (PPA), Progressive supranuclear palsy (PSP) (or the Steele-Richardson-Olszewski syndrome), Multiple system atrophy, Multiple sclerosis, Niemann Pick disease, Atherosclerosis, Cancer, Essential tremor, Tay-Sachs Disease, Diabetes, Heart Disease, Keratoconus, Keratoglobus, Inflammatory Bowel Disease (IBD), Prostatitis, Osteoarthritis, Osteoporosis, Rheumatoid Arthritis, Chronic traumatic encephalopathy, Chronic Obstructive Pulmonary Disease (COPD) and Marfan's Syndrome.

It is further within the scope of the invention, wherein said plant parameters are selected from the group consisting of plant vigor, plant growth, fruit size, fruit yield, improved root system, stress tolerance, stem height, seed germination and any combination thereof.

It is further within the scope of the invention, wherein said improved water parameters are selected from the group consisting of: oxidation effect, induction of degradation of organic compounds, water purification, destruction of pathogens such as bacteria and viruses, clearing radioactive isotopes and heavy metals, sterilization, pH values, hydrogen peroxide values, water disinfection, water contamination parameters, effect on mineral ions such as calcium and magnesium, oxidation of inorganic ions and any combination thereof.

It is further within the scope of the invention, wherein the protein fingerprint or profile is associated with a cellular pathway or a protein family selected from the group consisting of signal transduction, stress response, cell cycle, antioxidation, DNA repair, replication, blood plasma proteins, glycoproteins, lypoproteins and any combination thereof.

It is further within the scope of the invention, wherein the protein fingerprint or profile is associated with a protein member selected from a group consisting of Transferin, Serum Amyloid A, XPA, PKB, IMP, MMR, XPA, hTLRs, NE, Transthyretin, LRR, Ku, NLR, catalase, superoxide dismutase, peroxidases, PAT, LTP, Apm1, NLR, LPAF, beta glucanses, Ferredoxin and any combination thereof.

It is further within the scope of the invention, wherein the plant parameters are selected from the group consisting of plant vigor, plant growth, fruit size, fruit yield, improved root system, stress tolerance, stem height, seed germination and any combination thereof.

It is further within the scope of the invention, wherein the improved fluid or gas parameters are selected from the group consisting of: oxidation effect, induction of degradation of organic compounds, water, oil or gas purification, destruction of pathogens such as bacteria and viruses, clearing radioactive isotopes and heavy metals, removal of hazardous substances such as unsaturated hydrocarbons, sulfur, nitrogen, and oxygen compounds, removal of resinous and asphaltic compounds, removal of impurities from oil, raw oil or petroleum fractions, removal of phenol and compounds and radicals thereof, removal of SO2, sterilization, pH values, hydrogen peroxide values, water or gas disinfection, water, oil, raw oil or gas contamination parameters, effect on mineral ions such as calcium and magnesium, oxidation of inorganic ions and any combination thereof.

It is further within the scope of the invention, wherein the system is adapted to provide an effect in vivo and/or in vitro.

It is further within the scope of the invention to disclose a method for generating a plasma modified field (PMF), comprising steps of: (a) emitting non thermal plasma (NTP) beam from a plasma emitting source; (b) providing a plasma modified field coupling mechanism (PMFCM) comprising a plasma beam dish having at least one opening for the passage of the plasma beam; the plasma beam dish having a first surface and a second opposite surface; and (c) a controller for controlling the PMFCM. In a core embodiment, the method further comprises a step of mounting the first surface of the plasma beam dish with: (i) at least one coupling element, and (ii) at least one reflecting element. The at least one coupling element is selected from the group consisting of: (1) at least one ferroelectric element for providing the field; (2) at least one ferromagnetic element for providing the field; (3) at least one piezoelectric element for providing the field and (4) at least one piezomagnetic element for providing said field. It is within the scope the method further comprises a step of configuring the PMFCM and the controller to adjust any of the at least one coupling and reflecting element in a predetermined pulsed manner thereby generating the PMF.

It is further within the scope of the invention to disclose a method for inducing a therapeutic or regenerative or biological or beneficial effect on a subject comprising the steps of: (a) providing a system for the administration of a plasma modified field (PMF) to a subject as defined above; and (b) applying the PMF to the subject in a predetermined manner. In this way the PMFCM and the controller are configured to adjust any of the at least one coupling and reflecting element in a predetermined manner thereby providing the PMF for inducing a therapeutic or regenerative or biochemical or biological or renewable effect or beneficial effect on the subject or on a substrate hosting at least one microorganism.

It is further within the scope of the invention to disclose the use of the system for the administration of a plasma modified field (PMF) to a subject. The use comprising steps of providing a system with: (a) a non-thermal plasma (NTP) emitting source for emitting a plasma beam; (b) a plasma modified field coupling mechanism (PMFCM) comprising a plasma beam dish having at least one opening for the passage of the plasma beam; the plasma beam dish having a first surface and a second opposite surface; and (c) a controller for controlling the PMFCM. In a core embodiment, the use further comprises a step of mounting the first surface of the plasma beam dish with: (i) at least one coupling element; and (ii) at least one reflecting element. The at least one coupling element is selected from the group consisting of: (1) at least one ferroelectric element for providing the field; (2) at least one ferromagnetic element for providing the field; (3) at least one piezoelectric element for providing the field and (4) at least one piezomagnetic element for providing said field. It is within the scope that the use further comprises a step of configuring the PMFCM and the controller to adjust any of the coupling and reflecting element in a predetermined manner thereby providing the PMF in a predetermined pulsed manner for inducing a therapeutic or biochemical or biological or renewable effect or beneficial effect on the subject or on a substrate hosting at least one microorganism.

It is further within the scope of the invention to disclose a method of manufacturing a system for the administration of a plasma modified field (PMF) to a subject comprising steps of assembling a system by steps of providing: (a) a non-thermal plasma (NTP) emitting source for emitting a plasma beam; (b) a plasma modified field coupling mechanism (PMFCM) comprising a plasma beam dish having at least one opening for the passage of the plasma beam; the plasma beam dish having a first surface and a second opposite surface; and (c) a controller for controlling the PMFCM. In a core aspect, the method comprises an additional step of mounting the first surface of the plasma beam dish with: (i) at least one coupling element, and (ii) at least one reflecting element. The at least one coupling element is selected from the group consisting of: (1) at least one ferroelectric element for providing the field; (2) at least one ferromagnetic element for providing the field; (3) at least one piezoelectric element for providing the field and (4) at least one piezomagnetic element for providing said field. It is within the scope that the method comprises an additional step of configuring the PMFCM and the controller to adjust any of the coupling and reflecting element in a predetermined manner thereby providing the PMF in a predetermined pulsed manner for inducing a therapeutic or biochemical or biological or renewable effect or beneficial or regenerative effect on the subject or on a substrate hosting at least one microorganism.

According to some aspects, the system for administering modified plasma optionally comprises a gas plasma flow regulator or monitoring mechanism configured to control and/or monitor gas plasma flow parameters such as flow rate, flow pressure, mass flow, and gas plasma composition ratios. The system may further comprise a controlling or regulating mechanism for providing modified plasma pulses in a predefined manner. Such a mechanism may comprise implemented computerized algorithm or software.

In order to understand the invention and to see how it may be implemented in practice, a plurality of preferred embodiments will now be described, by way of non-limiting example only, with reference to the following examples.

Example 1

Effect of the System for the Administration of a Plasma Modified Field on Water Parameters The effect of PMF treatment, using the system of the present invention, is herein assessed with reference to chemical analysis of water parameters. It is within the scope of the present invention that the system and method for the administration of PMF is tested for its effects on fluids and specifically on water.

An exemplary system demonstrates an effect on water chemistry parameters. In this embodiment, an apparatus for the administration of plasma modified field (i.e. generated by magnetic and/or electric fields) testes the effect of discharged PMF on water chemistry, i.e. water pH and $H_2O_2$ concentration.

Experimental Procedure

Aliquots of 10 ml distilled water were exposed to modified plasma treatments of 8, 15, 22, 29 cycles according to the pulsed profile defined in Table 3 and/or FIG. 9. The distance between the surface of the treated water and the plasma jet discharge was about 4.5 cm.

pH Measurements:

pH measurements were performed using an inoLab® Multi 9310 IDS multi-parameter system with IDS sensors (WTW-Wissenschaftlich-Technische Werkstätten GmbH, Germany). The inoLab® Multi 9310 IDS was equipped with ADA S7/IDS adaptor (WTW GmbH, Germany) and SenTix®Mic pH electrode (Ø=4.5 mm, WTW GmbH, Germany) for testing pH range from 0-14.

Hydrogen Peroxide:

Hydrogen peroxide ($H_2O_2$) was photometrically determined based on the reaction with titanyl(IV) sulfate in sulfuric acid solution. Absorption measurements of the corresponding end-product peroxotitanyl sulfate were performed with a UV-3100PC UV/Vis-Scanning-Spektralphotometer (VWR International GmbH, Germany) at Ø=405 nm.

In this embodiment the PCM reactor is mounted with a ferroelectric disk as a coupling element. The ferroelectric disk preferably characterized as follows: it has a diameter Ø of about 1 to 2.25 cm, it made of piezoelectric material such as APC 841 as described below in Table 2.

Reference is now made to Table 2, describing physical and piezoelectric properties of APC materials, available by http://www.americanpiezo.com/apc-materials/piezoelectric-properties.html.

TABLE 2

Selected properties of certain embodiments of the system of the present invention

| | APC Material: | | | | |
|---|---|---|---|---|---|
| | 840 | 841 | 850 | 855 | 880 |
| Navy Type Equivalent | Navy I | — | Navy II | Navy VI | Navy III |
| Relative Dielectric Constant | | | | | |
| $K^T$ | 1250 | 1350 | 1900 | 3300 | 1000 |
| Dielectric Dissipation Factor (Dielectric Loss(%))* | | | | | |
| tan δ | 0.40 | 0.35 | 1.40 | 1.30 | 0.35 |
| Curie Point (° C.)** | | | | | |
| $T_c$ | 325 | 320 | 360 | 250 | 310 |
| Electromechanical Coupling Factor | | | | | |
| $k_p$ | 0.59 | 0.60 | 0.63 | 0.68 | 0.50 |
| $k_{33}$ | 0.72 | 0.68 | 0.72 | 0.76 | 0.62 |
| $k_{31}$ | 0.35 | 0.33 | 0.36 | 0.40 | 0.30 |
| $k_{15}$ | 0.70 | 0.67 | 0.68 | 0.66 | 0.55 |
| Piezoelectric Charge Constant ($10^{-12}$ C/N or $10^{-12}$ m/V) | | | | | |
| $d_{33}$ | 290 | 300 | 400 | 630 | 215 |
| $-d_{31}$ | 125 | 109 | 175 | 276 | 95 |
| $d_{15}$ | 480 | 450 | 590 | 720 | 330 |
| Piezoelectric Voltage Constant ($10^{-3}$ Vm/N or $10^{-3}$ m$^2$/C) | | | | | |
| $g_{33}$ | 26.5 | 25.5 | 24.8 | 21.0 | 25.0 |
| $-g_{31}$ | 11.0 | 10.5 | 12.4 | 9.0 | 10.0 |
| $g_{15}$ | 38.0 | 35.0 | 36.0 | 27.0 | 28.0 |
| Young's Modulus ($10^{10}$ N/m$^2$) | | | | | |
| $Y^E_{11}$ | 8.0 | 7.6 | 6.3 | 5.9 | 9.0 |
| $Y_{E33}$ | 6.8 | 6.3 | 5.4 | 5.1 | 7.2 |
| Frequency Constants (Hz * m or m/s) | | | | | |
| $N_L$ (longitudinal) | 1524 | 1700 | 1500 | 1390 | 1725 |
| $N_T$ (thickness) | 2005 | 2005 | 2040 | 2079 | 2110 |
| $N_P$ (planar) | 2130 | 2055 | 2080 | 1920 | 2120 |
| Density (g/cm$^3$) | | | | | |
| ρ | 7.6 | 7.6 | 7.6 | 7.7 | 7.6 |
| Mechanical Quality Factor | | | | | |
| $Q_m$ | 500 | 1400 | 80 | 65 | 1000 |

According to specific embodiments, this example relates to properties of a system comprising a ferroelectric material APC841.

It is within the scope of the invention that the system of the present invention is configured to provide enhanced properties, i.e. improvement in at least 5% relative to the properties presented in Table 2.

It is herein acknowledged that the water quality characteristics are frequently used by reference to a set of standards against which compliance can be assessed. The most common standards used to assess water quality relate to health of ecosystems, safety of human contact and drinking water, as well as human medical process. Different uses raise different concerns and therefore different standards are considered. The system and method for administration of plasma modified field (PMF) is used in a non limiting manner for water or any other fluid such as emulsion, suspension (e.g. microbial suspension), oil, raw oil, food, beverage, milk etc. or gas purification, disinfection, cleaning of heavy metals or pollution. Other parameters which can be affected by exposure to the PMF treatment as disclosed herein include in a non limiting manner pH, dissolved oxygen, oxygen peroxide, nitric oxide (NO), Nitrate ($NO_3$) and Nitrite ($NO_2$), biochemical compounds or metabolites production, conductivity, chemical composition, oxygen reduction potential (ORP), concentration of bacteria i.e. *E. coli* and turbidity. According to some aspects, the effects provided by the system and methods of the present invention include any biological effect on a fluid or liquid including any sample, subject or substrate whose main component is fluid such as biological tissue, or microbial suspension or food or oil.

In other embodiments, the system of the present invention may be used to cause cleaning effects on the treated water or fluid as compared to a control sample. The cleaning effect may be established by parameters associated with water or any other fluid such as oil, raw oil, milk etc. or gas quality or purification of contamination. These parameters may be chemical, physical and biological characteristics of water or any other fluid such as oil, raw oil milk etc. or gas.

These affects can be achieved, for example, by the following procedure;

Plasma is delivered from a plasma emitter, i.e. a device as illustrated in FIG. 7A or 7B. A plasma modified-field (PMF) is generated and applied to the tested subjects using the plasma modified-field coupling mechanism (PMFCM) of the present invention, i.e. as illustrated in FIG. 1.

According to certain aspects of the invention, PMF is discharged in a series of pulses, i.e. as described in FIG. 9 and/or in Table 3. According to one option a set of PMF pulses is provided having increasing pulse duration in the range of 1 sec and 5 sec and increasing time laps between the pulses in the range of 1 min to 5 min.

Experimental Results

| Experiment 1 | | |
| --- | --- | --- |
| Cycles | pH | $H_2O_2$ (mg/l) |
| 0 | 6.052 | 0.000 |
| 8 | 5.965 | 0.000 |
| 15 | 5.916 | 0.000 |
| 22 | 6.027 | 1.386 |
| 29 | 5.891 | 6.727 |

| Experiment 2 | | |
| --- | --- | --- |
| Cycles | pH | $H_2O_2$ (mg/l) |
| 0 | 6.047 | 0.000 |
| 8 | 5.944 | 0.000 |
| 15 | 5.902 | 0.023 |
| 22 | 6.023 | 1.500 |
| 29 | 5.992 | 4.341 |

| Experiment 3 | | |
| --- | --- | --- |
| Cycles | pH | $H_2O_2$ (mg/l) |
| 0 | 6.063 | 0.000 |
| 8 | 5.953 | 0.000 |
| 15 | 5.911 | 0.000 |
| 22 | 6.017 | 1.159 |
| 29 | 6.009 | 3.545 |

It is herein shown that exposing water to modified plasma emitted by the system of the present invention surprisingly results in absence of significant changes in the pH level of the treated water which was maintained similar to its neutral pH level, for each of the pulse cycles used, compared to the control sample (0 pulses). Furthermore, unexpectedly the modified plasma treatments of the present invention are provided essentially without the production of $H_2O_2$ in the treated water, for treatments using less than 22 pulsed cycles (less than about 20 minutes of exposure to the modified plasma). It is emphasized that these effects are made without introducing any chemical or biological material or object to the modified plasma treated water or fluid. These results are unique and differ from currently available non-thermal plasma devices or technologies which produce $H_2O_2$ and/or demonstrate a decrease in pH level from about 6 or 7 to about 4 or less (e.g. Oehmigen, K., et al 2010, *The Role of Acidification for Antimicrobial Activity of Atmospheric Pressure Plasma in Liquids. Plasma Processes and Polymers* 7, 3-4, pp. 250-257; Satoshi Ikawa, Katsuhisa Kitano and Satoshi Hamaguchi 2010, *Effects of pH on Bacterial Inactivation in Aqueous Solutions due to Low-Temperature Atmospheric Pressure Plasma Application. Plasma Processes and Polymers*, 7, 1, pp. 33-42; Fuxiang Liu et al 2010, *Inactivation of Bacteria in an Aqueous Environment by a Direct-Current, Cold Atmospheric-Pressure Air Plasma Microjet. Plasma Process. And Polymers.* 7, pp. 231-236).

To conclude, it is submitted that the plasma modified field (PMF) system, i.e. as shown in FIGS. 1 and 2 and treatment protocols as disclosed above, is configured to provide a therapeutic or regenerative or biological or beneficial effect on water or other fluids, as well as on human, animal and plants.

Example 2

The Effect of the System for the Administration of Plasma Modified Field on Inducing a Regenerative Result on Human In order to demonstrate the therapeutic effect of plasma modified field (PMF) treatment on human and animals using the gas plasma signal device of the present invention, the following experiment is set out.

The effect of the PMF generating device of the present invention is tested on the protein profile of treated as compared to untreated control subjects. A further control made was profiling predetermined proteins before and after treatment with the system of the present invention. The protein profile of blood samples derived from treated subjects applied with the plasma pulses protocol herein disclosed is compared with the protein profile of the control subjects. Plasma is delivered from a plasma emitter, i.e. a device as illustrated in FIGS. 7A-B, in other embodiments, by a magnetic blow-out glidarc reactor. A plasma modified-field (PMF) is generated and applied to the tested subjects using the coupling mechanism (PMFCM) of the present invention, i.e. as illustrated in FIG. 1 or FIG. 2.

According to certain aspects of the invention, PMF is discharged in a series of pulses, i.e. as described in FIG. 9 and/or in Table 3.

The effect of the PMF treatment as described above, on protein regeneration, is tested in vivo by analyzing the protein profile or fingerprint in blood samples obtained before and after the treatment. Examples of proteins which may be affected by the PMF treatment include proteins associated with signal transduction, proteins associated with stress response, proteins involved in cell cycle, antioxidant related proteins and enzymes, nuclear proteins associated with DNA repair, replication factors, blood plasma proteins, glycoproteins, lypoproteins and combinations thereof. More specific examples of proteins affected by the herein disclosed NTP provided with an electromagnetic field treatment include a protein member selected from a group consisting of Transferin, Serum Amyloid A, XPA, PKB, IMP, MMR, XPA, hTLRs, NE, Transthyretin, LRR, Ku, NLR, catalase, superoxide dismutase, peroxidases and any combination thereof.

Example 3

The Effect of the System for the Administration of a Plasma Modified Field of the Present Invention on Inducing a Functional Recovery Result on Animals and Plants In order to demonstrate the effect of the PMF treatment as disclosed inter alia, on the recovery from a disruptive effect such a physical or mental disease or condition in animals and human or a stress condition in plants, the following experiment is performed.

The effect of pretreatment with the PMFCM of the present invention is tested on the functional recovery after a disruptive effect. The protein profile of pretreated subjects is compared to control subjects having the same disruptive effect but not exposed to PMF pretreatment with the gas plasma signal reactor of the present invention. The protein profile of samples derived from pretreated subjects applied with the PMF pulses protocol herein disclosed is compared with the protein profile of the control subjects. Furthermore, the protein profile of treated subjects is compared to their profile before treatment. The PMF pretreatment may be provided by the following procedure. Plasma is delivered from a plasma emitter, optionally using a gas plasma flow regulator or monitoring mechanism, i.e. a device as illustrated in FIGS. 7A-B. A plasma modified field (PMF) is generated and applied to the tested subjects using the plasma modified field coupling mechanism (PMFCM) of the present invention, i.e. as illustrated in FIG. 1 or 2.

According to certain aspects of the invention, PMF is discharged in a series of pulses, i.e. as described in FIG. 9 and/or in Table 3.

The effect of the PMF pretreatment as described above, on functional recovery, can be tested in vivo by analyzing the protein profile or fingerprint of samples obtained from the treated subjects as compared to the control subjects and/or as compared to the protein profile of the subjects before treatment. The functional recovery rate may be tested by analyzing predetermined protein candidates or biological or chemical markers at increasing time intervals from the disruptive effect. A faster recovery curve is observed in the treated subjects as compared to the control subjects. Examples of proteins which may be affected by the PMF treatment include proteins associated with signal transduction, proteins associated with stress response, proteins involved in cell cycle, nuclear proteins associated with DNA repair, replication factors, blood plasma proteins, glycoproteins, lypoproteins and combinations thereof. More specific examples of proteins affected by the herein disclosed NTP treatment include a protein member selected from a group consisting of Transferrin, Serum Amyloid A, XPA, PKB, IMP, MMR, XPA, hTLRs, NE, Transthyretin, LRR, Ku, NLR, catalase, superoxide dismutase, peroxidases and any combination thereof.

Example 4

The Effect of the System for the Administration of a Plasma Modified Field on Plants In order to demonstrate the effect of PMF treatment using the system of the present invention on plants, the following experiment is performed.

The effect of the plasma coupling system of the present invention is tested on plants exposed to the PMF as disclosed hereinabove, in comparison to untreated control plants.

Non thermal plasma is delivered from a plasma emitter, i.e. a device as illustrated in FIGS. 7A-B. A plasma modified field (PMF) is generated and applied to the tested subjects using the plasma modified field coupling mechanism (PMFCM) of the present invention, i.e. as illustrated in FIG. 1 or 2.

According to certain aspects of the invention, PMF is discharged in a series of pulses, i.e. as described in FIG. 9 and/or in Table 3.

The effect of the PMF treatment as described above is tested on various beneficial crops, particularly on the root of the plant. The regenerative effect of the treatment can be demonstrated by evaluating parameters associated with improved plant growth, improved plant yield and improved resistance to biotic and abiotic stresses. Such parameters include in a non limiting manner, plant growth rate, plant height, fruit yield, fruit size, improved and extended root system, fruit brix and combinations thereof. By using the system of the present invention improvement of at least one parameter associated with plant growth and plant yield is measured in plants exposed to the PMF, as compared to untreated control plants grown in the same conditions. Non limiting examples of candidate proteins affected by exposure of the plant (i.e. root) to PMF may include at least one of: PAT LTP, LRR, Apm1, NLR, LPAF, beta glucans and Ferredoxin.

Example 5

Equations Describing the Generated Plasma Modified Field

The plasma potential or the space potential is herein defined as the magnitude of the generated potentials and electric fields as described by the following parameters:

$\xi$ denotes a parameter defining the plasma field, i.e. plasma displacement vector, it is herein calculated by the following equation:

$$\xi(n \cdot r^3{}_D)^{-1}, \text{ where;}$$

n is the number of charged particles; and
rD is the Debye length (also called Debye radius).

$$K' = \xi \cdot m', \text{ where;}$$

m' is the modified plasma mass

In the case wherein the plasma is coupled to or generated by one type of coupling element:

Reference is now made to the energy of plasma modified by one coupling element that may be selected from the group consisting of: at least one piezoelectric element, at least one ferromagnetic element, at least one ferroelectric means and at least one piezomagnetic means, described by the following equation:

$$\varepsilon = \frac{3\pi^5 (K' \cdot T)^2}{\alpha},$$

where;

T is the temperature (also temperature per time unit); and
$\alpha$ is the field frequency of the treated subject or object.

In the case wherein the plasma is coupled to or generated by a combination of two types of coupling elements:

Reference is now made to the energy of plasma modified by two types of coupling elements selected from the group consisting of any combination of two elements selected from the group consisting of: at least one piezoelectric element, at least one ferromagnetic element, at least one ferroelectric element and at least one piezomagnetic element.
as described by the following equation:

$$\varepsilon = \frac{3\pi^5(K' \cdot T)^3}{\alpha},$$

where;
T is the temperature (also temperature per time unit); and
α is the field frequency of the treated subject or object.

Equations describing the energy resulting from the interaction between the generated plasma and the treated object The reactive energy generated by plasma modified by at least one of a piezoelectric means, a ferroelectric means, ferromagnetic means and piezomagnetic means can be described by the following equations:

$$\frac{\varepsilon}{\alpha} = m \cdot C$$
$$\varepsilon = m \cdot C \cdot \alpha,$$

where;
m is the energy mass discharged (plasma along with the coupled element/s);
C is the speed of light in a vacuum; and
α is the field frequency of the treated subject or object.

It is also within the scope of the invention that the energy characterizing the plasma modified by one type of coupling element, preferably selected from the group consisting of a piezoelectric means, a ferroelectric means, ferromagnetic means and piezomagnetic means is equal to the reactive energy of the object resulting from the PMF energy. This can be described by the following equation:

$$\varepsilon = \frac{3\pi^5(K' \cdot T)^2}{\alpha} = m \cdot C \cdot \alpha$$

It is also within the scope of the invention that the energy characterizing the plasma modified by any combination of two coupling elements selected from the group consisting of a piezoelectric means, a ferroelectric means, ferromagnetic means and a piezomagnetic means is equal to the reactive energy of the object resulting from the PMF energy. This can be described by the following equation:

$$\frac{3\pi^5(K' \cdot T)^2}{\alpha} = m \cdot C \cdot \alpha$$

Example 6

Affecting Metabolic Pathways by Treatment of Yeast with the System and Protocol for Administration of Modified Plasma of the Present Invention General Purpose of the Experiments:

Microbial production of higher alcohols by fermentation of sugars offers sustainable solutions as a potential source for next generation gasoline substitutes and alternatives to the traditional petrochemical industry. Among the most prominent examples of industrial microbial cell factory is the yeast *Saccharomyces Cerevisiae* (*S. Cerevisiae*), which is commonly used to produce ethanol as an alternative fuel. However, advanced biofuels such as n-butanol, isobutanol, and isopropanol offer superior fuel characteristics over ethanol.

The experiments described below are directed towards examining whether and under what conditions can different biofuel components or compounds or products be produced when treating industrial microorganisms such as *S. Cerevisiae* with the system for administering modified plasma and protocols as inter alia described.

Experimental Procedure:

The source for *Saccharomyces cerevisiae* used in this experiment is *S. Cerevisiae* (DSM: 1333).

The freeze dried yeast was inoculated into a culture according to the instructions provided by the supplier. The yeast was grown in Caso Bouillon growth media at room temperature for 48 hours, spread onto plate count agar plates incubated for another 48 hours at room temperature and kept refrigerated.

For these experiments the yeast was grown for 48 hours at room temperature in a nutrition broth containing 20 g glucose, 5 g peptone and 3 g yeast extract per 1 liter "Gerolsteiner" mineral water without carbon dioxide.

The plasma treatment of the yeast suspension was carried out according to the following protocol:
1. For 5 repetitions in total, two samples of 5 ml of yeast suspension were treated with the system for administering modified plasma of the present invention for one of the fixed amount of pulse cycles 3, 5 or 7 cycles (i.e. first modified plasma treatment).
2. The treated volume was pooled to gain 10 ml of yeast suspension that was treated once with the chosen number of pulse cycles for each of the 5 repetitions.
3. 5 ml of each of these 10 ml of plasma treated yeast suspension were taken for each repetition and incubated for 6 hours at room temperature under 350 rpm constant shaking.
4. After 6 hours of incubation, 1.5 ml were taken from each sample for gas chromatographic analyses.
5. The remaining amount of suspension was incubated under the same conditions for additional 18 and 42 hours.
6. 24 and 48 hours after the plasma treatment another 1.5 ml sample was taken for gas chromatographic analysis.
7. The remaining 5 ml from each sample were treated for a second time, 1 hour after the first plasma treatment (i.e. second modified plasma treatment).
8. After the second modified plasma treatment (exactly the same treatment as the first modified plasma treatment) the samples were also incubated at room temperature while shaking with 350 rpm.
9. Samples for gas chromatographic analysis were taken after 6, 24 and 48 hours of incubation in total.
10. Parallel to the plasma treated samples; 5 ml of the untreated yeast suspension was incubated under exactly the same conditions as the treated samples and analyzed by gas chromatography. This untreated samples used as the control against which the measurement results are compared to.
11. The untreated yeast suspension diluted and spread onto plate count agar plates and incubated at room temperature for 48 hours. The colonies were counted and the starting concentration of the yeast suspension was calculated.

It is noted that the protocol described above was repeated for each set of modified plasma pulse cycles.

The concentration of the yeast suspensions were as follows:
3 pulse cycles: 2,4*10^8 cfu*ml−1
5 pulse cycles: 2,3*10^8 cfu*ml−1
7 pulse cycles: 1,1*10^8 cfu*ml−1

The NTP source used in this experiment is preferably a plasma jet. The gas plasma discharge comprises a combination of Argon, $N_2$ and $O_2$, i.e. as defined in Table 1. The gas flow rate is between about 3-4 liters per minute. The plasma power is about 2 W.

It is further within the scope that the distance between the jet discharge and the treated sample is between about 1 cm and up to about 5 cm, particularly between about 3 cm and about 5 cm.

A 'pulse cycle' or a 'cycle' is herein defined as a predefined pulse series profile, as demonstrated in FIG. 9 and/or in Table 3 below.

tion. The columns define the sequential number of the pulse in the cycle ($1^{st}$ pulse, $2^{nd}$ pulse etc.). Each one of the pulses is described by the pulse duration in seconds (the left number), which is followed by a pause in seconds (the right number). A cycle or a pulse cycle is defined as a series of pulses ($1^{st}$ pulse, $2^{nd}$ pulse etc.), as illustrated in one horizontal row. It is further within the scope of the present invention that any combination of the above defined pulses can be used and applied in the modified plasma treatments of the present invention. In some embodiments, the duration of one cycle or pulse cycle is between about 10 seconds and about 120 seconds, and more particularly between about 20 seconds and about 60 seconds.

The identification of the biofuel products was carried out by analytical analysis procedure using a Headspace sampler (i.e. 7697A, Agilent).

TABLE 3

Examples of pulse cycle profiles

| $1^{st}$ pulse | $2^{nd}$ pulse | $3^{rd}$ pulse | $4^{th}$ pulse | $5^{th}$ pulse | $6^{th}$ pulse | $7^{th}$ pulse | $8^{th}$ pulse | $i^{th}$ pulse |
|---|---|---|---|---|---|---|---|---|
| 1/1 | 1/1 | 1/1 | 1/1 | 1/1 | 1/1 | 1/1 | 1/1 | 1/1 |
| 1/2 | 1/2 | 1/2 | 1/2 | 1/2 | 1/2 | 1/2 | 1/2 | 1/2 |
| 1/4 | 1/4 | 1/4 | 1/4 | 1/4 | 1/4 | 1/4 | 1/4 | 1/4 |
| 1/6 | 1/6 | 1/6 | 1/6 | 1/6 | 1/6 | 1/6 | 1/6 | 1/6 |
| 2/1 | 2/1 | 2/1 | 2/1 | 2/1 | 2/1 | 2/1 | 2/1 | 2/1 |
| 2/2 | 2/2 | 2/2 | 2/2 | 2/2 | 2/2 | 2/2 | 2/2 | 2/2 |
| 4/1 | 4/1 | 4/1 | 4/1 | 4/1 | 4/1 | 4/1 | 4/1 | 4/1 |
| 4/2 | 4/2 | 4/2 | 4/2 | 4/2 | 4/2 | 4/2 | 4/2 | 4/2 |
| 4/4 | 4/4 | 4/4 | 4/4 | 4/4 | 4/4 | 4/4 | 4/4 | 4/4 |
| 8/1 | 8/1 | 8/1 | 8/1 | 8/1 | 8/1 | 8/1 | 8/1 | 8/1 |
| 8/2 | 8/2 | 8/2 | 8/2 | 4/2 | 8/2 | 4/2 | 8/2 | 8/2 |
| 8/4 | 8/4 | 8/4 | 8/4 | 8/4 | 8/4 | 8/4 | 8/4 | 8/4 |
| 1/1 | 2/1 | 3/1 | 4/1 | 5/1 | 6/1 | 7/1 | 8/1 | i/1 |
| 1/2 | 2/2 | 3/2 | 4/2 | 5/2 | 6/2 | 7/2 | 8/2 | i/2 |
| 1/j | 2/j | 3/j | 4/j | 5/j | 6/j | 7/j | 8/j | 1 − i/j |
| i/j | 1 + k/j | 1 + k//j | 1 + k/j | 1 + k/j | 1 + k/j | 1 + k/j | 1 + k/j | 1 + k/j |
| 1 * f(k)/j | 1 * f(k/j | 1 * f(k/j | 1 * f(k/j | 1 * f(k/j | 1 * f(k/j | 1 * f(k/j | 1 * f(k/j | 1 * f(k)/j |
| i/j + q | 1 + k/j + q | 1 + k//j + q | 1 + k/j + q | 1 + k/j + q | 1 + k/j + q | 1 + k/j + q | 1 + k/j + q | 1 + k/j + q |
| 1 * f(k)/ j * f(q) | 1 * f(k)/ j * f(q) | 1 * f(k)/ j * f(q) | 1 * f(k)/ j * f(q) | 1 * f(k)/ j * f(q) | 1 * f(k)/ j * f(q) | 1 * f(k)/ j * f(q) | 1 * f(k)/ j * f(q) | 1 * f(k)/j * f(q) |
| 1 * f(k) + a/ j * f(q) + b | 1 * f(k) + a/ j * f(q) + b | 1 * f(k) + a/ j * f(q) + b | 1 * f(k) + a/ j * f(q) + b | 1 * f(k) + a/ j * f(q) + b | 1 * f(k) + a/ j * f(q) + b | 1 * f(k) + a/ j * f(q) + b | 1 * f(k) + a/ j * f(q) + b | 1 * f(k) + a/ j * f(q) + b |
| 1/1 | 2/2 | 3/3 | 4/4 | 5/5 | 6/2 | 1/1 | 2/n | 1 * f(k) + a/ j * f(q) + b |
| 1/1 | 6/2 | 5/5 | 4/4 | 3/3 | 2/2 | 1/1 | 1/n | 1 * f(k) + a/ j * f(q) + b |
| 1/2 | 2/3 | 3/4 | 4/5 | 5/6 | 6/3 | 1/2 | 1/n | 1 * f(k) + a/ j * f(q) + b |
| 1/2 | 6/3 | 5/6 | 4/7 | 3/4 | 2/3 | 1/2 | 1/n | 1 * f(k) + a/ j * f(q) + b |
| 1/1 | 3/2 | 5/3 | 7/4 | 5/5 | 3/6 | 2/5 | 1/n | 1 * f(k) + a/ j * f(q) + b |
| 7/1 | 6/2 | 5/3 | 4/3 | 3/3 | 2/2 | 1/1 | 1/n | 1 * f(k) + a/ j * f(q) + b |
| 1/4 | 3/3 | 5/2 | 7/1 | 5/2 | 3/3 | 2/4 | 1/n | 1 * f(k) + a/ j * f(q) + b |
| 2/2 | 3/2 | 4/2 | 5/3 | 6/3 | 5/2 | 4/5 | 3/n | 1 * f(k) + a/ j * f(q) + b |
| 8/8 | 7/7 | 6/6 | 5/5 | 4/4 | 3/3 | 2/2 | 1/n | 1 * f(k) + a/ j * f(q) + b |
| 8/2 | 7/3 | 6/4 | 5/5 | 4/4 | 3/3 | 2/2 | 1/n | 1 * f(k) + a/ j * f(q) + b |
| 8/2 | 7/3 | 7/2 | 7/1 | 6/3 | 5/3 | 4/3 | 2/n | 1 * f(k) + a/ j * f(q) + b |
| 8/1 | 8/1 | 7/1 | 6/1 | 5/2 | 4/3 | 3/4 | 2/n | 1 * f(k) + a/ j * f(q) + b |

Reference is now made to Table 3 presenting examples of pulse cycle profiles within the scope of the present invention.

The separation was done with a 7890A GC system in combination with a 5975C mass detector (both Agilent).

The compounds identified with the NIST-Database included: Ethanol, 2-Propanol, 1-Propanol, 2,3-Butanedione, Acetoin and 2,3-Butanediole.

The term '1-Propanol' is herein refers in a non-limiting manner to a primary alcohol with the formula $CH_3CH_2CH_2OH$. It is also known as propan-1-ol, 1-propyl alcohol, n-propyl alcohol, and n-propanol.

The term '2-Propanol' is herein refers in a non-limiting manner to Isopropyl alcohol and isopropanol.

The term '2,3-Butanedione' is herein refers in a non-limiting manner to Diacetyl, butane-2,3-dione, vicinal diketone, 1,2-diketones.

The term 2,3-Butanediol $[(CH3)2(CHOH)2]$ also refers to its three stereoisomers, consisting of two enantiomers and one meso compound.

The term 'Acetoin' is herein refers in a non-limiting manner to 3-hydroxybutanone or acetyl methyl carbinol or (R)-acetoin.

The present invention further encompasses isomers, stereoisomers and derivatives of the above mentioned compounds.

Experimental Results:

Reference is now made to FIG. 10 presenting a graphic illustration of the metabolic compounds produced by *S. cerevisiae* exposed to one modified plasma treatment (FIG. 10A) or two modified plasma treatments of 5 pulse cycles each (FIG. 10B), as compared to non-treated (control) *S. cerevisiae* (FIG. 10C). It should be noted that the duration of each 5 pulse cycle treatment is about 3.5 minutes. It is surprisingly shown that by exposing the yeast *S. cerevisiae* to 5 cycles of modified plasma treatment, enhanced production of advanced biofuels compounds is observed as compared to untreated yeast. More specifically, the signal level of 2, 3-Butanediole is increased after 24 hours recovery from the one and/or two modified plasma treatments (FIGS. 10 A and B). Furthermore, the levels of 1-Propanol and 2-Propanol are dramatically increased already after 6 hours from the one and or two treatments (FIGS. 10 A and B). On the other hand, the observed Acetoin signal levels produced by the treated yeast are decreased as a result of one (FIG. 10 A) or two (FIG. 10 B) modified plasma treatments, as compared to the untreated control yeast (FIG. 10 C).

Reference is now made to FIG. 11 which presents a graphic illustration of the metabolic compounds produced by *S. cerevisiae* exposed to one (FIG. 11A) or two (FIG. 11B) modified plasma treatments of 7 pulse cycles, as compared to control untreated *S. cerevisiae* (FIG. 11C). It can be seen that after 6 hours recovery from the exposure to the modified plasma treatment, the production signal levels of 1-Propanol, 2-Propanol and 2,3-Butanedione have been significantly increased in the treated yeast (one and two treatments, FIG. 11A and FIG. 11B respectively) relative to the control yeast (FIG. 11C). After 24 hours from the modified plasma treatment, the signal levels of 1-Propanol and 2-Propanol were maintained high (FIG. 11A and FIG. 11B), while the level of 2,3-Butanediole was similar to the control (FIG. 11C).

Thus it is demonstrated that exposure of *S. cerevisiae* to the about 3.5 or about 4.9 minutes pulsed modified plasma treatment of the present invention, induce the production of 1-Propanol, 2-Propanol and 2,3-Butanedione by the treated yeast, relative to the control untreated yeast. The production of theses biochemical compounds can be detected already about 6 hours or earlier after the treatment.

Reference is now made to FIG. 12 which presents a quantitative graphic illustration of the concentration of the metabolic or biochemical compounds produced by *S. cerevisiae* exposed to one modified plasma treatment (FIG. 12A) or two modified plasma treatments (FIG. 12B) of 5 pulse cycles, as compared to control *S. cerevisiae* (FIG. 12C). This figure clearly shows the markedly enhanced production of 1-Propanol and 2-Propanol in the treated yeast. The concentration of 1-Propanol and 2-Propanol was undetected in the control yeast during up to 24 hours (FIG. 12C). On the other hand, in the treated yeast exposed to two modified plasma treatments of 5 pulse cycles (FIG. 12B), the concentration of 1-Propanol and 2-Propanol reached about 40 μl/l and about 30 WA respectively, after 6 h recovery from the treatment when the duration of each treatment was maximum about 3.5 minutes.

Reference is now made to FIG. 13 presenting a quantitative graphic illustration of the concentration of the biochemical compounds produced by *S. cerevisiae* exposed to one modified plasma treatment (FIG. 13A) or two modified plasma treatments (FIG. 13B) of 7 pulse cycles as compared to control untreated *S. cerevisiae* (FIG. 13C). It can be seen that induction of 1-Propanol and 2-Propanol production is achieved in *S. cerevisiae* treated with the modified plasma administration system and protocol of the present invention. The measured concentration of 1-Propanol and 2-Propanol, detected 6 hour after treatment is about 40 μl/l and between about 20 to 25 OA respectively.

The concentration of the produced biofuel biochemical products in milligram per liter is estimated in Table 4 as follows:

TABLE 4

Estimation of 1-Propanol and 2-Propanol concentration (mg/l) in the yeast suspension

| No. of pulse cycles | One treatment | Two treatments | Control |
|---|---|---|---|
| 1-Propanol (mg/l) | | | |
| 3 | 20.47 | 31.46 | — |
| 5 | 25.45 | 35.33 | 0 |
| 7 | 20.30 | 31.55 | 0 |
| 2-Propanol (mg/l) | | | |
| 3 | 15.30 | 22.50 | — |
| 5 | 18.78 | 24.99 | 0 |
| 7 | 16.03 | 20.60 | 0 |

The results described above clearly show that the endogenous production of the compounds 2,3-Butanediole, 1-Propanol and 2-Propanol is induced in *S. cerevisiae* exposed to modified plasma treatments administered by the system for generating modified plasma of the present invention, according to a predefined pulse protocol. It is further surprisingly shown that enhanced production of these important and advanced generation biofuel compounds is observed up to 6 to 24 hours incubation after the yeast treatment. The duration of one treatment is between about 3.5 and up to about 4.9 min; and about 7 to about 9.8 minutes for two treatments, with 1 hour pause between the treatments. It is additionally demonstrated that 1-Propanol production reaches a concentration of between about 30 mg/l to about 40 mg/l, and 2-Propanol production reaches a concentration of between about 20 mg/l to about 30 mg/l, 6 hours after the yeast treatment.

To summarize, the present invention provides a method to produce advanced generations biofuel compounds such as short chain alcohols by exposing microorganisms i.e. *S. cerevisiae* to modified plasma administration. It is noted that the short chain alcohols (i.e. 2,3-Butanediole, 1-Propanol and 2-Propanol) production is achieved rapidly, after up to about 6 to about 24 hours from a short period treatment of at the most about 3 to about 6 min (or about 7 to about 10 minutes for two treatments with 1 hour pause between the treatments). It is further noted that the effect on the yeast endogenous metabolic pathways is achieved without engineering (i.e. DNA manipulation) of the yeast, or pretreatment with additional materials as reported up until now. The production of advantageous biofuels by utilizing *S. cerevisiae* treated by the method of the present invention, provide a sustainable and/or renewable solution for commercial production of alternative energy sources.

7. Spiral plate count method
   50 μl of the plasma treated samples where spiral plated on XLD-Agar immediately after treatment (0), 1 hour after treatment (60) and 1.5 hours after modified plasma treatment (90). The agar plates where incubated for 48 h and 37° C. and the number of colonies was counted (i.e. colony forming units or CFU).

Experimental Results:

TABLE 5

Means and standard deviations of Listeria monocytogenes survival results of three experimental measurements (CFU measures)
Listeria monocytogenes CFU mean value (MV) and standard deviation (SD)

| Time from modified plasma treatment (min) | Cycles | | | | | | | |
|---|---|---|---|---|---|---|---|---|
| | 3 | | 5 | | 11 | | Control | |
| | MV | SD | MV | SD | MV | SD | MV | SD |
| 0 | 1.51E+03 | 6.82E+02 | 2.74E+01 | 3.10E+01 | 0.00E+00 | 0.00E+00 | 3.53E+04 | 2.61E+03 |
| 60 | 4.78E+01 | 6.51E+01 | 0.00E+00 | 0.00E+00 | 0.00E+00 | 0.00E+00 | 1.32E+04 | 2.94E+03 |
| 90 | 0.00E+00 | 0.00E+00 | 0.00E+00 | 0.00E+00 | 0.00E+00 | 0.00E+00 | 9.59E+03 | 2.56E+03 |

Example 7

Effect of Exposure to the Modified Plasma Administration System on Deactivating or Inactivation of Bacteria Reference is now made to an experiment showing the effect of the modified plasma treatment on *Listeria monocytogenes*.

The Experimental Protocol Comprises the Following Steps:
1. Preparation of an overnight culture:
   One colony of *L. monocytogenes* was suspended in a culture medium and incubated for 48 h at 37° C.
2. Preparation of the stock solution:
   The overnight culture was centrifuged at 4500 rpm.
   The supernatant was decanted and the cell pellet was resuspended with sterile NaCl solution.
3. Dilution
   The stock solution has been diluted to get ~$10^4$ CFU/ml concentration of working solution.
4. Sampling
   Aliquots (i.e. 100 μl) of the working solution have been transferred into petri dishes (diameter=60 mm) with 5 ml sterile NaCl.
   Every sample was weighed before the modified plasma treatment (because the modified plasma treatment may cause evaporation).
5. Modified plasma treatment
   Gas mixture composition: Argon, $N_2$ and $O_2$, i.e. as defined in Table 1.
   Pulse cycles: 3, 5 and 11 (i.e. as defined in FIG. 9 and/or in Table 3).
6. Adjust evaporation
   After the plasma treatment the samples where weighed again and the fluid loss was adjusted with sterile NaCl.

The results described above show the significant effect of the modified plasma treatments described in the present invention on bacterial sterilization. It is demonstrated that exposure of bacteria (i.e. *Listeria monocytogenes*) for about 2 minutes to modified plasma treatment (3 pulse cycles) results in deactivating about 95% of the treated bacteria immediately after the treatment (0) relative to the untreated control bacteria. It is further demonstrated that exposure of bacteria (i.e. *Listeria monocytogenes*) for about 2 minutes to modified plasma treatment (3 pulse cycles) results in destroying/deactivating about 99% of the treated bacteria 60 minutes after the treatment and inactivating the treated bacteria 90 min after the 2 minutes (3 pulse cycles) treatment. Modified plasma treatment for about 3.5 min (5 pulse cycles) results in deactivation of about 99% of the treated bacteria immediately after the treatment and loss of treated bacterial viability after 60 min from the exposure to the modified plasma treatment. It is further shown in Table 5 that modified plasma treatment for about 7.7 minutes results in deactivation of the treated *listeria* bacteria, known as a harmful human pathogen, immediately after the exposure to the plasma modified treatment.

Reference is now made to an experiment showing the effect of the modified plasma treatment on *Escherichia coli* (*E. coli*).

The Experimental Protocol Comprises the Following Steps:
1. Preparation of an overnight culture
   One colony of *E. coli* was suspended in culture medium and incubated for 24 h at 37° C.
2. Preparation of the stock solution
   10 ml of the overnight culture was centrifuged at 4500 rpm.
   The cell pellet was re-suspended with 10 ml sterile NaCl solution.
3. Dilution
   The stock solution was diluted with sterile NaCl to get ~$10^4$ CFU/ml working solution.
4. Sampling
   100 μl aliquots of the working solution was transferred into petri dishes (diameter=60 mm) with 5 ml sterile NaCl.

Every sample was weighed before the plasma treatment.
5. Plasma treatment
Gas mixture composition: Argon, $N_2$ and $O_2$, i.e. as defined in Table 1.
Cycles: 8, 15, 22 and 29 (i.e. as defined in FIG. 9 and/or in Table 3).
6. Adjust evaporation
After the plasma treatment the samples where weighed again and the fluid loss was adjusted with sterile NaCl.
7. Spiral plate count method
50 µl of the plasma treated samples where spiral plated on CaSo-Agar immediately after treatment (0), 1 hour after treatment (60) and 1.5 hours after modified plasma treatment (90). The agar plates where incubated for 24 h at 37° C.

production of biochemical compounds) may be achieved without significantly affecting or altering chemical parameters such as pH or $H_2O_2$ concentration or other oxidation or redox parameters and/or processes of the treated sample. The demonstrated beneficial effects may result from synergistic characteristics of the modified plasma system and/or treatment protocol. It is within the scope that the system and method of the present invention is useful for providing biological effects beneath the outer integument of the treated sample or subject, for example human tissue, without providing undesirable or adverse effects such as lowering the pH or elevating $H_2O_2$ concentration.

TABLE 6

Means and standard deviations of *E. coli* survival results of three experimental measurements (CFU measures)
*Escherichia coli* in NaCl, CFU mean value (MV) and standard deviation (SD)

| Time from modified plasma treatment (min) | Cycles | | | | | | | | | |
|---|---|---|---|---|---|---|---|---|---|---|
| | 8 | | 15 | | 22 | | 29 | | Control | |
| | MV | SD | MV | SD | MV | SD | MV | SD | MV | SD |
| 0 | 7.57E+03 | 1.07E+04 | 3.05E+03 | 4.31E+03 | 6.40E+03 | 9.05E+03 | 0.00E+00 | 0.00E+00 | 9.17E+04 | 8.71E+02 |
| 60 | 4.77E+03 | 6.74E+03 | 2.04E+01 | 2.88E+01 | 0.00E+00 | 0.00E+00 | 0.00E+00 | 0.00E+00 | 9.42E+04 | 5.35E+02 |
| 90 | 0.00E+00 | 0.00E+00 | 1.37E+01 | 1.93E+01 | 0.00E+00 | 0.00E+00 | 0.00E+00 | 0.00E+00 | 9.41E+04 | 8.99E+02 |

The results described above show the significant effect of the modified plasma treatments described in the present invention on bacterial sterilization. It is demonstrated that exposure of bacteria (i.e. *E. coli*) for about 5 minutes to modified plasma treatment (8 pulse cycles) results in: deactivating about 92% of the treated bacteria immediately after the treatment relative to control; loss of about 95% of the treated bacteria (relative to control) after recovery of 60 minutes following the treatment; and furthermore it demonstrates deactivation of the treated bacteria 90 min after the about 5 minutes treatment. Modified plasma treatment for about 10 min (15 pulse cycles) results in deactivating of about 96% of the treated bacteria (relative to control) immediately after the modified plasma treatment, and about 99% loss of bacterial viability after 60 min from the exposure to the modified plasma treatment. It is further seen from Table 6 that exposure of bacteria to modified plasma treatment for about 20 min (29 pulse cycles) results in deactivating the treated *E coli* bacteria immediately after the treatment.

To summarize, the present invention unexpectedly demonstrates that by using the modified plasma system and methods of the present invention, microbial metabolic, anabolic or amphibolic pathways can be efficiently affected to alter metabolite production, for example to enhance microbial production of highly important next or advanced generation sustainable and renewable biofuels. It further demonstrates that bacterial sterilization or disinfection or antimicrobial activity can be achieved by the relatively short and highly efficient modified plasma administration treatments of the present invention.

The present invention further shows that the biological or biochemical effects provided by the modified plasma treatments as presented inter alia (i.e. microbial sterilization or

The invention claimed is:

1. A method of increasing production of advanced biofuel compounds (ABCs) in yeast, wherein said method comprises steps of:
   a. providing a system for administering modified plasma, said system comprises:
      i. a non-thermal plasma (NTP) emitting source for emitting a NTP beam;
      ii. a plasma coupling mechanism (PCM), said PCM comprises a plasma beam dish having at least one opening for the passage of said NTP beam; said plasma beam dish having a first surface and a second opposite surface; said first surface of said plasma beam dish is mounted with at least one coupling element selected from a group consisting of:
         (1) at least one ferroelectric element for providing a ferroelectric induced field for coupling with said NTP beam;
         (2) at least one ferromagnetic element for providing a ferromagnetic induced field for coupling with said NTP beam;
         (3) at least one piezoelectric element for providing a piezoelectric induced field for coupling with said NTP beam; and
         (4) at least one piezomagnetic element for providing a piezomagnetic induced field for coupling with said NTP beam; said system additionally comprises at least one reflecting element configured to focus said NTP beam thereby generating modified plasma beam;
   b. providing a substrate hosting said yeast; and,
   c. administering said modified plasma beam in a predetermined pulsed manner to yeast hosted in said substrate thereby providing an increased production of said ABCs compared to untreated yeast.

2. The method of claim 1, wherein said substrate is selected from the group consisting of: liquid, beverage, suspension, biological culture, medium, growth medium, emulsion, plant, fluid, soil, minerals, gas and liquid mixtures, gas mixtures, and any combination thereof.

3. The method of claim 1, additionally comprises steps of said increasing production of advanced biofuel compounds (ABCs) in yeast in 6 to 24 hours incubation from said administration of said modified plasma beam.

4. The method of claim 1, further comprising harvesting said ABCs.

5. The method according to claim 1, further comprising selecting said ABCs from the group consisting of biofuel and/or products thereof, biodiesel and/or products thereof, gas compounds, alcohol compounds, and any combination thereof.

6. The method according to claim 1, further comprising selecting said ABCs from the group consisting of 1-propanol, 2-propanol, 2,3-butanedione, vicinal diketone, acetoin, 2,3-butanediole, any isomer or racemic compound thereof, any intermediate pathway compound or precursor thereof, and any mixture thereof.

7. The method according to claim 1, further comprising inducing the production of said ABCs to a concentration of between about 5 mg/l to about 200 mg/l.

8. The method of claim 1, wherein said yeast is *saccharomyces cerevisiae*.

9. A system for administering modified plasma to a substrate hosting yeast, said system comprising:
   a. a non-thermal plasma (NTP) emitting source for emitting a NTP beam; and
   b. a plasma coupling mechanism (PCM), said PCM comprises a plasma beam dish having at least one opening for passage of said NTP beam; said plasma beam dish having a first surface and a second opposite surface; said first surface of said plasma beam dish comprises at least one coupling element selected from a group consisting of:
      i. at least one ferroelectric element for providing a ferroelectric induced field for coupling with said NTP beam;
      ii. at least one ferromagnetic element for providing a ferromagnetic induced field for coupling with said NTP beam;
      iii. at least one piezoelectric element for providing a piezoelectric induced field for coupling with said NTP beam; and
      iv. at least one piezomagnetic element for providing a piezomagnetic induced field for coupling with said NTP beam;

said system additionally comprises at least one reflecting element configured to focus said plasma beam, thereby providing said modified plasma in a predetermined pulsed manner, wherein said system increases production of advanced biofuels compounds (ABCs) compared to untreated yeast.

10. The system of claim 9, wherein said NTP emitting source is selected from the group consisting of a dielectric barrier discharger, an atmospheric pressure glow discharger, a corona plasma discharger, a high voltage DC corona discharger, a high voltage negative DC corona discharger, a high voltage positive DC corona discharger, a floating electrode dielectric barrier discharger, gliding arc discharge (GD) induced plasma and a plasma jet.

11. The system of claim 9, wherein said at least one coupling element at least partially comprises Polyvinylidene fluoride, polyvinylidene difluoride (PVDF), PZT, lead zirconium titanate, ferroelectric oxides, $Pb[Zr(x)Ti(1-x)]O_3$, $PbZrO_3$, $PbTiO_3$, Barium Titanate ($BaTiO_3$), $(Ba, Sr)TiO_3$, $Ba(1-x) Sr(x)TiO_3$, a ferroelectric material characterized by at least one of piezoelectricity, pyroelectricity and memory properties, a permanent magnet, an electromagnet, a superconducting magnet, Cobalt, Magnetite ($Fe_3O_4$), α-ferrite (α Fe), iron, ferromagnetic alloys, piezomagnetic ferrite materials, magnetoelectric ceramic materials and any combination thereof.

12. The system of claim 9, wherein said at least one reflecting element at least partially comprises a material or element selected from the group consisting of: a reflector coating, metals, iron, metal alloys, stainless steel, aluminum, silver, gold and mixtures thereof, dielectric coating, ultraviolet coating, UV reflecting materials, 100-280 nm reflecting materials, glass, amorphous materials, solid materials, insoluble materials, crystalline materials polymers and any combination thereof.

13. The system of claim 9, wherein said at least one coupling element is arranged in at least one set of pairs or triplicates or in at least one set of more than three coupling elements.

14. The system of claim 9, wherein said ABCs are selected from the group consisting of 1-propanol, 2-propanol, 2,3-butanedione, vicinal diketone, acetoin, 2,3-butanediole, any isomer or racemic compound thereof, any intermediate pathway compound or precursor thereof, and any mixture thereof.

15. The system of claim 9, wherein said yeast is *saccharomyces cerevisiae*.

* * * * *